United States Patent [19]

Engel et al.

[11] Patent Number: 4,873,236

[45] Date of Patent: Oct. 10, 1989

[54] CONDENSED DIAZEPINONES, PROCESSES FOR PREPARING THEM AND PHARMACEUTICAL COMPOSITIONS CONTAINING THESE COMPOUNDS

[75] Inventors: Wolfhard Engel; Wolfgang Eberlein; Gerhard Mihm, all of Biberach; Gunter Trummlitz, Warthausen; Norbert Mayer, Biberach, all of Fed. Rep. of Germany; Adriaan De Jonge, Driebergen, Netherlands

[73] Assignee: Dr. Karl Thomae GmbH, Biberach an der Riss, Fed. Rep. of Germany

[21] Appl. No.: 136,212

[22] Filed: Dec. 18, 1987

[30] Foreign Application Priority Data

Dec. 20, 1986 [DE] Fed. Rep. of Germany ....... 3643666

[51] Int. Cl.$^4$ ..................... A61K 31/55; C07D 417/14
[52] U.S. Cl. ..................................... 514/220; 540/495
[58] Field of Search .......................... 540/495; 514/220

[56] - References Cited

U.S. PATENT DOCUMENTS

| 3,691,159 | 9/1972 | Schmidt et al. | 540/495 |
| 4,410,527 | 10/1983 | Engel et al. | 540/495 |
| 4,424,222 | 1/1984 | Engel et al. | 540/495 |
| 4,724,236 | 2/1988 | Eberlein et al. | 540/495 |

FOREIGN PATENT DOCUMENTS

| 0039519 | 11/1981 | European Pat. Off. | 540/495 |
| 0044989 | 2/1982 | European Pat. Off. | 540/495 |
| 0057428 | 8/1982 | European Pat. Off. | 540/495 |
| 0066774 | 12/1982 | European Pat. Off. | 540/495 |
| 0125607 | 11/1984 | European Pat. Off. | 540/495 |
| 0156191 | 10/1985 | European Pat. Off. | 540/495 |
| 2065570 | 7/1974 | Fed. Rep. of Germany | 540/495 |
| 2424811 | 12/1975 | Fed. Rep. of Germany | 540/495 |
| 236731 | 6/1986 | German Democratic Rep. | 540/495 |

*Primary Examiner*—Robert T. Bond
*Attorney, Agent, or Firm*—David E. Frankhouser; Alan R. Stempel; Mary-Ellen M. Timbers

[57] ABSTRACT

There are described new condensed diazepinones of general formula

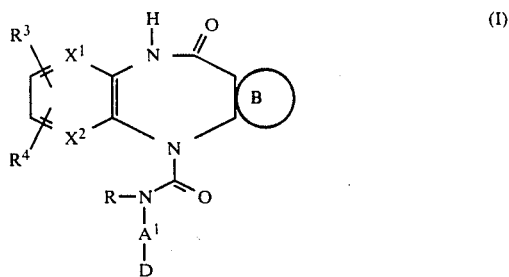

wherein B represents one of the divalent groups

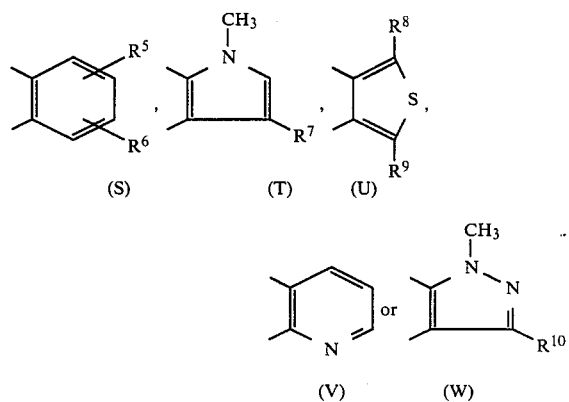

and D represents the groups

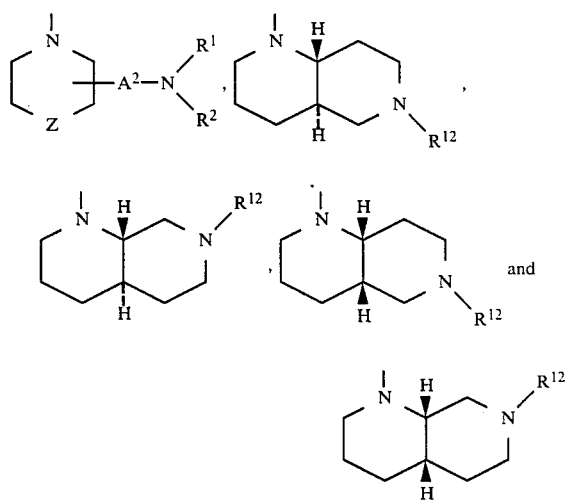

and $X^1$, $X^2$ represents a =CH— group or, if B assumes the meaning of the divalent group S, U or W, they may also represent an N atom, $A^1$ and $A^2$ in general represent lower alkylene groups, Z represents a C—C bond or the groups, —O—, —S—, —CH$_2$—, or —(CH$_2$)$_2$—; R represents hydrogen or methyl, $R^1$ and $R^2$ generally represent alkyl groups which, together with the nitrogen atom between them, may also form a saturated monocylic, heterocyclic group, $R_3$ represents alkyl, chlorine or hydrogen, $R_4$ represents hydrogen or methyl, $R^5$ and $R^6$ represent hydrogen, halogen or alkyl, $R_7$ represents hydrogen, chlorine or methyl, $R^8$ represents hydrogen or lower alkyl, $R^9$ represents hydrogen, halogen, lower alkyl and $R^{10}$ represents hydrogen or methyl and $R^{12}$ represents branched or unbranched alkyl. The compounds of general formula I and the acid addition salts thereof may be resolved into their isomers. The compounds of formula I and their salts may be used as vagal pacemakers for the treatment of bradycardia and bradyarrhythmia.

6 Claims, No Drawings

CONDENSED DIAZEPINONES, PROCESSES FOR PREPARING THEM AND PHARMACEUTICAL COMPOSITIONS CONTAINING THESE COMPOUNDS

The invention relates to new condensed diazepinones, processes for preparing them and pharmaceutical compositions containing these compounds.

Condensed diazepinones with ulcer-inhibiting and gastric acid secretion inhibiting properties are already known from EP-A-39 519 and EP-A-57428 and from US-A-3660380, US-A-3691159; US-A-4213984, US-A-4213985, US-A-4210648, US-A-4410527, US-A-4424225, US-A-4424222 and US-A-4424226.

EP-A-156191 discloses that by introducing novel aminoacyl groups in the compounds of the above-mentioned publications it is possible to induce completely different, valuable pharmacological properties. Compared with these compounds, the condensed diazepinones according to the invention are distinguished by a considerably more powerful effect and marked stability to hydrolysis, whilst having comparable or better selectivity and resorption after oral administration.

The new condensed diazepinones have the general formula I

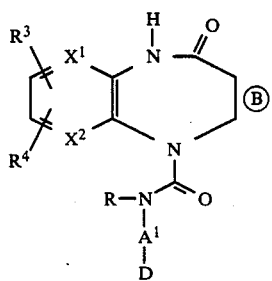

(I)

wherein ⟩ Ⓑ represents one of the divalent groups

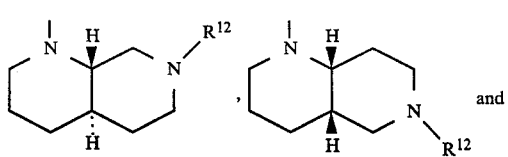

(S)   (T)   (U)

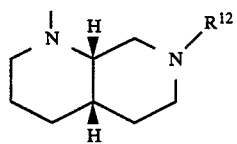

(V)   (W)

and D represents the groups

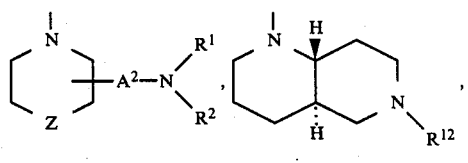

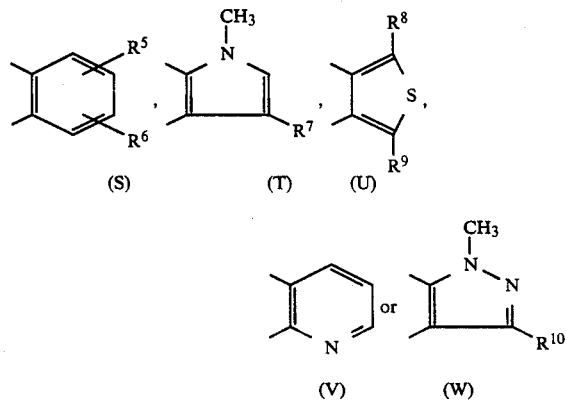

and $X^1$, $X^2$, $A^1$, $A^2$, R, $R^1$ to $R^{10}$, $R^{12}$ and Z have the following meanings:

$X^1$ and $X^2$ represent a =CH— group or, if ⟩ Ⓑ assumes the meanings of the above-mentioned divalent groups S, U or W, both or only $X^1$ or only $X^2$ may also represent a nitrogen atom;

$A^1$ is a straight-chained or branched saturated alkylene group with two to seven carbon atoms;

$A^2$ is a straight-chained or branched saturated alkylene group with 1 to 5 carbon atoms or, if it is in the 3-position relative to the nitrogen of the saturated heterocyclic ring, it may also represent a single bond;

Z represents a single bond, an oxygen or sulphur atom, a methylene or 1,2-ethylene group;

R represents a hydrogen atom or a methyl group;

$R^1$ represents a branched or unbranched alkyl group with 1 to 4 carbon atoms;

$R^2$ represents a branched or unbranched alkyl group with 1 to 7 carbon atoms which may optionally also be substituted by a hydroxy group at its second to seventh carbon atom, or a cycloalkyl or cycloalkylmethyl group with 3 to 7 carbon atoms in the ring, whilst the cycloalkyl ring may optionally also be substituted by a hydroxy group;

$R^1$ and $R^2$ may, however, also form, together with the nitrogen atom between them, a 4- to 7-membered saturated, monocyclic, heterocyclic ring which may optionally be interrupted by an oxygen atom or by the N—CH$_3$ group;

$R^3$ is an alkyl group with 1 to 4 carbon atoms, a chlorine atom or a hydrogen atom;

$R^4$ represents a hydrogen atom or a methyl group;

$R^5$ and $R^6$ each represent a hydrogen atom, a fluorine, chlorine or bromine atom or an alkyl group with 1 to 4 carbon atoms;

$R^7$ represents a hydrogen or chlorine atom or a methyl group;

$R^8$ represents a hydrogen atom or an alkyl group with 1 to 4 carbon atoms;

$R^9$ represents a hydrogen or halogen atom or an alkyl group with 1 to 4 carbon atoms;

$R^{10}$ represents a hydrogen atom or a methyl group and $R^{12}$ represents a branched or unbranched alkyl group with 1 to 6 carbon atoms.

If ⟩ Ⓑ represents the divalent group T and $R^7$ is a hydrogen atom, $R^3$ cannot represent a chlorine atom and Z cannot represent a sulphur atom.

Preferred compounds of general formula I above are those wherein $X^1$ represents a =CH— group, $X^2$ either represents a nitrogen atom and ⓑ represents the divalent group S, with the proviso that $R^3$, $R^4$ and $R^5$ are hydrogen atoms and $R^6$ is a hydrogen atom, a chlorine or bromine atom or a methyl or ethyl group in the 8 or 9 position of the heterocycle, or it is a =CH— group, if ⓑ assumes the meaning of the divalent group U, whilst $R^8$ is a hydrogen atom and $R^9$ is a methyl group;

$A^1$ is a 1,2-ethylene group;

$A^2$ is a straight-chained alkylene group with 1 to 5 carbon atoms;

Z is a methylene group;

R is a hydrogen atom and $R^1$ and $R^2$ represent alkyl groups with 1 to 3 carbon atoms or together with the nitrogen atom between them they represent the piperidinyl group.

The compounds of formula I may also occur in the form of their physiologically acceptable salts after reaction with organic or inorganic acids. Suitable acids include, for example, hydrochloric, hydrobromic, sulphuric, methylsulphuric, phosphoric, tartaric, fumaric, citric, maleic, succinic, gluconic, malic, p-toluenesulphonic, methanesulphonic or amidosulphonic acid or cyclohexanesulphaminic acid.

The following compounds may be mentioned as examples to illustrate the invention:

5,11-dihydro-11-[[[2-[2-[(diethylamino)methyl]-piperidin-1-yl]ethyl]amino]carbonyl]-6H-pyrido[2,3-b][1,4]benzodiazepin-6-one 5,11-dihydro-11-[[[2-[2-[[bis-(methylethyl)amino]methyl]-piperidin-1-yl]ethyl]amino]carbonyl]-6H-pyrido[2,3-b][1,4]benzodiazepin-6-one 5,11-dihydro-11-[[[2-[2-[[bis-(2-methylpropyl)amino]-methyl]-piperidin-1-yl]ethyl]amino]carbonyl]-6H-pyrido[2,3-b][1,4]benzodiazepin-6-one 5,11-dihydro-11-[[[2-[2-[(piperidin-1-yl)methyl]piperidin-1-yl]ehtyl]amino]carbonyl]-6H-pyrido[2,3-b][1,4]benzodiazepin-6-one hydrochloride 5,11-dihydro-11-[[[2-[2-[(pyrrolidin-1-yl)methyl]-piperidin-1-yl]ethyl]amino]carbonyl]-6H-pyrido[2,3-b][1,4]benzodiazepin-6-one 5,11-dihydro-11[[[2-[2-[(hexahydro-1H-azepin-1-yl)methyl]-piperidin-1-yl]ethyl]amino]carbonyl]-6H-pyrido[2,3-b][1,4]benzodiazepin-6-one 5,11-dihydro-11-[[[2-[2-[(morpholin-4-yl)methyl]-piperidin-1-yl]ethyl]amino]carbonyl]-6H-pyrido[2,3-b][1,4]benzodiazepin-6-one 5,11-dihydro-11-[[[2-[2-[(tetrahydro-4H-1,4-thiazin-4-yl)-methyl]-piperidin-1-yl]ethyl]amino]carbonyl]-6H-pyrido[2,3-b][1,4]benzodiazepin-6-one 5,11-dihydro-11-[[[2-[2-[(diethylamino)methyl]-piperidin-1-yl]-1,1-dimethyl-ethyl]amino]carbonyl]-6H-pyrido[2,3-b][1,4]benzodiazepin-6-one 5,11-dihydro-11-[[[2-[2-[(diethylamino)methyl]-piperidin-1-yl]-2,2-dimethyl-ethyl]amino]carbonyl]-6H-pyrido[2,3-b][1,4]benzodiazepin-6-one 5,11-dihydro-11-[[[3-[2-[(diethylamino)methyl]-piperidin-1-yl]propyl]amino]carbonyl]-6H-pyrido[2,3-b][1,4]benzodiazepin-6-one 5,11-dihydro-11-[[[2-[2-[(dimethylamino)methyl]-piperidin-1-yl]ethyl]amino]carbonyl]-6H-pyrido[2,3-b][1,4]benzodiazepin-6-one 5,11-dihydro-11-[[[3-[2-[(dimethylamino)methyl]-piperidin-1-yl]propyl]amino]carbonyl]-6H-pyrido[2,3-b][1,4]benzodiazepin-6-one 11-[[[2-[2-[2-(diethylamino)ethyl]-piperidin-1-yl]ethyl]amino]carbonyl]-5,11-dihydro-6H-pyrido[2,3-b][1,4]benzodiazepin-6-one 11-[[[2-[2-[3-(diethylamino)propyl]-piperidin-1-yl]ethyl]amino]carbonyl]-5,11-dihydro-6H-pyrido[2,3-b][1,4]benzodiazepin-6-one 5,11-dihydro-11-[[[2-[2-[3-(dimethylamino)propyl]-piperidin-1-yl]ethyl]amino]carbonyl]-6H-pyrido[2,3-b][1,4]benzodiazepin-6-one (R,S)-11-[[[2-[2-[(diethylamino)methyl]-pyrrolidin-1-yl]-ethyl]amino]carbonyl]-5,11-dihydro-6H-pyrido[2,3-b][1,4]benzodiazepin-6-one (R,S)-5,11-dihydro-11-[[[2-[2-[(dipropylamino)methyl]-pyrrolidin-1-yl]ethyl]amino]carbonyl]-6H-pyrido[2,3-b][1,4]benzodiazepin-6-one D,L-11-[[[4-[2-[(diethylamino)methyl]-piperidin-1-yl]butyl]amino]carbonyl]-5,11-dihydro-6H-pyrido[2,3-b][1,4]benzodiazepin-6-one D,L-5,11-dihydro-11-[[[2-[2-[2-(dimethylamino)ethyl]-piperidin-1-yl]ethyl]amino]carbonyl]-6H-pyrido[2,3-b][1,4]benzodiazepin-6-one D,L-11-[[[2-[2-[(diethylamino)methyl]-piperidin-1-yl]ethyl]methylamino]carbonyl]-5,11-dihydro-6H-pyrido[2,3-b][1,4]benzodiazepin-6-one D,L-5,11-dihydro-11-[[[2-[2-[(dimethylamino)methyl]-piperidin-1-yl]ethyl]methylamino]carbonyl]-6H-pyrido[2,3-b][1,4 benzodiazepin-6-one (R,S)-11-[[[6-[2-[(diethylamino)methyl]-piperidin-1-yl]hexyl]amino]carbonyl]-5,11-dihydro-6H-pyrido[2,3-b][1,4]benzodiazepin-6-one trans-5,11-dihydro-11-[[[2-[2-[[(4-hydroxycyclohexyl)-methylamino]methyl]-piperidin-1-yl]ethyl]methylamino]carbonyl]-6H-pyrido[2,3-b][1,4]benzodiazepin-6-one 5,11-dihydro-11-[[[2-[3-[3-(piperidin-1-yl)propyl]-piperidin-1-yl]ethyl]amino]carbonyl]-6H-pyrido[2,3-b][1,4]benzodiazepin-6-one (R,S)-11-[[[2-[2-[2-(diethylamino)ethyl]-pyrrolidin1-yl]ethyl]amino]carbonyl]-5,11-dihydro-6H-pyrido[2,3-b][1,4]benzodiazepin-6-one D,L-11-[[[2-[2-[2-(diethylamino)ethyl]-piperidin-1-yl]ethyl]methylamino]carbonyl]-5,11-dihydro-6H-pyrido[2,3-b][1,4]benzodiazepin-6-one D,L-5,11-dihydro-11-[[[4-[2-[(dimethylamino)methyl]-piperidin-1-yl]butyl]amino]carbonyl]-6H-pyrido[2,3-b][1,4]benzodiazepin-6-one trans-D,L-5,11-dihydro-11-[[[2-[2-[[(4-hydroxycyclohexyl)methylamino]methyl]-piperidin-1-yl]ethyl]amino]carbonyl]-6H-pyrido[2,3-b][1,4]benzodiazepin-6-one 9-chloro-11-[[[2-[2-[(diethylamino)methyl]-piperidin-1-yl]ethyl]amino]carbonyl]-5,11-dihydro-6H-pyrido[2,3-b][1,4]benzodiazepin-6-one 5,11-dihydro-11-[[[2-[2-[2-(dimethylamino)ethyl]-piperidin-1-yl]ethyl]methylamino]carbonyl]-6H-pyrido[2,3-b ][1,4]benzodiazepin-6-one 11-[[[2-[2-[(diethylamino)methyl]-piperidin-1-yl]ethyl]amino]carbonyl]-5,11-dihydro-8-methyl-6H-pyrido[2,3-b][1,4]benzodiazepin-6-one D,L-5,11-dihydro-11-[[[4-[2-[(dimethylamino)methyl]-piperidin-1-yl]butyl]methylamino]carbonyl]-6H-pyrido[2,3-b][1,4]benzodiazepin-6-one 5,11-dihydro-11-[[[2-[3-[(piperidin-1-yl)methyl]-piperidin-1-yl]ethyl]amino]carbonyl]-6H-pyrido[2,3-b][1,4]-benzodiazepin-6-one dihydrochloride 11-[[[2-[3-[(diethylamino)methyl]-morpholin-4-yl]ethyl]amino]carbonyl]-5,11-dihydro-6H-pyrido[2,3-b][1,4]benzodiazepin-6-one 5,11-dihydro-11-[[[2-3-[(piperidin-1-yl)methyl]-morpholine-4-yl]ethyl]amino]carbonyl]-6H-pyrido[2,3-b][1,4]benzodiazepin-6-one 11-[[[4-[2-[(diethylamino)methyl]-piperidin-1-yl]butyl]methylamino]carbonyl]-5,11-dihydro-6H-pyrido[2,3-b][1,4]benzodiazepin-6-one 5,11-dihydro-11-[[[2-2-[(dipropylamino)methyl]-piperidin-1-yl]ethyl]amino]carbonyl]-6H-pyrido[2,3-b][1,4]-benzodiazepin-6-one 8-chloro-11-[[[2-[2-[(diethylamino)methyl]-piperidin-1-yl]ethyl]amino]carbonyl]-5,11-dihydro-6H-pyrido[2,3-b][1,4]benzodiazepin-6-one 11-[[[2-[2-[(diethylamino)methyl]-piperidin-1-yl]ethyl]amino]carbonyl]-8-ethyl-6H-pyrido[2,3-b ][1,4]benzodiazepin-6-one 8-bromo-11-[[[2-[2-[(diethylamino)methyl]-piperidin-1-yl]-ethyl]amino]carbonyl]-5,11-dihydro-6H-pyrido[2,3-b][1,4]benzodiazepin-6-one 11-[[[2-[2-[(diethylamino)methyl]-piperidin-1-yl]ethyl]amino]cabonyl]-5,11-dihydro-7-fluoro-6H-pyrido[2,3-b][1,4]benzodiazepin-6-one 11-[[[2-[2-[(diethylamino)methyl]-piperidin-1-yl]ethyl]amino]carbonyl]-5,11-dihydro-8-fluoro-6H-pyrido[2,3-b][1,4]benzodiazepin-6-one 11-[[[2-[2-[(diethylamino)methyl]-piperidin-1-yl]ethyl]amino]carbonyl]-5,11-dihydro-9-fluoro-6H-pyrido[2,3-b][1,4]benzodiazepin-6-one 11-[[[2-[2-[(diethylamino)methyl]-piperidin-1-yl]ethyl]amino]carbonyl]-5,11-dihydro-10-fluoro-6H-pyrido[2,3-b][1,4 benzodiazepin-6-one 11-[[[2-[2-[(diethylamino)methyl]-piperidin-1-yl]ethyl]amino]carbonyl]-5,11-dihydro-9-methyl-6H-pyrido[2,3-b][1,4]benzodiazepin-6-one 11-[[[2-[2-[4-(diethylamino)butyl]-piperidin-1-yl]ethyl]amino]carbonyl]-5,11-dihydro-6H-pyrido[2,3-b][1,4]benzodiazepin-6-one 6,11-dihydro-11-[[[2-[2-[(dipropylamino)methyl]-piperidin-1-yl]ethyl]amino]carbonyl]-5H-pyrido[2,3-b][1,5]benzodiazepin-5-one 11-[[[2-[2-[(diethylamino)methyl]-piperidin-1-yl]ethyl]amino]carbonyl]-6,11-dihydro-5H-pyrido[2,3-b ][1,5]benzodiazepin-5-one 5,11-dihydro-11-[[[2-[2-[4-(piperidin-1-yl)butyl]piperidin-1-yl]ethyl]amino]carbonyl]-6H-pyrido[2,3-b][1,4]benzodiazepin-6-one 2-chloro-11-[[[2-[2-[(diethylamino)methyl]-piperidin-1-yl]ethyl]amino][carbonyl]-5,11-dihydro-6H-pyrido[2,3-b][1,4]benzodiazepin-6-one 11-[[[2-[2-[(diethylamino)methyl]-piperidin-1-yl]ethyl]amino]carbonyl]-5,11-dihydro-2-methyl-6H-pyrido[2,3-b][1,4]benzodiazepin-6-one 11-[[[2-[2-[(diethylamino)methyl]-piperidin-1-yl]ethyl]amino]carbonyl]-5,11-dihydro-2,4,8-trimethyl-6H-pyrido[2,3-b][1,4]benzodiazepin-6-one 5-[[[2-2-[(diethylamino)methyl]-piperidin-1-yl]ethyl]amino]carbonyl]-5,11-dihydro-10H-pyrido[3,2-b][1,4]benzodiazepin-10-one 5,11-dihydro-5-[[[2-2-[(dipropylamino)methyl]-piperidin-1-yl]ethyl]amino]carbonyl]-10H-pyrido[3,2-b][1,4]benzodiazepin-10-one 4-[[[2-[2-[(diethylamino)methyl]-piperidin-1-yl]ethyl]amino]carbonyl]-1-methyl-1,4,9,10-tetrahydropyrazolo[4,3-e]pyrido[3,2-b][1,4]diazepin-10-one 4-[[[2-[2-[(diethylamino)methyl]-piperidin-1-yl]ethyl]amino]carbonyl]-1,3-dimethyl-1,4,9,10-tetrahydropyrazolo[4,3-e]pyrido[3,2-b][1,4]diazepin-10-one 4-[[[2-[2-[(dipropylamino)methyl]-piperidin-1-yl]ethyl]amino]carbonyl]-1-methyl-1,4,9,10-tetrahydropyrazolo[4,3-e]pyrido[3,2-b][1,4]diazepin-10-one 4-[[[2-[2-[(diethylamino)methyl]-piperidin-1-yl]ethyl]amino]carbonyl]-1,3-dimethyl-1,4,9,10-tetrahydropyrazolo[4,3-b][1,5]benzodiazepin-10-one 4-[[[2-[2-[(diethylamino)methyl]-piperidin-1-yl]ethyl]amino]carbonyl]-1-methyl-1,4,9,10-tetrahydropyrazolo[4,3-b][1,5]benzodiazepin-10-one 11-[[[2-[2-[[(cyclopentyl)methylamino]methyl]-piperidin-1-yl]ethyl]amino]carbonyl]-5,11-dihydro-6H-pyrido[2,3-b][1,4]benzodiazepin-6-one 11-[[[2-[3-(diethylamino)-hexahydro-1H-azepin-1-yl]ethyl]amino]carbonyl]-5,11-dihydro-6H-pyrido[2,3-b][1,4]benzodiazepin-6-one 11-[[[2-[3-[(diethylamino)methyl]-piperidin-1-yl]ethyl]amino]carbonyl]-5,11-dihydro-6H-pyrido[2,3-b][1,4]benzodiazepin-6-one 5,11-dihydro-11-[[[2-[3-[(dipropylamino)methyl]-piperidin-1-yl]ethyl]amino]carbonyl]-6H-pyrido[2,3-b][1,4]benzodiazepin-6-one 5,11-dihydro-11-[[[2-[3-[(hexahydro-1H-azepin-1-yl)methyl]-piperidin-1-yl]ethyl]amino]carbonyl]-6H-pyrido[2,3-b][1,4]benzodiazepin-6-one 9-chloro-11-[[[2-[3-[(diethylamino)methyl]-piperidin-1-yl]-ethyl]amino]carbonyl]-5,11-dihydro-6H-pyrido[2,3-b][1,4]benzodiazepin-6-one 11-[[[2-[4-[(diethylamino)methyl]-piperidin-1-yl]ethyl]amino]carbonyl]-5,11-dihydro-6H-pyrido[2,3-b][1,4]benzodiazepin-6-one 5,11-dihydro-11-[[[2-[4-[2-(piperidin-1-yl)ethyl]-piperidin-1-yl]ethyl]amino]carbonyl]-6H-pyrido[2,3-b][1,4]benzodiazepin-6-one hydrochloride 11-[[[2-[4-[2-(diethylamino)ethyl]-piperidin-1-yl]ethyl]amino]carbonyl]-5,11-dihydro-6H-pyrido[2,3-b][1,4]benzodiazepin-6-one 11-[[[2-[4-[3-(diethylamino)propyl]-piperidin-1-yl]ethyl]amino]carbonyl]-5,11-dihydro-6H-pyrido[2,3-b][1,4]benzodiazepin-6-one 5,11-dihydro-11-[[[2-[2-[(dipropylamino)methyl]-morpholin-4-yl]ethyl]amino]carbonyl]-6H-pyrido[2,3-b][1,4]benzodiazepin-6-one 5-[[[2-[2-[(diethylamino)methyl]-piperidin-1-yl]ethyl]amino]carbonyl]-5,10-dihydro-11H-dibenzo[b,e][1,4]diazepin-11-one 5,10-dihydro-5-[[[3-[2-[(dimethylamino)methyl]-piperidin-1-yl]propyl]amino]carbonyl]-11H-dibenzo[b,e][1,4]diazepin-11-one 5-[[[3-[2-[(diethylamino)methyl]-piperidin-1-yl]propyl]amino]carbonyl]-5,10-dihydro-11H-dibenzo[b,e][1,4]diazepin-11-one 5,10-dihydro-5-[[[2-[2-[(dimethylamino)methyl]-piperidin-1-yl]ethyl]amino]carbonyl]-11H-dibenzo[b,e][1,4]diazepin-11-one (±)-5-[[[2-[2-[(diethylamino)methyl]-pyrrolidin-1-yl]ethyl]amino]carbonyl]-5,10-dihydro-11H-dibenzo[b,e][1,4]diazepin-11-one 4-[[[2-[2-[(diethylamino)methyl]-piperidin-1-yl]ethyl]amino]carbonyl]-4,9-dihydro-3-methyl-10H-thieno[3,4-b][1,5]benzodiazepin-10-one 4,9-dihydro-4-[[[2-[2-[(pyrrolidin-1-yl)methyl]-piperidin-1-yl]ethyl]amino]carbonyl]-3-methyl-10H-thieno[3,4-b][1,5]benzodiazepin-10-one 3-chloro-4-[[[2-[2-[(diethylamino)methyl]-piperidin-1-yl]ethyl]amino]carbonyl]-4,9-dihydro-10H-thieno[3,4-b][1,5]benzodiazepin-10-one 1,3-dimethyl-4-[[[2-[2-[(diethylamino)methyl]-piperidin-1-yl]ethyl]amino]carbonyl]-4,9-dihydro-10H-thieno[3,4-b][1,5]benzodiazepin-10-one 1,3-dimethyl-4-[[[2-[2-[(dimethylamino)methyl]-piperidin-1-yl]ethyl]amino]carbonyl]-4,9-dihydro-10H-thieno[3,4-b][1,5]benzodiazepin-10-one (+)-5,11-dihydro-11-[[[2-[2[(diethylamino)methyl]-piperidin-1-yl]ethyl]amino]carbonyl]-6H-pyrido[2,3-b][1,4]benzodiazepin-6-one (−)-5,11-dihydro-11-[[[2-[2-[(diethylamino)methyl]-piperidin-1-yl]ethyl]amino]carbonyl]-6H-pyrido[2,3-b][1,4]benzodiazepin-6-one (+)-4-[[[2-[2-[(diethylamino)methyl]-piperidin-1-yl]ethyl]amino]carbonyl]-4,9-dihydro-3-methyl-10H-thieno[3,4-b][1,5]benzodiazepin-10-one (−)-4-[[[2-[2-[(diethylamino)methyl]-piperidin-1-yl]ethyl]amino]carbonyl]-4,9-dihydro-3-methyl-10H-thieno[3,4-b][1,5]benzodiazepin-10-one (+)-9-chloro-11-[[[2-[2-[(diethylamino)methyl]-piperidin-1-yl]ethyl]amino]carbonyl]-5,11-dihydro-6H-pyrido[2,3-b][1,4]benzodiazepin-6-one (−)-9-chloro-11-[[[2-[2-[(diethylamino)methyl]-piperidin-1-yl]ethyl]amino]carbonyl]-5,11-dihydro-6H-pyrido[2,3-b][1,4]benzodiazepin-6-one 1,3-dimethyl-4-[[[2-[2-[(dipropylamino)methyl]-piperidin-1-yl]ethyl]amino]carbonyl]-1,4,9,10-tetrahydropyrrolo[3,2-b][1,5]benzodiazepin-10-one 1,3-dimethyl-4-[[[2-[2-[(hexahydro-1H-azepin-1-yl)methyl]-piperidin-1-yl]ethyl]amino]carbonyl]-1,4,9,10-tetrahydropyrrolo[3,2-b][1,5]benzodiazepin-10-one 5-chloro-4-[[[2-[2-[(diethylamino)methyl]-piperidin-1-yl]-ethyl]amino]carbonyl]-1,3-dimethyl-1,4,9,10-tetrahydropyrrolo[3,2-b][1,5]benzodiazepin-10-one 3-chloro-1-methyl-4-[[[2-[2-[(dipropylamino)methyl]-piperidin-1-yl]ethyl]amino]carbonyl]-1,4,9,10-tetrahydropyrrolo[3,2-b][1,5]benzodiazepin-10-one 1-methyl-4-[[[2-[2-[(dipropylamino)methyl]-piperidin-1-yl]ethyl]amino]carbonyl]-1,4,9,10-tetrahydropyrrolo[3,2-b][1,5]benzodiazepin-10-one 4-[[[2-[2-[(dibutylamino)methyl]-piperidin-1-yl]ethyl]amino]carbonyl]-1-methyl-1,4,9,10-tetrahydro-pyrrolo[3,2-b][1,5]benzodiazepin-10-one 6-chloro-5-[[[2-[2-[(diethylamino)methyl]-piperidin-1-yl]ethyl]amino]carbonyl]-5,10-dihydro-11H-dibenzo[b,e][1,4]diazepin-11-one According to the invention, the new basically substituted condensed diazepinones of general formula I are obtained by the following processes:

(a) Basically substituted condensed diazepinones of general formula Ia

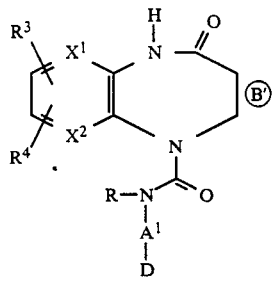
(Ia)

wherein R, $R^3$, $R^4$, $X^1$, $X^2$, $A^1$ and D are defined as hereinbefore and ⒷB represents one of the divalent groups S, U, V, W, or T′

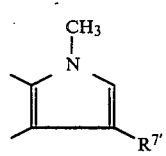
(T′)

wherein $R^{7'}$ is a chlorine atom or a methyl group, are obtained by reacting carbonic acid derivatives of general formula II

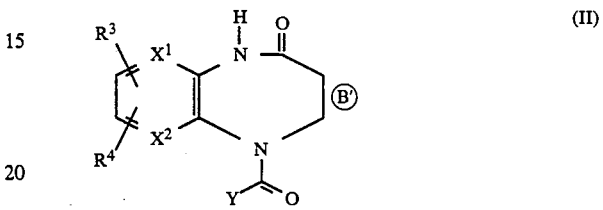
(II)

wherein $R^3$, $R^4$, ⒷB, $X^1$ and $X^2$ are defined as hereinbefore and

Y represents a halogen atom, preferably a bromine or chlorine atom, or the group $OR^{11}$, wherein $R^{11}$ represents an optionally halogen substituted alkyl group with 1 to 5 carbon atoms, a phenyl group optionally substituted by halogen atoms or nitro groups or an aralkyl group with 7 to 15 carbon atoms, with compounds of general formula III

(III)

wherein

R, $A^1$ and D are defined as hereinbefore.

The reaction is carried out without or preferably in the presence of solvents such as water, toluene or alcohols such as methanol, ethanol or isopropanol, but preferably in the presence of aprotic polar solvents, e.g. tetrahydrofuran, 1,4-dioxane, acetonitrile, N,N-dimethylformamide, dimethylsulphoxide, hexamethylphosphoric acid triamide or mixtures thereof and at temperatures of between −10° C. and the boiling point of the reaction mixture, preferably between 40° and 100° C. It has proved satisfactory to use additional organic or inorganic bases, e.g. alkali or alkaline earth metal hydroxides, alkoxides or carbonates, such as sodium hydroxide, sodium methoxide, potassium tert.butoxide, sodium carbonate, potassium carbonate; tertiary amines such as triethylamine, ethyl diisopropylamine, N,N-dimethylaniline, pyridine or 4-(dimethylamino)pyridine; and to carry out the reaction in the presence of an excess of a compound of general formula III.

The reaction may, however, also be carried out with a metal compound of general formula IIIa,

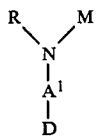 (IIIa)

wherein
M represents an alkali metal atom or 1 equivalent of an alkaline earth metal atom. Metal compounds of general formula IIIa may easily be prepared in situ from III by reacting with alkali or alkaline earth metals, e.g. sodium, potassium or barium, or with alkali or alkaline earth metal hydrides, e.g. sodium, potassium or calcium hydride, or by reaction with alkali organometals or alkaline earth organometals, e.g. with n-butyl-lithium or phenyl-lithium.

(b) Basically substituted condensed diazepinones of general formula Ia may also be obtained by reacting tricyclic compounds of general formula IV

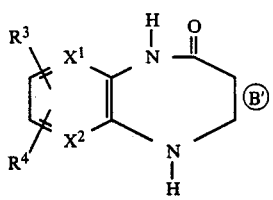 (IV)

wherein the groups $R^3$, $R^4$, $X^1$, $X^2$ and Ⓑ are defined as hereinbefore, with a chlorocarbonic acid derivative of general formula V

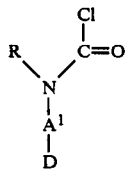 (V)

or—if in the compounds of general formula Ia R represents a hydrogen atom—an isocyanate of general formula Va $$O=C=N-A^1-D \qquad (Va)$$

wherein the groups R, $A^1$ and D are defined as hereinbefore.

The reaction is preferably carried out in inert organic solvents, e.g. in aromatic hydrocarbons such as toluene, xylene, in ethers such as diisopropylether, tetrahydrofuran or dioxane, in ketones such as pentan-3-one, in chlorinated aliphatic hydrocarbons such as 1,2-dichloroethane or in other solvents such as acetonitrile or dimethylformamide or in mixtures thereof, optionally in the presence of tertiary organic bases such as pyridine and at temperatures up to the boiling point of the reaction mixture, preferably at temperatures of between +30° and +100° C.

(c) The new pyrrolo-condensed diazepinones of general formula Ib which come under general formula I

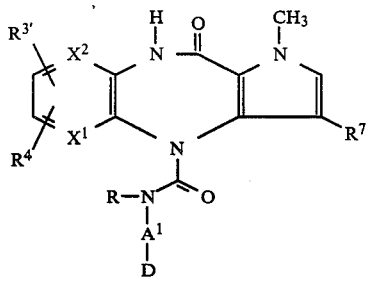 (Ib)

wherein
$R^4$, $X^1$, $X^2$, $A^1$ and D are defined hereinbefore,
$R^{3'}$ represents an alkyl group with 1 to 4 carbon atoms or a hydrogen atom and
$R^7$ represents a hydrogen atom and for the group

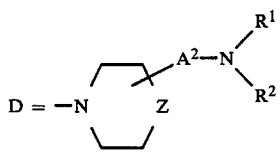

Z has the meanings given before with the exception of a sulphur atom, and $R^1$, $R^2$ and $A^2$ are defined as hereinbefore, may also be prepared by hydrogenolysis from compounds of general formula Ib wherein $R^7$ represents a chlorine atom.

The hydrogenolysis is carried out in the presence of catalysts of metals from the VIIIth sub-group of the periodic table of elements, for example palladium on animal charcoal, palladium on barium sulphate, Raney nickel or Raney cobalt and under hydrogen pressures of from 1 to 300 bar and temperatures from 0° C. to 130° C. in the presence of solvents, e.g. alcohols such as methanol, ethanol; ethers such as dioxane, tetrahydrofuran, carboxylic acids, e.g. acetic acid or tertiary amines, e.g. triethylamine. If the work is done in the absence of any additional hydrogen chloride acceptors, for example sodium carbonate, potassium hydrogen carbonate, triethylamine or sodium acetate, the hydrochlorides of the desired compounds are formed directly and may be isolated after the removal of the catalyst by evaporating the reaction solution. If in the hydrogenolysis reaction described above the hydrogen is replaced by formic acid, the reaction will in theory also take place under pressure-free conditions. In this alternative form, it has proved particularly useful to carry out the reaction with formic acid in the presence of dimethylformamide as solvent and palladium on charcoal as catalyst at temperatures of between 70° and 100° C., and to carry out the reduction with triethylammonium formate in the presence of excess triethylamine and palladium on animal charcoal or palladium acetate and triarylphosphines such as triphenylphosphine, tris-(o-tolyl)-phosphine, tris-(2,5-diisopropylphenyl)phosphine, a temperatures between 40° and 100° C.

(d) Basically substituted condensed diazepinones of general formula Ia

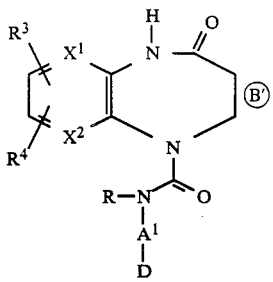

(Ia)

wherein
R, R³, R⁴, X¹, X², A¹ and D are defined as hereinbefore and 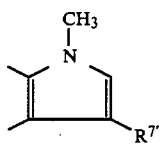 represents one of the divalent groups S, U, V, W or T'

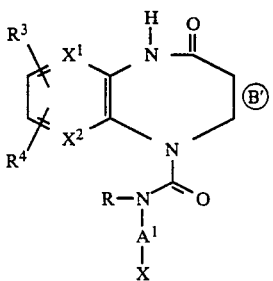

(T')

wherein R⁷' is a chlorine atom or a methyl group, are obtained by reacting condensed diazepinones of general formula VIII

(VIII)

wherein
R, R³, R⁴, X¹, X² and A¹ are defined as hereinbefore and ] ⓑ is defined as hereinbefore and X represents a nucleofugal group, for example a chlorine, bromine or iodine atom, an alkanesulphonyloxy, arenesulphonyloxy, trifluoromethanesulphonyloxy or hydroxy group, with diamines of general formula IIIc, H—D (IIIc)

wherein D is defined as hereinbefore.

The amination is carried out in an inert solvent at temperatures between −10° C. and the boiling temperature of the solvent, preferably either with at least 2 moles of secondary amine of general formula IIIc or with 1 to 2 moles of a secondary amine of general formula IIIc and an auxiliary base. Suitable solvents include, for example, chlorinated hydrocarbons such as methylene chloride, chloroform or dichloroethane; open-chained or cyclic ethers such as diethylether, tetrahydrofuran or dioxane; aromatic hydrocarbons such as benzene, toluene, xylene, chlorobenzene or pyridine; alcohols such as ethanol or isopropanol; ketones such as acetone; acetonitrile, dimethylformamide or 1,3-dimethyl-2-imidazolidinone. Examples of auxiliary bases include tertiary organic bases such as triethylamine, N-methyl-piperidine, diethylaniline, pyridine and 4-(dimethylamino)pyridine or inorganic bases such as alkali metal or alkaline earth metal carbonates or hydrogen carbonates, hydroxides or oxides. If desired, the reaction may be accelerated by the addition of alkali metal iodides. The reaction times range from 15 minutes to 80 hours depending on the nature and quantity of the amine of general formula IIIc used. If only 1 mol of the secondary amine of general formula IIIc is used to 1 mol of a compound of general formula VIII in this reaction, the monohydrochloride, monohydrobromide, monohydroiodide, tosylate or mesylate of the desired compound of general formula Ia is obtained directly, if X in general formula VIII represents, for example, a chlorine, bromine or iodine atom or a p-toluenesulphonyloxy or methanesulphonyloxy group.

If in general formula VIII X is the hydroxy group, the work is conveniently done in the presence of catalysts from the VIIIth sub-group of the periodic table of elements, for example palladium black or Raney nickel, and using aprotic inert solvents, for example open-chained or cyclic ethers such as diethylether, tetrahydrofuran or dioxane, aromatic hydrocarbons such as benzene, toluene, xylene or pyridine, acetonitrile, dimethylformamide or 1,3-dimethyl-2-imidazolidinone or using excess secondary amine of general formula IIIc as solvent. Reactions in the presence of Raney nickel may advantageously also be carried out using aluminium tert.butoxide as co-catalyst. In compounds of general formula VIII wherein X represents the hydroxy group, this function may be activated in known manner by conversion into suitable alkoxyphosphonium salts, for example by reacting with tetrachloromethane and hexamethylphosphoric acid triamide, which after subsequent treatment with ammonium perchlorate yields the corresponding isolatable alkoxyphosphonium perchlorates

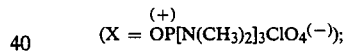

further reaction with secondary amines of general formula IIIc yields the basically substituted diazepinones of general formula Ia sought. A particularly advantageous alternative form of activation of the alcoholic hydroxyl in compounds of general formula VIII wherein X represents the hydroxy group consists in successive reaction with sodium hydride in benzene or dimethylformamide, then with (N-methyl-N-phenylamino) triphenylphosphonium iodide and a secondary amine of general formula IIIc; in this procedure there is no need to isolate the phosphonium salt which is formed as an intermediate or to use perchlorates.

Bases of general formula I thus obtained may subsequently be converted into their acid addition salts or if acid addition salts are obtained they may be converted into the free bases or other pharmacologically acceptable acid addition salts.

The aminoacylated condensed diazepinones of general formula I according to the invention generally contain an asymmetric carbon atom in the side chain. These compounds may therefore occur both as enantiomeric (+) and (−) forms. The invention includes the individual isomers as well as the racemates thereof.

Any racemates of the compounds of general formula I may be resolved by known methods, for example using an optically active acid such as (+) or (−) tartaric acid or a derivative thereof such as (+) or (−)

diacetyl tartaric acid, (+) or (−) monomethyltartrate or (+) camphorsulphonic acid.

According to a conventional method of isomer separation the racemate of a compound of general formula I is reacted with one of the above mentioned optically active acids in equimolar quantities in a solvent and the crystalline diastereomeric salts obtained are separated on the basis of their different solubilities. This reaction may be carried out in any kind of solvent provided that it shows a sufficient difference in the solubility of the salt. Preferably, methanol, ethanol or mixtures thereof, for example in a ratio by volume of 50:50 may be used. Each of the diastereomeric salts is then dissolved in water, neutralised with a base such as sodium hydroxide or potassium hydroxide and the corresponding free compound is obtained in (+) or (−) form.

Only one enantiomer is obtained if the methods of synthesis described above are carried out with only one enantiomer of general formula IIIa, V or IIIc.

The carbonic acid derivatives of general formula II required as intermediate products are obtained analagously to DE-A-3204169, DE-A-3204158 and DE-A-3204401 by reacting tricyclic compounds of general formula IV with a halocarbonic acid derivative of general formula VI

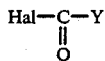
(VI)

wherein Hal represents a bromine or chlorine atom, preferably chlorine atom and Y is defined as hereinbefore.

The reaction is carried out in inert organic solvents, for example aromatic hydrocarbons such as toluene, chlorobenzene or xylene; open chained or cyclic ethers such as diisopropylether, tetrahydrofuran or dioxane, open chained or cyclic aliphatic ketones, for example pentan-3-one; chlorinated aliphatic hydrocarbons such as 1,2-dichloroethane or other solvents such as acetonitrile or dimethylformamide or in mixtures thereof and preferably in the presence of tertiary organic bases, preferably pyridine, and at temperatures up to at most the boiling point of the solvent or mixture of solvents used, preferably between +30° and +80° C.

The starting compounds of general formula III which are new may be prepared by a number of methods, of which the following are preferred:

(a) reduction of carboxylic acid amides of general formula IIIb

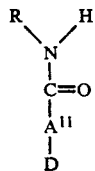
(IIIb)

wherein R and D are defined as hereinbefore and $A^{11}$ is a straight chained or branched saturated alkylene group with up to 6 carbon atoms which differs from the corresponding group $A^1$ by the absence of a methylene group.

As the reducing agent, metal hydride and complex hydrides are preferred which are known to have good reducing qualities compared with primary and secondary aliphatic carboxylic acid amides. Suitable reducing agents include, for example: lithium aluminium hydride in ethereal solvents such as diethylether, tetrahydrofuran, dioxane or diethylene glycol dimethylether (see for example N. G. Gaylord "Reduction with Complex Metal Hydrides", Interscience Publishers Inc., New York, N.Y. 1956; W. G. Brown, Org. Reactions 6, 469 (1951); R. F. Nystrom und W. G. Brown, J. Am. Chem. Soc. 69, 2548 (1947)); aluminium hydride in tetrahydrofuran (analogously to H. C. Brown and N. M. Yoon, J. Am. Chem. Soc. 88, 1464 (1966)); sodium-bis-(2-methoxyethoxy) aluminium hydride (RED-AL) in benzene, toluene or xylene (analagously to V. Bazant et al., Tetrahedron Letters 1968, 3303-3306; M. Cerny et al., Coll. Czechoslov. Chem. Commun. 34, 1033 (1969)); lithium trimethoxy-aluminium hydride in tetrahydrofuran (analagously to H. C. Brown and P. M. Weissman, J. Am. Chem. Soc. 87, 5614 (1965)); sodium borohydride in dimethylsulphoxide and in the presence of methanesulphonic acid or sulphuric acid (analagously to St. R. Wann, P. T. Thorsen and M. M. Kreevoy, J. Org. Chem. 46, 2579 (1981)); sodium borohydride in tetrahydrofuran and in the presence of ethanedithiol or thiophenol (analagously to Y. Mabi et al., Chem. Ind. 1976, 332); tetra-n-butylammoniumborohydride in boiling dichloromethane (analagously to T. Wakamatsu et al, Heterocycles 14, 1437 (1980)); sodium acyloxyborohydrides, for example sodium acetoxyborohydride or sodium trifluoroacetoxyborohydride in boiling dioxane, tetrahydrofuran or diethyleneglycoldimethylether (analagously to N. Umino et al., Tetrahedron Letters 1976, 763); diborane or borane-tetrahydrofuran complex, preferably in tetrahydrofuran as solvent (analagously to H. C. Brown and P. Heim, J. Am. Chem. Soc. 86, 3566 (1964); H. C. Brown and P. Heim, J. Org. Chem. 38, 912 (1973); Z. B. Papanastassiou and R. J. Bruni, J. Org. Chem. 29, 2870 (1964)); borane-dimethylsulphide complex in tetrahydrofuran (analagously to H. C. Brown, S. Narasimhan and Y. M. Loi, Synthesis 1981, 441, ibid. 1981, 996).

The carboxylic acid amides of general formula IIIb required may be prepared in the usual way from diamines of general formula IIIc

(IIIc)

and w-haloalkanamides of general formula VII,

(VII)

wherein R, $A^{11}$ and D are defined as hereinbefore and Hal is a chlorine, bromine or iodine atom, for example using hydrogen halide acceptors such as sodium or potassium hydrogen carbonate, sodium, potassium or barium carbonate, diisopropylamine or triethylamine and using polar protic or aprotic solvents such as methanol, ethanol, acetone, acetonitrile or dimethylformamide.

The preparation of the intermediate compounds of general formula IIIc is described in detail in DE-A-3626095. Compounds of general formula VII are known from the literature or may easily be synthesised from common starting materials using methods familiar to those skilled in the art.

(b) Reduction of nitriles of general formula IIId,

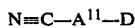
(IIId)

wherein the groups $A^{11}$ and D are defined as hereinbefore; in this alternative method intermediate compounds of general formula III are produced wherein R is a hydrogen atom. For reduction of nitriles of general formula IIId there are two preferred alternative methoes.

(1) Catalytic hydrogenation in the presence of metals of the VIIIth sub group of the periodic table of elements or the oxides thereof, e.g. Raney-nickel, Raney-cobalt, palladium on animal charcoal, palladium on barium sulphate, palladium on calcium carbonate, platinum (IV) oxide, rhodium on aluminium oxide or rhodium in the presence of lithium hydroxide. Hydrogenation may be carried out under normal pressure or at elevated hydrogen pressures up to 1000 bar and at temperatures between $-10°$ C. and $+200°$ C., the choice of hydrogenation temperature depending on the nature of the catalyst. To avoid the formation of secondary amines it is advisable to carry out hydrogenation in the presence of anhydrous ammonia. Preferred solvents are alcohols such as methanol and ethanol and ethers such as dioxane and tetrahydrofuran. In the hydrogenation of $\alpha$-aminonitriles, i.e. compounds of general formula IIId wherein $A^{11}$ represents an optionally methylated or dimethylated methylene group, it has proved particularly satisfactory to use Raney-nickel as catalyst and to work without a solvent or with non-polar solvents such as hexane of cyclohexane at temperatures between $+50°$ C. and $100°$ C. and at hydrogen pressures between 50 and 200 bar.

(2) Reaction with metal hydrides and complex hydrides. Suitable reducing agents include, for example: lithium aluminium hydride in anhydrous ethers such as diethylether, tetrahydrofuran, dioxane or diethylene glycol dimethylether, or in pyridine and N-methylmorpholine (see for example N. G. Gaylord, "Reduction with Complex Metal Hydrides", Interscience Publishers, Inc., New York, N.Y. 1956, W. G. Brown, Org. Reactions 6, 469 (1951)); lithium aluminium hydride modified by the addition of aluminium chloride (analagously to R. F. Nystrom, J. Amer. Chem. Soc. 77, 2544 (1955)); in ethers such as diethylether or tetrahydrofuran; lithium trimethoxy-aluminium hydride in tetrahydrofuran (analagously to H. C. Brown and P. M. Weissman, J. Am. Chem. Soc. 87, 5614 (1965)); aluminium hydride in tetrahydrofuran (analagously to H. C. Brown and N. M. Yoon, J. Am. Chem. Soc. 88, 1464 (1966)); tetra-n-butylammoniumborohydride in boiling dichloromethane or tetrahydrofuran (see also T. Wakamatsu et al., Heterocycles 14, 1437 (1980)); sodium borohydride in combination with aluminium chloride and using ethers, e.g. diethyleneglycoldimethylether as solvents (analagously to H. C. Brown and B. C. Subba Rao, J. Am. Chem. Soc. 78, 2582 (1956)); sodium borohydride combined with transition metal salts, e.g. cobalt (II) chloride hexahydrate, nickel (II) chloride hexahydrate, nickel (II) chloride, cobalt (II) benzoate tetrahydrate, osmium (IV) chloride, iridium (III) chloride, platinum (II) chloride in hydroxylic or hydroxyl free solvents, for example in methanol or toluene (analagously to T. Satoh et al., Tetrahedron Letters 1969, 4555); sodium trifluoroacetoxyborohydride in dioxane, tetrahydrofuran or diethyleneglycoldimethylether (analagously to N. Umino et al., Tetrahedron Letters 1976, 2875); sodium borohydride in aqueous methanol and in the presence of Raney-nickel (analagously to R. A. Egli, Helv. Chim. Acta 53, 47 (1970)); diborane or borane-tetrahydrofuran complex, preferably in tetrahydrofuran or diethyleneglycoldimethylether as solvent (analagously to H. C. Brown and B. C. Subba Rao, J. Am. Chem. Soc. 82, 681 (1960); H. C. Brown, P. Heim and N. M. Yoon, J. Am. Chem. Soc. 92, 1637 (1970)).

Nitriles of general formula IIId may easily be synthesised analagously to the process given above for carboxylic acid amides of general formula IIIb from diamines of general formula IIIc and $\omega$-haloalkanenitriles of general formula VIIa, $$\text{Hal}-A^{11}-C\equiv N \qquad \text{(VIIa)}$$

wherein Hal and $A^{11}$ are defined as hereinbefore. Nitriles of general formula VIIa are commercially available or known from the literature or may be obtained analagously to methods known from the literature. Suitable methods of synthesising aminonitriles of general formula IIId wherein $A^{11}$ represents an optionally alkylated or dialkylated methylene group also include the various alternative forms of aminonitrile synthesis according to Strecker, for example diamines of general formula IIIc may be reacted with aldehydes, e.g. aqueous formaldehyde solution, and with sodium cyanide in the presence of sodium hydrogensulphite or reacted with cyanohydrins of corresponding aldehydes or ketones in the presence of retarding agents such as benzene, toluene or xylene.

The tricyclic compounds of general formula IV are known from the patent literature or can be synthesised from common starting materials by keeping closely to published methods.

Chlorocarbonic acid derivatives of general formula V and isocyanates of general formula Va may be obtained analagously to methods known from the literature (see for example W. Sifken, Liebigs. Ann. Chem. 562, 75 (1949); Houben-Weyl 8, 117, 119; Ullmann V, 72 (1954); H. H. Saunders and R. J. Slocombe, Chem. Rev. 43, 203 (1948); R. J. Slocombe, E. E. Hardy, J. H. Saunders and R. L. Jenkins, J. Am. Chem. Soc. 72, 1888 (1950); H. Habad and A. G. Zeiler, Chem. Rev. 73, 75 (1973); H. J. Tritchett, Chem. Soc. Rev. 3, 209 (1979), R. Appel, K. Warning, K.-D. Ziehn and A. Gilak, Chem. Ber. 107, 2671-4 (1974)).

Halocarbonic acid derivatives of general formula VI are known.

The starting compounds of general formula VIII wherein X represents a chlorine, bromine or iodine atom or a hydroxy group are obtained by aminolysis of carbonic acid derivatives of general formula II

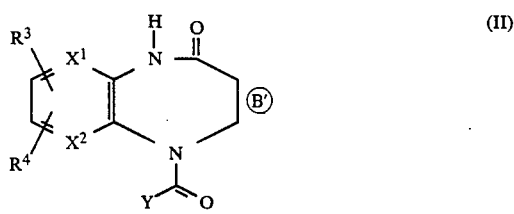

wherein, $R^3$, $R^4$, Ⓑ, $X^1$ and $X^2$ are defined as hereinbefore and

Y represents a halogen atom, preferably a bromine or chlorine atom, or the group $OR^{11}$ wherein $R^{11}$ is an optionally halogen substituted alkyl group with 1 to 5 carbon atoms, a phenyl group optionally substituted by halogen atoms or nitro groups or an aralkyl group with 7 to 15 carbon atoms, with compounds of general formula IX

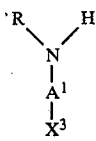

(IX)

wherein R and A¹ are defined as hereinbefore and X³ represents a chlorine, bromine or iodine atom or a hydroxy group.

The reaction is carried out without or preferably in the presence of solvents such as water, toluene or alcohols such as methanol, ethanol or isopropanol, but preferably in the presence of aprotic polar solvents, e.g. tetrahydrofuran, 1,4-dioxane, acetonitrile, N,N-dimethylformamide, dimethylsulphoxide, hexamethylphosphoric acid triamide or mixtures thereof and at temperatures of between −10° C. and the boiling point of the reaction mixture, preferably between 40° and 100° C. It has proved satisfactory to use additional organic or inorganic bases, e.g. alkali metal or alkaline earth metal hydroxides, alkoxides or carbonates, such as sodium hydroxide, sodium methoxide, potassium tert.butoxide, sodium carbonate, potassium carbonate, sodium hydrogen carbonate; tertiary amines such as triethylamine, ethyl diisopropylamine, N,N-dimethylaniline, pyridine or 4-(dimethylamino)pyridine. Compounds of general formula VIII wherein X has the meanings given above with the exception of a hydroxy group are obtained in accordance with methods known from the literature from compounds of general formula VIII wherein X is hydroxy group. For example, the compounds of general formula VIII wherein X is a hydroxy group may easily be converted, by reaction with triaryl or trialkylphosphines and tetrachloromethane, into compounds of general formula VIII wherein x represents a chlorine atom. From these compounds, in turn, the compounds of general formula VIII wherein X represents a bromine or iodine atom are obtained in conventional manner by reacting with sodium bromide or sodium iodide in suitable solvents.

Finally, compounds of general formula IX are commercially available or may easily be prepared from commercially available materials by methods known from the literature.

The invention further relates to pharmaceutical compositions containing one or more basically substituted diazepinones of general formula I or the physiologically acceptable salts thereof.

For this purpose, the compounds of general formula I may be incorporated in known manner in the conventional pharmaceutical preparations, e.g. solutions, suppositories, tablets, coated tablets, capsules or infusions. The daily dose is generally between 0.01 and 5 mg/kg, preferably between 0.02 and 2.5 mg/kg, more particularly between 0.05 and 1.0 mg/kg of body weight, optionally administered in the form of several, preferably 1 to 3 dosage units, to achieve the desired results.

The basically substituted condensed diazepinones of general formula I and the acid addition salts thereof have valuable properties; in particular, they have favourable effects on heart rate and are suitable for use as vagal pacemakers for the treatment of bradycardia and bradyarrhythmia in both human and veterinary medicine, in view of the absence of inhibiting effects on gastric acid secretion, salivation and mydriatic influences; some of the compounds also have spasmolitic properties on peripheral organs, particularly the colon and bladder.

Compounds of general formula I which are not satisfactorily resorbed owing to their poor lipophilicity are suitable for use by inhalation to treat bronchospasm, for example in asthmatic diseases; compared with the quaternary ammonium salts, for example ipratropium bromide, used hitherto for this indication, the compounds of general formula I have the advantage of greater selectivity and in particular they are virtually free from any inhibiting effects on the exocrine glands.

A favourable correlation between the tachycardiac effects on the one hand and the undesirable effects on pupil size and the secretion of tears, saliva and gastric acid, which occurs with therapeutic agents having an anticholinergic component, is of particular importance in the therapeutic use of the substances. The tests which follow show that the compounds according to the invention have surprisingly favourable correlations in this respect.

A

INVESTIGATION OF FUNCTIONAL SELECTIVITY OF THE ANTIMUSCARINIC ACTIVITY

Substances with antimuscarinic properties inhibit the effects of exogenically supplied agonists or acetylcholine which is released from cholinergic nerve endings. The following is a description of methods which are suitable for detecting cardioselective antimuscarinics.

"In vitro" organ preparations

Dissociation constants ($K_B$ values) were determined in vitro on the guinea pig ileum and spontaneously beating atrium. The ileum was removed and incubated in Krebs-Henseleit solution in an organ bath. Contractions were produced by means of increasing concentrations of methacholine (M) so that a full concentration-activity curve could be plotted. Then M was washed out, the test substance was added and kept in contact for 30 minutes and again a concentration-activity curve was plotted with M. The dissociation constant was calculated according to Arunlakshana and Schild (Brit. J. Pharmacol. 14, 48, 1959) from the dosage ratio (DR), i.e. the extent of displacement of the concentration-activity curve.

In the isolated, spontaneously beating right atrium M reduced the heart rate as a function of the concentration. This effect was stopped by the addition of an antimuscarinic. Dissociation constants for the muscarinic receptors of the atrium were obtained in the same way as described above. A comparison of the dissociation constants measured in the two different tissues made it possible to identify cardioselective substances. The results are contained in Table IV.

"In vivo" methods

The objective of the method used was to confirm the selectivity of the antimuscarinic activity. Those substances which had been selected on the basis of the "in vitro" investigations were tested for their
1. tachycardiac effect on the conscious dog,
2. $M_1/M_2$ selectivity in the rat and
3. inhibiting effect on salivation in the rat.
   1. Heart rate-increasing effect in the conscious dog
   The substances were either injected intravenously or administered orally and the heart rate was measured with a tachygraph. After a control period increasing doses of the compound were administered in order to increase the heart rate. The next dose was administered as soon as the effect of the preceding dose was no longer apparent. The dosage of a substance which brought about an increase of 50 beats per minutes ($ED_{50}$) was determined graphically. Each substance was tested on 3 to 5 dogs. The results can be seen in Table II.

2. $M_1/M_2$ selectivity in the rat

The method used was described by Hammer and Giachetti (Life Sciences 31, 2991–2998 (1982)). 5 minutes after intravenous injection of increasing doses of the substance, either the right vagus was electrically stimulated (frequency: 25 Hz; pulse width: 2 ms; duration of stimulus: 30 s; number of volts: supramaximal) or 0.3 mg/kg of McN-A-343 was injected intravenously into male THOM rats. The bradycardia produced by vagus stimulation and the increase in blood pressure produced by McN-A-343 were measured. The dosage of the substances which resulted in a 50% reduction either in vagal bradycardia ($M_2$) or in the rise in blood pressure ($M_1$) was determined graphically. For the results see Table III.

3. Salivation-inhibiting effect on the rat

Using the method of Lavy and Mulder (Arch. Int. Pharmacodyn. 178, 437–445, (1969)), male THOM rats anaesthetised with 1.2 g/kg of urethane were given increasing doses of the substance by intravenous route. The secretion of saliva was triggered by subcutaneous administration of 2 mg/kg of pilocarpine. The saliva was soaked up with blotting paper and the area occupied by the saliva was determined by planimetry every 5 minutes. The dosage of substance which reduced the volume of saliva by 50% was determined graphically. For the results see Table III.

B

Studies of bonding to muscarinic receptors:

(1) In vitro: Determination of $IC_{50}$ values

The organ donors were male Sprague-Dawley rats with a body weight of 180–220 g. After removal of the heart and submandibular gland, all further steps were carried out in ice-cold Hepes HCl buffer (pH 7.4; 100 mmolar NaCl, 10 mmolar $MgCl_2$). The whole heart was cut with scissors. All the organs were then homogenised in a Potter apparatus.

For the bonding test the homogenised organ preparations were diluted as follows:

whole heart: 1:400
submandibular gland: 1:400

Incubation of the homogenised organ preparations was carried out at a specific concentration of the radioligand and a series of concentrations of the non-radioactive test substances in an Eppendorf centrifugal test tube at 30° C. Incubation lasted for 45 minutes. The radioligand used was 0.3 nmolar $^3$H-N-methylscopolamine ($^3$H-NMS). Incubation was ended by the addition of ice-cold buffer with subsequent vacuum filtration. The filters were rinsed with cold buffer and their radioactivity was determined. It represents the sum of specific and non-specific bonding of $^3$H-NMS. The amount of non-specific bonding is defined as the radioactivity which was bound in the presence of 1 micromolar quinuclidinyl benzylate. Each test was repeated four times. The $IC_{50}$ values of the non-labelled test substances were determined graphically. They represent the concentration of test substance at which the specific bonding of $^3$H-NMS to the muscarinic receptors in the various organs was inhibited by 50%. The results are shown in Table 1.

(2) In vivo: Determination of the $ID_{50}$ values

For these experiments, female rats with a body weight of about 200 g were used. Before the start of the test the animals were anaesthetised with a dosage of 1.25 g/kg of urethane. The animals were each given the prescribed dosage of test substance by intravenous injection. After 15 minutes, 113 ng/kg of $^3$H-N-methylscopolamine ($^3$H-NMS) were administered by the same route. After another 15 minutes the animals were killed and the heart, bronchi and lachrymal glands were removed. These organs were dissolved in Soluene R and the radioactivity was determined. The measurements were assumed to be total bonding. The amount of non-specific bonding was defined as the radioactivity which could not be displaced by the administration of 2 mg/kg of atropine. $ID_{50}$ values were determined for the individual organs using these tests. The $ID_{50}$ values are the dosages of the test substances which inhibited 50% of the specific bonding of $^3$H-NMS to the muscarinic receptors of the organs in question. The results are shown in Table V.

The following compounds, for example, were investigated as described above:

A=5,11-dihydro-11-[[[2-[2-[(dipropylamino)methyl]-piperidin-1-yl]ethyl]amino]carbonyl]-6H-pyrido[2,3-b][1,4]benzodiazepin-6-one B=4-[[[2-[2-[(diethylamino)methyl]-piperidin-1-yl]ethyl]amino]carbonyl]-4,9-dihydro-3-methyl-10H-thieno[3,4-b][1,5]benzodiazepin-10-one C-9-chloro-11-[[[2-[2-[(diethylamino)methyl]-piperidin-1-yl]ethyl]amino]carbonyl]-5,11-dihydro-6H-pyrido[2,3-b][1,4]benzodiazepin-6-one and as comparison substances X=11-[[2-[(diethylamino)methyl]-piperidin-1-yl]acetyl]-5,11-dihydro-6H-pyrido[2,3-b][1,4]benzodiazepin-6-one (see U.S. Pat. No. 4550107)

Y=5,11-dihydro-11-[(4-methyl-piperazin-1-yl)acetyl]-6H-pyrido[2,3-b][1,4]benzodiazepin-6-one (pirenzepine, see U.S. Pat. No. 3660380)

and

Z=atropine

The following Tables show the results found:

TABLE I

| | Receptor bonding test, in vitro: | | |
|---|---|---|---|
| | Receptor bonding tests $IC_{50}$ [nMl$^{-1}$] | | Selectivity factor Ratio $IC_{50}$ submandibular gland to $IC_{50}$ heart |
| Substance | Heart | Submandibular gland | |
| A | 20 | 200 | 10 |
| B | 3 | 15 | 5 |
| C | 30 | 150 | 5 |
| X | 150 | 5000 | 33 |
| Y | 1500 | 200 | 0.13 |
| Z | 4 | 4 | 1 |

TABLE II

| Heart rate increasing activity on the conscious dog | | |
|---|---|---|
| Tachycardia (dog) $ED_{50}$ [microg/kg] | | Ratio |
| intravenous | oral | $ED_{50}$ p.o./$ED_{50}$ i.v. |
| A  42 | 300 | 7 |
| X  120 | 1750 | 15 |

TABLE III

M₁/M₂ selectivity and salivation-inhibiting effect in the rat

| Substance | activity (rat) $ED_{50}$[microg/kg] i.v. | $M_1$ activity (rat) $ED_{50}$[microg/kg] i.v. | Salivation inhibition (rat) $ED_{50}$ [microg/kg] i.v. | Ratio of salivation inhibition to $M_2$ activity |
|---|---|---|---|---|
| A | 19  | 562 | 458  | 24.05 |
| B | 8   | 33  | 78   | 9.75  |
| C | 58  | 360 | 1399 | 24.12 |
| X | 160 | 988 | 4215 | 26.34 |
| Y | 883 | 40  | 84   | 0.1   |
| Z | 4   | 16  | 9    | 2.25  |

TABLE IV

Dissociation constants ($K_B$ values) on the ileum and spontaneously beating atrium of the guinea pig:

| Substance | $K_B$ [mol/l] Heart | $K_B$ [mol/l] Ileum |
|---|---|---|
| A | $2.45 \times 10^{-9}$  | $2.57 \times 10^{-8}$  |
| B | $2.40 \times 10^{-10}$ | $3.63 \times 10^{-9}$  |
| C | $4.90 \times 10^{-9}$  | $8.32 \times 10^{-8}$  |
| X | $1.05 \times 10^{-7}$  | $6.17 \times 10^{-7}$  |
| Y | $2.4 \times 10^{-7}$   | $1.55 \times 10^{-7}$  |
| Z | $1.41 \times 10^{-9}$  | $8.13 \times 10^{-10}$ |

TABLE V

Receptor bonding test in vivo

| Substance | Heart Atrium | Heart Ventricle | $ID_{50}$ [mg/kg] Bronchi | Lachrymal glands | Ratio of $ID_{50}$ lachrymal gland to $ID_{50}$ atrium |
|---|---|---|---|---|---|
| A | 0.2   | 0.15  | 0.7  | >10.0 | >50 |
| B | 0.025 | 0.006 | 0.15 | >1.0  | >40 |
| C | 0.20  | 0.09  | 3.0  | 10.0  | 50  |
| X | 1.0   | 0.6   | 15.0 | >30.0 | >30 |
| Y | 5.0   | 1.0   | 10.0 | 10.0  | 2   |
| Z | 0.08  | 0.03  | 0.1  | 0.2   | 1.5 |

The data in Table I hereinbefore show that the new compounds of general formula I distinguish between muscarinic receptors in different types of tissue. This is clear from the considerably lower $IC_{50}$ values in tests on heart preparations compared with those from the submandibular gland.

The pharmacological data of Table III hereinbefore show (in total agreement with the receptor bonding studies) that the heart rate is increased by the above-mentioned compounds even at dosages at which no restriction of salivation is observed. The ratio of the $ED_{50}$ of salivation inhibition to the $ED_{50}$ of the $M_2$ activity shows a sufficient safety interval from the said effect of dryness of the mouth for compounds A to X. This demonstrates that substances A to C have adequate therapeutically useful selectivity comparable with that of substance X, whilst showing an increased activity (see Table V).

Moreover, the pharmacological data of Table IV indicate a surprisingly great power of distinction between the heart and smooth muscle. A, B and C are significantly more effective than X and Y, showing a clear selectivity in favour of the heart, and compounds A, B and C show significant advantages of efficacy compared with X and Y. Atropine (compound Z) is an antimuscarinic which is known to be nonselective and shows an inverse selectivity ratio under these model conditions. The compounds mentioned are resorbed extremely well since they have a low dosage ratio p.o. to i.v. The smaller the ratio of $ED_{50}$ p.o. to $ED_{50}$ i.v., the better the resorption of the active substance.

Table V shows the preferential bonding to receptors of the heart (atrium/ventricle). Substances A, B and C show a decisive improvement in potency compared with substances Y and Y in the heart. This is an important therapeutic advantage in the provision of a vagal pacemaker. This increased effectiveness is obtained whilst at the same time the useful selectivity interval from the effects on the exocrine glands is maintained, as is clear from the ratio of the $ID_{50}$ values of the lachrymal glands to the $ID_{50}$ values of the atrium. Atropine (compound Z) on the other hand is not selective.

Moreover, the compounds prepared according to the invention are well tolerated and no toxic side effects have been observed even at the highest doses administered in the pharmacological trials. All the substances of general formula I are characterised by marked stability to hydrolysis. Consequently it is possible to prepare solutions for parenteral administration which can be stored for long periods.

The examples which follow are intended to illustrate the invention:

"M.p." indicates "melting point", "D." indicates "decomposition". Satisfactory elemental analyses, IR, UV, ¹H-NMR and frequently also mass spectra are available for all the compounds.

PREPARATION OF THE STARTING MATERIALS

EXAMPLE A 5,11-Dihydro-8-ethyl-6H-pyrido[2,3-b][1,4]benzodiazepin-6-one 150.0 g (1.34 mol) of potassium tert.butoxide was added to a solution of 155.7 g (1.21 mol) of 2-chloro-3-amino-pyridine in 417 ml of dry dimethylsulphoxide and the mixture was stirred for 15 minutes at a reaction temperature of 40° C. Within 10 minutes, a solution of 218.0 g (1.22 mol) of methyl 2-amino-5-ethyl-benzoate in 50 ml of dimethylsulphoxide was added dropwise to the resultant dark solution and the mixture was then heated to 50° C. for a further 40 minutes. It was left to cool, stirred into 1 liter of ice water and adjusted to pH 6 by the addition of 20% aqueous hydrochloric acid. The crystal slurry obtained was suction filtered, then suspended in 1 liter of 1% aqueous ammonia and suction filtered again. After drying in a circulating air dryer: colourless crystals, m.p. 145°–147° C., which were reacted further directly without any further purification, $R_F$ 0.9 (Macherey-Nagel, Polygram$^R$ SIL G/UV$_{254}$, pre-coated plastic sheets for TLC, eluant: dichloromethane/ethyl acetate/methanol/cyclohexane/aqueous ammonia 59/25/7.5/7.5/1 v/v).

Yield: 270.5 g (81% of theory).

160.0 g (0.58 mol) of the 2-amino-5-ethyl-N-(2-chloropyridin-3-yl)benzamide obtained were dissolved in 256 ml of sulpholane and heated to 170° C. with stirring for 20 minutes. The mixture was left to cool, stirred with 1 liter of acetonitrile, the resulting crystal slurry was suction filtered and washed successively with 50 ml acetonitrile and 100 ml conc. ammonia. It was recrystallised from hot 70% acetic acid and after drying in a circulating air dryer 114.0 g (48% of theory) of pale yellow crystals were obtained, m.p. 232°-234° C., $R_F$ 0.78 (Macherey-Nagel, Polygram$^R$ SIL G/UV$_{254}$, pre-coated plastic sheets for TLC, eluant: dichloromethane/ethyl acetate 1/1 v/v).

EXAMPLE B

8-Bromo-5,11-dihydro-6H-pyrido[2,3-b][1,4]benzodiazepin-6-one

A mixture of 8.2 g (0.0251 mol) of 2-amino-5-bromo-2-(2-chloro-pyridin-3-yl) benzamide (m.p. 187°-188° C. after recrystallisation from acetonitrile; prepared analogously to Example A from 2-chloro-3-aminopyridine and methyl 2-amino-5-bromo-benzoate in a yield of 83% of theory), 16 ml of sulpholane and 0.3 g conc. sulphuric acid was heated to a reaction temperature of 140° C. for 3 hours, whilst nitrogen was bubbled through and the mixture was stirred. After cooling the mixture was added to 150 ml of ice water, the reaction product precipitated was then filtered off and freed from any subsidiary products by chromatography on silica gel (35-70 mesh) using dichloromethane/cyclohexane/ethyl acetate 17/66/17 (v/v) as eluant. After recrystallisation from dimethylacetamide and acetonitrile, 4.4 g (60% of theory) of pale yellow crystals were obtained, m.p. 338°-340° C.

EXAMPLE C 5,11-Dihydro-9-methyl-6H-pyrido[2,3-b][1,4]benzodiazepin-6-one 127.0 g (0.485 mol) of 2-amino-N-(2-chloro-pyridin-3-yl)-4-methyl-benzamide (m.p. 150°-152° C.) prepared analogously to Example A from 2-chloro-3-amino-pyridine and methyl 2-amino-4-methyl-benzoate (see F. Mayer and R. Schulze, Ber. Dtsch. Chem. Ges. 58, 1465 [1925]) were suspended in 500 ml of sulpholane and after the addition of 1.4 ml of conc. sulphuric acid the suspension was heated for 3 hours to 130° C. with stirring. It was then left to cool to 80° C., 500 ml of toluene were added and the mixture was left to stand overnight at ambient temperature. The crystals formed were suction filtered, suspended in 0.75 liters of dichloromethane, suction filtered once more and thoroughly washed with dichloromethane. After drying in a circulating air dryer, 70.2 g (64% of theory) of very slightly yellow crystals were obtained, m.p. 286°-288° C., which were further reacted without any further purification.

EXAMPLE D 4-(Chlorocarbonyl)-4,9-dihydro-3-methyl-10H-thieno[3,4-b][1,5]benzodiazepin-10-one 8.2 g (0.036 mol) of 4,9-dihydro-3-methyl-10H-thieno[3,4-b][1,5]benzodiazepin-10-one were suspended in 365 ml of dichloromethane and after the addition of 40 ml (0.08 mol) of a 20% phosgene solution in toluene the mixture was stirred for 7 days at ambient temperature. The solution formed was washed three times, each time with 80 ml of water, dried over sodium sulphate and the solvent was eliminated in vacuo. The desired compound was freed from contaminants by column chromatography on MN silica gel 60 (70-230 mesh ASTM) using dichloromethane/ethyl acetate/petroleum ether 5/5/4 (v/v) as eluant. 6.1 g (58% of theory) of colourless crystals were obtained, m.p. 238°-239° C., $R_F$ 0.77 (Macherey-Nagel, Polygram$^R$ SIL G/UV$_{254}$, pre-coated plastic sheets for TLC, eluant: dichloromethane/ethyl acetate/petroleum ether 5/5/4 v/v).

The following were obtained accordingly:
4-(chlorocarbonyl)-4,9-dihydro-10H-thieno[3,4-b][1,5]benzodiazepin-10H-one, m.p. 244°-245° C. (D.) (acetonitrile);
4-(chlorocarbonyl)-4,9-dihydro-1-methyl-10H-thieno[3,4-b][1,5]benzodiazepin-10H-one, m.p. 235°-236° C. (from chloroform);
4-(chlorocarbonyl)-4,9-dihydro-1,3-dimethyl-10H-thieno[3,4-b][1,5]benzodiazepin-10-one as an amorphous foamy product which was reacted further without any purification;
3-chloro-4-(chlorocarbonyl)-4,9-dihydro-10H-thieno[3,4-b][1,5]benzodiazepin-10-one, m.p. 238°-240° C. (ethanol);
from 4,9-dihydro-3-methyl-10H-thieno[3,4-b][1,5]benzodiazepin-10-one and methyl chlorocarbonate, 4,9-dihydro-4-(methoxycarbonyl)-3-methyl-10H-thieno[3,4-b][1,5]benzodiazepin-10-one was obtained;
from 4,9-dihydro-3-methyl-10H-thieno[3,4-b][1,5]benzodiazepin-10-one and benzyl chlorocarbonate, 4-(benzyloxycarbonyl)-4,9-dihydro-3-methyl-10H-thieno[3,4-b][1,5]benzodiazepin-10-one was obtained.

EXAMPLE E 11-(Chlorocarbonyl)-5,11-dihydro-6H-pyrido[2,3-b][1,4]benzodiazepin-6-one To a suspension of 158.3 g (0.75 mol) of 5,11-dihydro-6H-pyrido[2,3-b][1,4]benzodiazepin-6-one in 3 liters of dioxane, 730 ml (1.46 mol) of a 20% solution of phosgene in toluene was added dropwise within 45 minutes and the resulting mixture was then stirred for 2 hours at ambient temperature. 1.5 l of water were added, the mixture was stirred for a further 2 hours at ambient temperature and the precipitate formed was suction filtered. The product was washed thoroughly with water and dried in a circulating air dryer. Colourless crystals, m.p. 239°-240° C.

Yield: 178.8 g (87% of theory).

EXAMPLE F

9-Chloro-11-(chlorocarbonyl)-5,11-dihydro-6H-pyrido[2,3-b][1,4]benzodiazepin-6-one 11.6 g (0.0472 mol) of 9-chloro-5,11-dihydro-6H-pyrido[2,3-b][1,4]benzodiazepin-6-one, suspended in a mixture of 450 ml of anhydrous dioxane and 6.4 ml (0.08 mol) of pyridine, were combined at 45° C., within 20 minutes, with 47.1 ml (0.094 mol) of a 20% solution of phosgene in toluene. The reaction mixture was stirred for 2 hours at 45° C. and then for 4 hours at 60° C. The mixture was filtered while hot, the filtrate was evaporated down in vacuo, the crystallising residue remaining was resuspended in 100 ml of dioxane, refluxed for 2 hours, evaporated down once more, mixed with copious amounts of water and suction filtered. After drying in a circulating air dryer the product had an m.p. of 265°-267° C., $R_F$ 0.70 (Macherey-Nagel, Polygram$^R$ SIL G/UV$_{254}$, pre-coated plastic sheets for TLC, eluant: dichloromethane/ethyl acetate 1/1 v/v).

Yield: 12.0 g (83% of theory).

The following were prepared analogously:

11-(chlorocarbonyl)-7-fluoro-5,11-dihydro-6H-pyrido[2,3-b][1,4]benzodiazepin-6-one;

11-(chlorocarbonyl)-8-fluoro-5,11-dihydro-6H-pyrido[2,3-b][1,4]benzodiazepin-6-one;

11-(chlorocarbonyl)-9-fluoro-5,11-dihydro-6H-pyrido[2,3-b][1,4]benzodiazepin-6-one;

11-(chlorocarbonyl)-8-methyl-5,11-dihydro-6H-pyrido[2,3-b][1,4]benzodiazepin-6-one in a yield of 92% of theory; m.p. 209°–210° C. (D); R$_F$ 0.70 (Macherey-Nagel, Polygram$^R$ SIL G/UV$_{254}$, pre-coated plastic sheets for TLC, eluant: dichloromethane/ethyl acetate 1/1 v/v);

8-chloro-11-(chlorocarbonyl)-5,11-dihydro-6H-pyrido[2,3-b][1,4]benzodiazepin-6-one in a yield of 72% of theory, m.p. 216°–220° C.; R$_F$ 0.78 (Macherey-Nagel, Polygram$^R$ SIL G/UV$_{254}$, pre-coated plastic sheets for TLC, eluant: dichloromethane/ethyl acetate 1/1 v/v)

11-(chlorocarbonyl)-8-ethyl-5,11-dihydro-6H-pyrido[2,3-b][1,4]benzodiazepin-6-one in a yield of 80% of theory; m.p. 206°–208° C.; R$_F$ 0.69 (Macherey-Nagel, Polygram$^R$ SIL/UV$_{254}$, pre-coated plastic sheets for TLC, eluant: dichloromethane/ethyl acetate/methanol/cyclohexane/conc. ammonia 54.5/37/4/4/0.5 v/v);

11-(chlorocarbonyl)-9-methyl-5,11-dihydro-6H-pyrido[2,3-b][1,4]benzodiazepin-6-one with R$_F$ 0.70 (Macherey-Nagel, Polygram$^R$ SIL G/UV$_{254}$, pre-coated plastic sheets for TLC, eluant: dichloromethane/ethyl acetate 1/1 v/v);

8-bromo-9-(chlorocarbonyl)-5,11-dihydro-6H-pyrido[2,3-b][1,4]benzodiazepin-6-one, with R$_F$ 0.75 (Macherey-Nagel, Polygram$^R$ SIL G/UV$_{254}$, pre-coated plastic sheets for TLC, eluant: dichloromethane/ethyl acetate 1/1 v/v) or 0.80 (eluant: dichloromethane/ethyl acetate/methanol/cyclohexane/conc. ammonia 59/25/7.5/7.5/1 v/v);

4-(chlorocarbonyl)-1,3-dimethyl-1,4,9,10-tetrahydropyrazolo[4,3-e]pyrido[3,2-b][1,4]diazepin-10-one, m.p. 208°–212° C. (acetonitrile) in a yield of 70% of theory;

11-(chlorocarbonyl)-6,11-dihydro-5H-pyrido[2,3-b][1,5]benzodiazepin-5-one, m.p. 246°–247° C. in a yield of 85% of theory;

5-(chlorocarbonyl)-5,11-dihydro-10H-pyrido[3,2-b][1,4]benzodiazepin-10-one, 4-(chlorocarbonyl)-1,3-dimethyl-1,4,9,10-tetrahydropyrrolo[3,2-b][1,5]benzodiazepin-10-one;

3-chloro-4-(chlorocarbonyl)-1-methyl-1,4,9,10-tetrahydropyrrolo[3,2-b][1,5]benzodiazepin-10-one;

4-(chlorocarbonyl)-1-methyl-1,4,9,10-tetrahydropyrazolo[4,3-e]pyrido[3,2-b][1,4]diazepin-10-one;

4-(chlorocarbonyl)-1,3-dimethyl-1,4,9,10-tetrahydropyrazolo[4,3-b][1,5]benzodiazepin-10-one;

6-chloro-5-(chlorocarbonyl)-5,10-dihydro-11H-dibenzo[b,e][1,4]diazepin-11-one.

EXAMPLE G

2-[2-[(Diethylamino)methyl]-piperidin-1-yl]acetonitrile

A mixture of 236.5 ml (about 1.1 mol) of a 37% aqueous sodium hydrogen sulphite solution and 110 ml (about 1.1 mol) of a 40% formalin solution was heated to 60° C. for 30 minutes. It was allowed to cool to 30° C., a solution of 170.3 g (1.0 mol) of 2-[(diethylamino)methyl]piperidine in 70 ml of water was added dropwise thereto, whereupon the mixture spontaneously heated up to 40° C., and was then stirred for a further 2 hours without any external heating. The solution of 53.9 g (1.1 mol) of sodium cyanide in 172 ml of water was then added and the resulting mixture was stirred for 2 hours at ambient temperature. The upper organic layer was taken up in 500 ml of cyclohexane and the aqueous phase was extracted four times, each time with 125 ml of cyclohexane. The combined extracts were dried over sodium sulphate, concentrated by evaporation and distilled in vacuo. The desired 2-[2-[(diethylamino)methyl]-piperidin-1-yl]acetonitrile was obtained as a colourless oil, B.p.$_{19\ mm\ Hg}$ 155°–156° C. in a yield of 172.0 g (82% of theory).

The following were obtained analogously:

2-[2-[3-(dimethylamino)-prop-1-yl]-piperidin-1-yl]acetonitrile, R$_F$ 0.75 (Macherey-Nagel, Polygram$^R$ SIL G/UV$_{254}$, pre-coated plastic sheets for TLC, eluant: dichloromethane/methanol/cyclohexane/conc. ammonia 68/15/15/2 v/v) in a yield of 99% of theory;

2-[2-[2-(dimethylamino)ethyl]-piperidin-1-yl]acetonitrile, B.p.$_{15\ mm\ Hg}$ 140°–142° C. in a yield of 61% of theory;

2-[3-[(diethylamino)methyl]-morpholin-4-yl]acetonitrile, R$_F$ 0.80 (Macherey-Nagel, Polygram$^R$ SIL G/UV$_{254}$, pre-coated plastic sheets for TLC, eluant: dichloromethane/ethyl acetate/cyclohexane/methanol/conc. ammonia 58/25/8/8/1 v/v) in a yield of 88% of theory;

2-[2-[(dipropylamino)methyl]-piperidin-1-yl]acetonitrile, B.p.$_{18\ mm\ Hg}$ 162°–170° C., R$_f$ 0.95 (Macherey-Nagel, Polygram SIL G/UV$_{254}$, pre-coated plastic sheets for TLC, eluant: dichloromethane/methanol/cyclohexane/conc. ammonia 68/15/15/2 v/v) in a yield of 55% of theory;

2-[2-[4-(diethylamino)butyl]-piperidin-1-yl]acetonitrile, B.p.$_{0.1\ mm\ Hg}$ 103°–113° C. in a yield of 71% of theory;

2-[2-[(piperidin-1-yl)methyl]-piperidin-1-yl]acetonitrile, B.p.$_{0.2\ mm\ Hg}$ 110°–113° C. in a yield of 66% of theory;

2-[3-(diethylamino)-hexahydro-1H-azepin-1-yl]acetonitrile, B.p.$_{20\ mm\ Hg}$ 164°–170° C. in a yield of 83% of theory;

2-[2-[(morpholin-4-yl)methyl]-piperidin-1-yl]acetonitrile, B.p.$_{0.4\ mm\ Hg}$ 134°–139° C. in a yield of 84% of theory;

2-[2-[(pyrrolidin-1-yl)methyl]-piperidin-1-yl]acetonitrile, B.p.$_{20\ mm\ Hg}$ 168°–170° C. in a yield of 67% of theory;

2-[2-[[bis-(methylethyl)amino]methyl]-piperidin-1-yl]-acetonitrile;

2-[2-[(butylethylamino)methyl]-piperidin-1-yl]acetonitrile in a yield of 83% of theory, colourless oil, B.p.$_{15\ mm\ Hg}$ 168°–171° C.;

2-[2-[(hexahydro-1H-azepin-1-yl)methyl]-piperidin-1-yl]acetonitrile in a yield of 74% of theory, colourless oil, B.p.$_{0.3\ mm\ Hg}$ 120°–124° C.;

(+) -2-[2-[(diethylamino)methyl]-piperidin-1-yl]acetonitrile, B.p.$_{19\ mm\ Hg}$ 155°–157° C. in a yield of 79% of theory;

(−) -2-[2-[(diethylamino)methyl]-piperidin-1-yl]acetonitrile, B.p.$_{19\ mm\ Hg}$ 154°–156° C. in a yield of 84% of theory;

(+) -2-[2-[(dipropylamino)methyl]-piperidin-1-yl]acetonitrile, B.p.$_{18\ mm\ Hg}$ 163°–168° C. in a yield of 58% of theory;

(−) -2-[2-[(dipropylamino)methyl]-piperidin-1-yl]acetonitrile, B.p.$_{18\ mm\ Hg}$ 161°–169° C. in a yield of 53% of theory;

2-[3-[(diethylamino)methyl]-pyrrolidin-1-yl]acetonitrile;

2-[3-[(dipropylamino)methyl]-pyrrolidin-1-yl]acetonitrile;

2-[3-[(piperidin-1-yl)methyl]-pyrrolidin-1-yl]acetonitrile;

2-[3-[[(cyclohexyl)methylamino]methyl]-pyrrolidin-1-yl]acetonitrile, which was further processed in its crude state, in a yield of 91% of theory;

2-[2-[[(cyclopentyl)methylamino]methyl]-piperidin-1-yl]acetonitrile in a yield of 95% of theory, colourless, freely moving oil, R$_F$ 0.95 (Macherey-Nagel, Polygram$^R$ SIL G/UV$_{254}$, pre-coated plastic sheets for TLC; eluant: dichloromethane/ethyl acetate/methanol/cyclohexane/conc. ammonia 59/25/7.5/7.5/1 v/v);

2-[3-[(diethylamino)methyl]-piperidin-1-yl]acetonitrile in a yield of 90% of theory, R$_F$ 0.51 (Macherey-Nagel, Polygram$^R$ SIL G/UV$_{254}$, pre-coated plastic sheets for TLC, eluant: dichloromethane/ethyl acetate/cyclohexane/methanol/conc. ammonia 58/25/8/8/1 v/v);

2-[3-[(dipropylamino)methyl]-piperidin-1-yl]acetonitrile in a yield of 76% of theory, R$_F$0.545 (Macherey-Nagel, Polygram$^R$ SIL G/UV$_{254}$, pre-coated plastic sheets for TLC, eluant: dichloromethane/methanol/conc. ammonia 89/10/1 v/v);

2-[3-[(piperidin-1-yl)methyl]-piperidin-1-yl]acetonitrile;

2-[3-[(hexahydro-1H-azepin-1-yl)methyl]-piperidin-1-yl]acetonitrile in a yield of 34% of theory, R$_F$ 0.515 (Macherey-Nagel, Polygram$^R$ SIL G/UV$_{254}$, pre-coated plastic sheets for TLC, eluant: dichloromethane/ethyl acetate/cyclohexane/methanol/conc. ammonia 58/15/8/8/1 v/v);

2-[3-[3-(piperidin-1-yl)propyl]-piperidin-1-yl]acetonitrile in a yield of 62% of theory;

2-[3-[(piperidin-1-yl)methyl]-piperidin-1-yl]acetonitrile in a yield of 94% of theory;

2-[3-[2-(piperidin-1-yl)ethyl]-piperidin-1-yl]acetonitrile in a yield of 72% of theory, R$_F$ 0.49 (Merck ready-made TLC plates, silica gel 60 F$_{254}$; eluant: dichloromethane/methanol/conc. ammonia 90/10/1 v/v);

2-[3-[4-(dimethylamino)butyl]-piperidin-1-yl]acetonitrile in a yield of 93% of theory, R$_F$0.39 (TLC investigation as above);

2-[3-[4-(pyrrolidin-1-yl)butyl]-piperidin-1-yl]acetonitrile in a yield of 90% of theory, colourless oil, R$_F$ 0.29 (TLC investigation as above);

2-[3-[4-(diethylamino)butyl]-piperidin-1-yl]acetonitrile in a yield of 94% of theory, colourless, thinly fluid oil, R$_F$ 0.60 (TLC investigation as above);

2-[2-[4-(piperidin-1-yl)butyl]-piperidin-1-yl]acetonitrile in a yield of 83% of theory, colourless oil, B.p.$_{0.1\ mm\ Hg}$ 149°–150° C;

2-[2-[[bis-(methylethyl)amino]methyl]-piperidin-1-yl]acetonitrile in a yield of 67% of theory, colourless oil, B.p.$_{15\ mm\ Hg}$ 163°–165° C.;

2-[2-[(ethylpropylamino)methyl]-piperidin-1-yl]acetonitrile in a yield of 71% of theory, colourless oil, B.p.$_{10\ mm\ Hg}$ 150°–152° C.

EXAMPLE H

3-[2-[(Diethylamino)methyl]-piperidin-1-yl]propane nitrile

In a 500 ml three-necked flask with stirrer, dropper funnel, reflux condenser and internal thermometer, 42.5 g (0.25 mol) of 2-[(diethylamino)methyl]piperidine are dissolved in 250 ml of ethanol. 17.8 ml (0.267 mol) of acrylonitrile are added dropwise to this solution with stirring while the internal temperature is kept below 30° C. After the addition of 6 drops of a methanolic Triton-B solution, the mixture is stirred for a further 24 hours at ambient temperature. The solvent is removed under reduced pressure and the residue is distilled in vacuo. Colourless oil, B.p.$_{0.3\ mm\ Hg}$ 110°–113° C.

Yield: 40.3 g (72% of theory).

The following was obtained analogously:

3-[2-[(dimethylamino)methyl]-piperidin-1-yl]propane nitrile, B.p.$_{0.3\ mm\ Hg}$ 90°–92° C., in a yield of 78% of theory.

EXAMPLE I

2-[2-[3-(Dimethylamino)propyl]-piperidin-1-yl]acetonitrile

A mixture of 17.0 g (0.1 mol) of 2-[3-(dimethylamino)propyl]piperidine, 15.2 ml (0.11 mol) of triethylamine, 100 ml of anhydrous tetrahydrofuran and 6.9 ml (0.11 mol) of chloroacetonitrile was refluxed for 8 hours. After cooling, the mixture was filtered and the filtrate was evaporated down in vacuo. 3.2 g (15% of theory) of the above compound were obtained, R$_F$0.75 (Macherey-Nagel, Polygram$^R$ SIL G/UV$_{254}$, pre-coated plastic sheets for TLC, eluant: dichloromethane/methanol/cyclohexane/conc. ammonia 68/15/15/2).

The following were obtained analogously:

(±)-2-[2-[2-(diethylamino)ethyl]-pyrrolidin-1-yl]acetonitrile in a yield of 98% of theory;

(±)-2-[2-[(diethylamino)methyl]-pyrrolidin-1-yl]acetonitrile, B.p.$_{12\ mm\ Hg}$ 122°–125° C. in a yield of 73% of theory.

EXAMPLE K

4-[2-[(Diethylamino)methyl]-piperidin-1-yl]butane nitrile

A mixture of 17.0 g (0.1 mol) of 2-[(diethylamino)methyl]piperidine, 16.3 g (0.11 mol) of 4-bromo-butane nitrile, 12.7 g (0.12 mol) of sodium carbonate and 100 ml of tetrahydrofuran was refluxed for 6 hours with stirring. After cooling the insoluble matter was filtered off, the solvent was removed and the residue was purified by chromatography on silica gel (35–70 mesh ASTM) using dichloromethane/ethyl acetate/cyclohexane/methanol/conc. ammonia 3.5/1.5/0.46/0.46/0.06 as eluant. 20.9 g (88% of theory) of a colourless oil were obtained, R$_F$ 0.5 (Macherey-Nagel, Polygram$^R$ SIL G/UV$_{254}$, pre-coated plastic sheets for TLC, eluant: as above).

The following were obtained analogously:

from 2-[(diethylamino)methyl]piperidine and 6-bromohexane nitrile in a yield of 84% of theory, 6-[2-[(diethylamino)methyl]-piperidin-1-yl]hexane nitrile, B.p.$_{0.2\ mm\ Hg}$ 135°–136° C.;

from 2-[(dimethylamino)methyl]piperidine and 4-bromobutane nitrile in a yield of 47% of theory, 4-[2-[(dimethylamino)methyl]-piperidin-1-yl]butane nitrile, R$_F$ 0.45 (TLC investigation as above), which crystallised after standing for some time. M.p. 137°–139° C.;

from ·2-[(dipropylamino)methyl]piperidine and 2-bromoacetonitrile, (±)-2-[2-[(dipropylamino)methyl]piperidin-1-yl]acetonitrile, $R_F$ 0.9 (Macherey-Nagel, Polygram$^R$ SIL G/UV$_{254}$, pre-coated plastic sheets for TLC, eluant: dichloromethane/ethyl acetate 50:50 v/v).

EXAMPLE L

2-[2-[(Dimethylamino)methyl]-piperidin-1-yl]acetamide 28.0 g (0.197 mol) of 2-[(dimethylamino)methyl]piperidine were dissolved in 200 ml of ethanol and after the addition of 22.4 g (0.24 mol) of chloroacetamide and 20.1 g (0.24 mol) of sodium hydrogen carbonate the mixture was refluxed for 48 hours. After cooling, it was filtered, the filtrate was evaporated down in vacuo. 22.0 g (56% of theory) of a light yellow oil were obtained, $R_F$ 0.50 (Macherey-Nagel, Polygram$^R$ SIL G/UV$_{254}$, pre-coated plastic sheets for TLC, eluant: dichloromethane/methanol/cyclohexane/conc. ammonia 68/15/15/2 v/v), which was further processed without any further purification.

The following were obtained analogously:

from 2-[2-(diethylamino)ethyl]piperidine and chloroacetamide in a yield of 79% of theory, 2-[2-[2-(diethylamino)ethyl]-piperidin-1-yl]acetamide, $R_F$ 0.50 (TLC investigation as above);

from 2-[3-(diethylamino)propyl]piperidine and chloroacetamide in a yield of 65% of theory, 2-[2-[3-(diethylamino)propyl]-piperidin-1-yl]acetamide, $R_F$ 0.50 (TLC investigation as above);

from 2-[(diethylamino)methyl]piperidine and N-methylchloroacetamide in a yield of 81% of theory, 2-[2-[(diethylamino)methyl]-piperidin-1-yl]-N-methylacetamide, $R_F$ 0.85 (TLC investigation as above);

from 2-[(dimethylamino)methyl]piperidine and N-methyl-chloroacetamide in a yield of 70% of theory, 2-[2-[(dimethylamino)methyl]-piperidin-1-yl]-N-methylacetamide, $R_F$ 0.80 (TLC investigation as above);

from trans-2-[[(4-hydroxy-cyclohexyl)methylamino]methyl]piperidine and N-methyl-chloroacetamide in a yield of 48% of theory, trans-2-[2-[[(4-hydroxy-cyclohexyl)methylamino]methyl]-piperidin-1-yl]-N-methyl-acetamide, m.p. 104°–105° C.;

from 2-[2-(diethylamino)ethyl]piperidine and N-methyl-chloroacetamide in a yield of 94% of theory, 2-[2-[2-(diethylamino)ethyl]-piperidin-1-yl]N-methylacetamide, $R_F$ 0.80 (TLC investigation as above);

from 4-[2-(diethylamino)ethyl]piperidine and iodoacetamide in a yield of 95% of theory, 2-[4-[2-(diethylamino)ethyl]-piperidin-1-yl]acetamide;

from 4-[(diethylamino)methyl]piperidine and iodoacetamide in a yield of 92% of theory, 2-[4-[(diethylamino)methyl]-piperidin-1-yl]acetamide;

from 4-[2-(piperidin-1-yl)ethyl]piperidine and iodoacetamide in a yield of 89% of theory, 2-[4-[2-(piperidin-1-yl)ethyl]-piperidin-1-yl]acetamide;

from 4-[4-(piperidin-1-yl)butyl]piperidine and iodoacetamide in a yield of 60% of theory, 2-[4-[4-(piperidin-1-yl)-butyl]-piperidin-1-yl]acetamide, m.p. 112°–116° C.;

from N,N-bis(methylethyl)-hexahydro-4-pyridine propanamide and iodoacetamide, 2-[4-[3-[bis-(methylethyl)amino]-3-oxo-propyl]-piperidin-1-yl]acetamide, which was used in its crude state, in a yield of 30% of theory;

from 4-[3-(dipropylamino)propyl]piperidine and iodoacetamide, 2-[4-[3-(dipropylamino)propyl]piperidin-1-yl]acetamide, which was used without purification, in a yield of 43%, $R_F$ 0.50 (TLC investigation as above);

from N,N-diethyl-hexahydro-4-pyridine propanamide and iodoacetamide, crystalline 2-[4-[3-(diethylamino)-3-oxo-propyl]-piperidin-1-yl]acetamide, which was used in its crude state, in a yield of 81% of theory;

from 4-[3-(piperidin-1-yl)propyl]piperidine and iodoacetamide in a yield of 96% of theory, 2-[4-[3-(piperidin-1-yl)propyl]-piperidin-1-yl]acetamide, m.p. 94°–97° C.

EXAMPLE M

O-Ethyl [2-[2-[2-(dimethylamino)ethyl]-piperidin-1-yl]-ethyl]-carbaminate

To a mixture of 14.9 g (0.075 mol) of 2-[2-[2-(dimethylamino)ethyl]-piperidin-1-yl]ethylamine, 12.7 ml (0.091 mol) of triethylamine and 150 ml of anhydrous ethanol, 8.6 ml (0.09 mol) of ethyl chlorocarbonate were added dropwise and the mixture was then stirred for 2 hours at ambient temperature. The volatile components were distilled off in a water jet vacuum and the residue was taken up in 30 ml of water; the solution obtained was saturated with potassium carbonate and exhaustively extracted with ethyl acetate. The combined extracts were dried over sodium sulphate, filtered and evaporated down once more. After distillation in a fine vacuum (B.p.$_{0.2}$ $mm$ $Hg$ 141–143° C.) the residue remaining yielded a colourless oil in a yield of 14.0 g (69% of theory).

The following were obtained analogously:

O-ethyl [4-[2-[(dimethylamino)methyl]-piperidin-1-yl]butyl]carbaminate, $R_F$0.3 (Macherey-Nagel, Polygram$^R$ SIL G/UV$_{254}$, pre-coated plastic sheets for TLC, eluant: dichloromethane/ethyl acetate/cyclohexane/methanol/conc. ammonia 58/25/8/8/1), in a yield of 83% of theory;

O-methyl [4-[2-[(diethylamino)methyl]-piperidin-1-yl]-butyl]carbaminate, colourless oil, in a yield of 93% of theory.

EXAMPLE N

2-[2-[(Diethylamino)methyl]-piperidin-1-yl]ethanamine 200 ml of anhydrous ether and 10.7 g (0.282 mol) of lithium aluminium hydride were placed in a 500 ml three-necked flask with stirrer, two-neck attachment, dropper funnel and reflux condenser with a calcium chloride tube, and a solution of 43.0 g (0.189 mol) of 2-[2-[(diethylamino)methyl]-piperidin-1-yl]acetamide in 60 ml of absolute ether was added dropwise with constant stirring so that the ether was maintained at a steady boil. After the end of the dropwise addition the mixture was stirred for a further 6 hours whilst simultaneously being refluxed, then the excess lithium aluminium hydride was decomposed by the dropwise addition of 11 ml of water, 11 ml of 15% aqueous sodium hydroxide solution and 33 ml of water, one after the other, and the aluminium oxide hydrate precipitated was filtered off. The filtrate was dried over sodium sulphate, the solvent was removed and the residue was distilled in a fine vacuum. 12.7 g (31% of theory) of a colourless oil were obtained, B.p.$_{0.2\ mm\ Hg}$ 80°–82° C., R$_f$ 0.5 (Macherey-Nagel, Polygram$^R$ SIL G/UV$_{254}$, pre-coated plastic sheets for TLC, eluant: dichloromethane/methanol/cyclohexane/conc. ammonia 68/15/15/2).

The following were obtained analogously:

from 3-[2-[(diethylamino)methyl]-piperidin-1-yl]propane nitrile in a yield of 72% of theory, 3-[2-[(diethylamino)methyl]-piperidin-1-yl]propanamine, B.p.$_{0.2\ mm\ Hg}$ 92°–93° C.;

from 2-[2-[(diethylamino)methyl]-piperidin-1-yl]acetonitrile in a yield of 87% of theory, 2-[2-[(diethylamino)methyl]-piperidin-1-yl]ethanamine, B.p.$_{15\ mm\ Hg}$ 135°–138° C.;

from 2-[2-[(dimethylamino)methyl]-piperidin-1-yl]acetamide in a yield of 42% of theory, 2-[2-[(dimethylamino)methyl]-piperidin-1-yl]ethanamine, B.p.$_{0.15\ mm\ Hg}$ 62°–65° C.;

from 3-[2-[(dimethylamino)methyl]-piperidin-1-yl]propane nitrile in a yield of 53% of theory, 3-[2-[(dimethylamino)methyl]-piperidin-1-yl]propanamine, B.p.$_{0.3\ mm\ Hg}$ 80°–82° C.;

from 2-[2-[2-(diethylamino)ethyl]-piperidin-1-yl]acetamide in a yield of 47% of theory, 2-[2-[2-(diethylamino)ethyl]-piperidin-1-yl]ethanamine, B.p.$_{15\ mm\ Hg}$ 155°–161° C., R$_F$ 0.3 (TLC investigation as above);

from 2-[2-[3-(dimethylamino)propyl]-piperidin-1-yl]acetonitrie in a yield of 75% of theory, 2-[2-[3-(dimethylamino)propyl]-piperidin-1-yl]ethanamine, B.p.$_{26\ mm\ Hg}$ 153°–154° C.;

from 2-[2-[3-(diethylamino)propyl]-piperidin-1-yl]acetamide in a yield of 38% of theory, 2-[2-[3-(diethylamino)propyl]-piperidin-1-yl]ethanamine, B.p.$_{15\ mm\ Hg}$ 169°–173° C.;

from 4-[2-[(diethylamino)methyl]-piperidin-1-yl]butane nitrile in a yield of 36% of theory, 4-[2-[(diethylamino)methyl]-piperidin-1-yl]butanamine, R$_F$ 0.2 (TLC conditions as above but using as eluant: dichloromethane/cyclohexane/methanol/conc. ammonia 4.08/0.92/0.92/0.12);

from 2-[2-[2-(dimethylamino)ethyl]-piperidin-1-yl]acetonitrile in a yield of 67% of theory, 2-[2-[2-(dimethylamino)ethyl]-piperidin-1-yl]ethanamine, B.p.$_{18\ mm\ Hg}$ 131°–134° C.;

from 2-[2-[(diethylamino)methyl]-piperidin-1-yl]-N-methyl-acetamide in a yield of 33% of theory, 2-[2-[(diethylamino)methyl]-piperidin-1-yl]-N-methylethanamine, B.p.$_{15\ mm\ Hg}$ 148°–152° C.;

from 6-[2-[(diethylamino)methyl]-piperidin-1-yl]hexane nitrile in a yield of 44% of theory, 6-[2-[(diethylamino)methyl]-piperidin-1-yl]hexanamine, B.p.$_{0.2\ mm\ Hg}$ 149°–151° C.;

from 2-[2-[(dimethylamino)methyl]-piperidin-1-yl]-N-methyl-acetamide in a yield of 39% of theory, 2-[2-[(dimethylamino)methyl]-piperidin-1-yl]-N-methylethanamine, B.p.$_{18\ mm\ Hg}$ 127°–132° C.;

from trans 2-[2-[[(4-hydroxy-cyclohexyl)methylamino]methyl]-piperidin-1-yl]-N-methyl-acetamide in a yield of 90% of theory, trans-2-[2-[[(4-hydroxy-cyclohexyl)methylamino]methyl]-piperidin-1-yl]-N-methylethanamine, R$_F$ 0.1 (TLC conditions as above), which begins to crystallise when left to stand for some time;

from 2-[2-[2-(diethylamino)ethyl]-piperidin-1-yl]-N-methyl-acetamide in a yield of 31% of theory, 2-[2-[2-(diethylamino)ethyl]-piperidin-1-yl]-N-methylethanamine, B.p.$_{18\ mm\ Hg}$ 155°–159° C.;

from 4-[2-[(dimethylamino)methyl]-piperidin-1-yl]butane nitrile in a yield of 86% of theory, 4-[2-[(dimethylamino)methyl]-piperidin-1-yl]butanamine, R$_F$ 0.15 (TLC investigation as above);

from trans-2-[2-[[(4-hydroxy-cyclohexyl)methylaminol]methyl]-piperidin-1-yl]acetamide in a yield of 57% of theory, trans-2-[2-[[(4-hydroxy-cyclohexyl)methylamino]methyl]-piperidin-1-yl]ethanamine, R$_F$ 0.15 (TLC investigation as above);

from 2-[4-[2-(piperidin-1-yl)-2-oxo-ethyl]-piperidin-1-yl]acetamide in a yield of 83% of theory, 2-[4-[2-(piperidin-1-yl)ethyl]-piperidin-1-yl]ethanamine, which was used without further purification;

from O-ethyl [2-[2-[2-(dimethylamino)ethyl]-piperidin-1-yl]carbaminate in a yield of 67% of theory, 2-[2-[2-(dimethylamino)ethyl]-piperidin-1-yl]ethyl]-N-methylethanamine, B.p.$_{20\ mm\ Hg}$ 148°–151° C.;

from O-ethyl [4-[2-[(dimethylamino)methyl]-piperidin-1-yl]butyl]carbaminate, in a yield of 84% of theory, 4-[2-[(dimethylamino)methyl]-piperidin-1-yl]butyl]-N-methyl-butanamine, R$_F$ 0.1 (TLC investigation as above);

from O-ethyl [4-[2-[(diethylamino)methyl]-piperidin-1-yl]butyl]carbaminate in a yield of 84% of theory, 4-[2-[(diethylamino)methyl]-piperidin-1-yl]-N-methylbutanamine, B.p.$_{0.1\ mm\ Hg}$ 103°–110° C.;

from 2-[2-[2-(diethylamino)ethyl]-pyrrolidin-1-yl]acetonitrile in a yield of 56% of theory, 2-[2-[2-(diethylamino)ethyl]-pyrrolidin-1-yl]ethanamine, B.p.$_{20\ mm\ Hg}$ 125°–130° C.;

from 2-[2-[(diethylamino)methyl]-pyrrolidin-1-yl]acetonitrile in a yield of 58% of theory, 2-[2-[(diethylamino)methyl]-pyrrolidin-1-yl]ethanamine, B.p.$_{12\ mm\ Hg}$ 114°–117° C.;

from 2-[4-[(diethylamino)methyl]-piperidin-1-yl]acetamide in a yield of 32% of theory, 2-[4-[(diethylamino)methyl]-piperidin-1-yl]ethanamine, B.p.$_{12\ mm\ Hg}$ 132°–138° C.;

from 2-[4-[3-(diethylamino)-3-oxo-propyl]-piperidin-1-yl]acetamide in a yield of 74% of theory, 2-[4-[3-(diethylamino)propyl]-piperidin-1-yl]ethanamine, which was used without further purification, R$_F$ 0.2 (Macherey-Nagel, Polygram$^R$ SIL G/UV$_{254}$, pre-coated plastic sheets for TLC, eluant: dichloromethane/cyclohexane/methanol/conc. ammonia 68/15/15/2 v/v);

from 2-[4-[3-(dimethylamino)propyl]-piperidin-1-yl]acetamide, 2-[4-[3-(dimethylamino)propyl]-piperidin-1-yl]ethanamine;

from 2-[3-[2-(piperidin-1-yl)ethyl]-piperidin-1-yl]acetonitrile in a yield of 90% of theory, 2-[3-[2-(piperidin-1-yl)ethyl]-piperidin-1-yl]ethanamine;

from 2-[3-[4-(dimethylamino)butyl]-piperidin-1-yl]acetonitrile in a yield of 94% of theory, 2-[3-[4-(dimethylamino)butyl]-piperidin-1-yl]ethanamine;

from 2-[3-[4-(pyrrolidin-1-yl)butyl]-piperidin-1-yl]acetonitrile in a yield of 96% of theory, 2-[3-[4-(pyrrolidin-1-yl)butyl]-piperidin-1-yl]ethanamine;

from 2-[3-[4-diethylamino)butyl]-piperidin-1-yl]acetonitrile in a yield of 86% of theory, 2-[2-[4-(diethylamino)butyl]-piperidin-1-yl]ethanamine;

from 2-[4-[4-(diethylamino)butyl]-piperidin-1-yl]acetamide, 2-[4-[4-(diethylamino)butyl]-piperidin-1-yl]ethanamine;

from 2-[4-[2-(diethylamino)ethyl]-piperidin-1-yl]acetamide in a yield of 94% of theory, 2-[4-[2-(diethylamino)ethyl]-piperidin-1-yl]ethanamine;

from 2-[3-[(dipropylamino)methyl]-piperidin-1-yl]acetonitrile in a yield of 98%, 2-[3-[(dipropylamino)methyl]-piperidin-1-yl]ethanamine, B.p.$_{0.035\ mm\ Hg}$ 95°–97° C.;

from 2-[3-[(hexahydro-1H-azepin-1-yl)methyl]piperidin-1-yl]acetonitrile in a yield of 93% of theory, 2-[3-[(hexahydro-1H-azepin-1-yl)methyl]-piperidin-1-yl]ethanamine, B.p.$_{0.03\ mm\ Hg}$ 109°–110° C.;

from 2-[3-[3-(piperidin-1-yl)propyl]-piperidin-1-yl]acetonitrile in a yield of 98% of theory, 2-[3-[3-(piperidin-1-yl)propyl]-piperidin-1-yl]ethanamine;

from 2-[3-[(piperidin-1-yl)methyl]-piperidin-1-yl]acetonitrile in a yield of 72% of theory, 2-[3-[(piperidin-1-yl)methyl]-piperidin-1-yl]ethanamine;

from 2-[3-[(diethylamino)methyl]-piperidin-1-yl]acetonitrile in a yield of 95% of theory, 2-8 3-[(diethylamino)-methyl]-piperidin-1-yl]ethanamine, B.p.$_{0.3\ mm\ Hg}$ 84°–85° C.;

from 2-[3-[(piperidin-1-yl)methyl]-pyrrolidin-1-yl]acetonitrile in a yield of 66% of theory, 2-[3-[(piperidin-1-yl)methyl]-pyrrolidin-1-yl]ethanamine, B.p.$_{12\ mm\ Hg}$ 135°–137° C.;

from 2-[3-[(dipropylamino)methyl]-pyrrolidin-1-yl]acetonitrile in a yield of 61% of theory, 2-[3-[(dipropylamino)methyl]-pyrrolidin-1-yl]ethanamine, B.p.$_{12\ mm\ Hg}$ 133°–136° C.;

from 2-[3-[[(cyclohexyl)methylamino]methyl]-pyrrolidin-1-yl]acetonitrile in a yield of 54% of theory, 2-[3-[[(cyclohexyl)methylamino]methyl]-pyrrolidin-1-yl]ethanamine, B.p.$_{5\ mm\ Hg}$ 160°–165° C.;

from 2-[4-[4-(piperidin-1-yl)butyl]-piperidin-1-yl]acetamide, 2-[4-[4-(piperidin-1-yl)butyl]-piperidin-1-yl]ethanamine, which was reacted without further purification, R$_F$ 0.3 (Macherey-Nagel, Polygram$^R$ SIL G/UV$_{254}$, pre-coated plastic sheets for TLC; eluant: dichloromethane/cyclohexane/methanol/conc. ammonia 68/15/15/2 v/v);

from 2-[4-[4-(dipropylamino)butyl]-piperidin-1-yl]acetamide, 2-[4-[4-(dipropylamino)butyl]-piperidin-1-yl]ethanamine;

from 2-[4-[3-[bis-(methylethyl)amino]propyl]piperidin-1-yl]-acetamide, 2-[4-[3-[bis-(methylethyl)amino]propyl]-piperidin-1-yl]ethanamine;

from 2-[4-[3-(piperidin-1-yl)propyl]-piperidin-1-yl]acetamide, 2-[4-[3-(piperidin-1-yl)propyl]-piperidin-1-yl]ethanamine;

from 2-[4-[3-(dipropylamino)propyl]-piperidin-1-yl]acetamide, 2-[4-[3-(dipropylamino)propyl]-piperidin-1-yl]ethanamine.

EXAMPLE O

2-[2-[(Diethylamino)methyl]-piperidin-1-yl]ethanamine 172 g (0.822 mol) of 2-[2-[(diethylamino)methyl]-piperidin-1-yl]acetonitrile were dissolved in 1300 ml of n-hexane and after the addition of 57.0 g Raney nickel and 300 ml of liquid ammonia, catalytically hydrogenated under a hydrogen pressure of 70 bar and at 90° C. in a shaking autoclave until the uptake of hydrogen had ended (about 12 hours). After the autoclave had been cooled and the pressure released, the catalyst was filtered off and the solvent was evaporated off. The residue remaining was purified by vacuum distillation. 152.0 g (87% of theory) of a colourless oil were obtained, B.p.$_{15\ mm\ Hg}$ 135°–138° C.

The following were obtained analogously:

from 2-[2-[(morpholin-4-yl)methyl]-piperidin-1-yl]acetonitrile in a yield of 55% of theory, 2-[2-[morpholin-4-yl)methyl]-piperidin-1-yl]ethanamine, B.p.$_{0.4\ mm\ Hg}$ 123°–124° C.;

from 2-[2-[4-(piperidin-1-yl)butyl]-piperidin-1-yl]acetonitrile in a yield of 42% of theory, 2-[2-[4-(piperidin-1-yl)butyl]-piperidin-1-yl]ethanamine, B.p.$_{0.1\ mm\ Hg}$ 130°–133° C.;

from 2-[2-[[(cyclopentyl)methylamino]methyl]-piperidin-1-yl]acetonitrile in a yield of 76% of theory, 2-[2-[[(cyclopentyl)methylamino]methyl]-piperidin-1-yl]ethanamine, B.p.$_{0.7\ mm\ Hg}$ 136°–140° C.;

from 2-[2-[[bis-(methylethyl)amino]methyl]-piperidin-1-yl]acetonitrile in a yield of 43% of theory, 2-[2-[[bis-(methylethyl)amino]methyl]-piperidin-1-yl]ethanamine, B.p.$_{21\ mm\ Hg}$ 158°–159° C.;

from 2-[2-[(butylethylamino)methyl]-piperidin-1-yl]acetonitrile in a yield of 61% of theory, 2-[2-[(butylethylamino)methyl]-piperidin-1-yl]ethanamine, B.p.$_{15\ mm\ Hg}$ 158°–160° C.;

from 2-[2-[(hexahydro-1H-azepin-1-yl)methyl]-piperidin-1-yl]-acetonitrile in a yield of 54% of theory, 2-[2-[(hexahydro-1H-azepin-1-yl)methyl]-piperidin-1-yl]ethanamine, B.p.$_{0.3\ mm\ Hg}$ 105°–107° C.;

from 2-[2-[(ethylpropylamino)methyl]-piperidin-1-yl]acetonitrile in a yield of 57% of theory, 2-[2-[(ethylpropylamino)methyl]-piperidin-1-yl]ethanamine, B.p.$_{10\ mm\ Hg}$ 144°–147° C.;

from 2-[3-[(diethylamino)methyl]-morpholin-4-yl]acetonitrile in a yield of 78% of theory, 2[3-[(diethylamino)-methyl]-morpholin-4-yl]ethanamine, R$_F$ 0.2 (Macherey-Nagel, Polygram$^R$ SIL G/UV$_{254}$, pre-coated plastic sheets for TLC, eluant: dichloromethane/cyclohexane/methanol/conc. ammonia/ethyl acetate 63/11.5/11.5/1.5/12.5 v/v);

from 4-[2-[(diethylamino)methyl]-piperidin-1-yl]butane nitrile in a yield of 99% of theory, 4-[2-[(diethylamino)-methyl]-piperidin-1-yl]butanamine, R$_F$ 0.19 (Macherey-Nagel, Polygram$^R$ SIL G/UV$_{254}$, pre-coated plastic sheets for TLC, eluant: dichloromethane/cyclohexane/methanol/conc. ammonia 102/23/23/3);

from 2-[2-[4-(diethylamino)butyl]-piperidin-1-yl]acetonitrile in a yield of 54% of theory, 2-[2-[4-(diethylamino)butyl]-piperidin-1-yl]ethanamine, B.p.$_{0.2\ mm\ Hg}$ 97°–99° C.;

from 2-[2-[(piperidin-1-yl)methyl]-piperidin-1-yl]acetonitrile in a yield of 38% of theory, 2-[2-[(piperidin-1-yl)methyl]-piperidin-1-yl]ethanamine, B.p.$_{0.1\ mm\ Hg}$ 87°–88° C.;

from 2-[2-[(dipropylamino)methyl]-piperidin-1-yl]acetonitrile in a yield of 40% of theory, 2-[2-[(dipropylamino)methyl]-piperidin-1-yl]ethanamine, B.p.$_{18\ mm\ Hg}$ 154°–156° C.;

from (−)-2-[2-[(diethylamino)methyl]-piperidin-1-yl]acetonitrile in a yield of 51% of theory, (−)-2-[2-[(diethylamino)methyl]-piperidin-1-yl]ethanamine, B.p.$_{18\ mm\ Hg}$ 143°–145° C., [α]$_D^{20}$ = −80.06° (ethanol);

from (+)-2-[2-[(diethylamino)methyl]-piperidin-1-yl]acetonitrile in a yield of 63% of theory, (+)-2-[2-[(diethylamino)methyl]-piperidin-1-yl]ethanamine, B.p.$_{16\ mm\ Hg}$ 142°–144° C., [α]$_D^{20}$ = +80.56° (ethanol);

from 2-[3-(diethylamino)-hexahydro-1H-azepin-1-yl]acetonitrile in a yield of 61% of theory, 2-[3-(diethylamino)hexahydro-1H-azepin-1-yl]ethylamine, bp.$_{17\ mm\ Hg}$ 143°–147° C.;

from 2-[(diethylamino)methyl]-1-(2-methyl-2-nitropropyl)-piperidine (prepared analogously to H. G. Johnson, J. Am. Chem. Soc. 68, 12 [1946]and G.H. Butler and F.N. McMillan, ibid. 72, 2978 [1950]) in a yield of 22% of theory, 2[2-[(diethylamino)methyl]-piperidin-1-yl]-1,1-dimethyl-ethanamine, B.p.$_{0.3\ mm\ Hg}$ 85°–92° C.;

from 2-[2-[(pyrrolidin-1-yl)methyl]-piperidin-1-yl]acetonitrile in a yield of 64% of theory, 2-[2-[(pyrrolidin-1-yl)methyl]-piperidin-1-yl]ethanamine, B.p.$_{20\ mm\ Hg}$ 156°–158° C.;

EXAMPLE P

11-[[[2-Bromo-ethyl]amino]carbonyl]-5,11-dihydro-6H-pyrido[2,3-b][1,4]benzodiazepin-6-one To a mixture of 5.0 g (0.0183 mol) of 11-(chlorocarbonyl)-5,11-dihydro-6H-pyrido[2,3-b][1,4]benzodiazepin-6-one, 50 ml of tetrahydrofuran, 4.08 g (0.02 mol) of 2-bromoethylammonium bromide and 7.0 g (0.051 mol) of anhydrous potassium carbonate were added 10 ml of water, whereupon the mixture heated up to 30°–35° C. on its own and was then stirred for 30 minutes without any external heating. Whereas initially all the solids had gone into solution temporarily, towards the end of the reaction a colourless precipitate had formed. The mixture was stirred into 400 ml of water, stirred for a further 30 minutes at ambient temperature and the product obtained was suction fitered. It was washed thoroughly with water and dried overnight in a circulating air dryer at 40° C. Yield 6.15 g (93% of theory) of colourless crystals, m.p. 217°–220° C. (D.).

The following were obtained analogously:

11-[[[2-Bromo-ethyl]amino]carbonyl]-9-chloro-5,11-dihydro-6H-pyrido[2,3-b][1,4]benzodiazepin-6-one in a yield of 67% of theory, the product was reacted further without purification, R$_F$ 0.72 (Macherey-Nagel, Polygram$^R$ SIL G/UV$_{254}$, pre-coated plastic sheets for TLC, eluant: dichloromethane/cyclohexane/methanol/conc. ammonia 68/15/15/2 v/v);

11-[[[2-Bromo-propyl]amino]carbonyl]-5,11-dihydro-6H-pyrido[2,3-b][1,4]benzodiazepine in a yield of 96% of theory, colourless cyrstals, m.p. 139°–140° C., R$_F$ 0.8 (Macherey-Nagel, Plygram$^R$ SIL G/UV$_{254}$, pre-coated plastic sheets for TLC, eluant: dichloromethane/cyclohexane/methanol/conc. ammonia 68/15/15/2 v/v);

4-[[[2-Bromo-ethyl]amino]carbonyl]-4,9-dihydro-3-methyl-10H-thieno[2,4-b]][1,5]benzodiazepin-10-one in a yield of 54% of theory, colourless crystals, m.p. 218° C., R$_F$ 0.70 (Macherey-Nagel, Polygram$^R$ SIL G/UV$_{254}$, pre-coated plastic sheets for TLC, eluant: ethyl acetate/cyclohexane/methanol/conc. ammonia 80/10/10/1 v/v).

PREPARATION OF THE END PRODUCTS

EXAMPLE 1

11-[[[2-[2-[(Diethylamino)methyl]-piperidin-1-yl]ethyl]amino]carbonyl]-5,11-dihydro-6H-pyrido[2,3-b][1,4]benzodiazepin-6-one hydrochloride A mixture of 33.4 g (0.122 mol) of 11-(chlorocarbonyl)-5,11-dihydro-6H-pyrido[2,3-b][1,4]benzodiazepin-6-one, 28.0 g (0.131 mol) of 2-[2-[(diethylamino)methyl]piperidin-1-yl]ethanamine and 730 ml of anhydrous acetonitrile was stirred for 3 hours at a reaction temperature of 45° C. After standing for 1 hour in an ice bath, the precipitate formed was suction filtered and washed with ice cold acetonitrile. It was dissolved in 400 ml of hot ethanol, 4.6 g of activated charcoal were added, the mixture was filtered whilst hot and the filtrate was evaporated down in vacuo. The residue remaining was dissolved in 150 ml of hot propan-2-ol and stirred at a temperature of 75° C. for 2 hours after the careful addition of 800 ml of ethyl acetate. The mixture was then left to stand for 2 hours at ice bath temperature, the crystals produced were suction filtered and thoroughly washed three times with 20 ml aliquots of ethyl acetate. 37.0 g (62% of theory) of colourless crystals were obtained, m.p. 200°–202° C.

EXAMPLE 2

11-[[[2-[2-[(Diethylamino)methyl]-piperidin-1-yl]ethyl]amino]carbonyl]-5,11-dihydro-6H-pyrido[2,3-b][1,4]benzodiazepin-6-one 3.2 g (0.0117 mol) of 11-(chlorocarbonyl)-5,11-dihydro-6H-pyrido[2,3-b][1,4]benzodiazepin-6-one and 1.27 g (0.012 mol) of anhydrous sodium carbonate were heated to 60° C. for 4 hours in 100 ml of dry acetonitrile together with 3.0 g (0.014 mol) of 2-[2-[(diethylamino)methyl]-piperidin-1-yl]ethanamine with stirring. The mixture was filtered while hot, the filtrate was cooled and the substance which crystallised out was suction filtered. 2.7 g (51% of theory) of colourless cyrstals were obtained, m.p. 175°–176° C.

EXAMPLE 3

11-[[[3-[2-[(Diethylamino)methyl]-piperidin-1-yl]propyl]amino]carbonyl]-5,11-dihydro-6H-pyrido[2,3-b][1,4]benzodiazepin-6-one Prepared analogously to Example 2 from 11-(chlorocarbonyl)-5,11-dihydro-6H-pyrido[2,3-b][1,4]benzodiazepin-6-one and 3-[2-[(diethylamino)methyl]-piperidin-1-yl]propanamine in a yield of 47% of theory. Colourless crystals, m.p. 160°–161° C. (acetonitrile).

EXAMPLE 4

5,11-Dihydro-11-[[[2-[2-[(dimethylamino)methyl]-piperidin-1-yl]ethyl]amino]carbonyl]-6H-pyrido[2,3-b][1,4]benzodiazepin-6-one Prepared analogously to Example 2 from 11-(chlorocarbonyl)-5,11-dihydro-6H-pyrido[2,3-b][1,4]benzodiazepin-6-one and 2-[2-[(dimethylamino)methyl]-piperidin-1-yl]ethanamine in a yield of 53% of theory. Colourless crystals, m.p. 189–190 (acetonitrile).

EXAMPLE 5

5,10-Dihydro-5-[[[3-[2-[(dimethylamino)methyl]-piperidin-1-yl]propyl]amino]carbonyl]-11H-dibenzo[b,e][1,4]diazepin-11-one Prepared analogously to Example 2 from 5-(chlorocarbonyl)-5,10-dihydro-11H-dibenzo[b,e][1,4]diazepin-11-one and 3-[2-[(dimethylamino)methy]-piperidin-1-yl]propanamine in a yield of 80% of theory. Colourless crystals, m.p. 131°–133° C. (diisopropyl ether).

EXAMPLE 6

5,11-Dihydro-11-[[[3-[2-[(dimethylamino)methyl]-piperidin-1-yl]propyl]amino]carbonyl]-6H-pyrido[2,3-b][1,4]benzodiazepin-6-one Prepared analogously to Example 2 from 11-chlorocarbonyl-5,11-dihydro-6H-pyrido[2,3-b][1,4]enzodiazepin-6-one and 3-[2-[(dimethylamino)methyl]-piperidin-1-yl]-propanamine in a yield of 54% of theory. Colourless crystals, m.p. 160°–162° C. (acetonitrile).

EXAMPLE 7

5-[[[2-[2-[(Diethylamino)methy]-piperidin-1-yl]ethyl]amino]carbonyl]-5,10-dihydro-11H-dibenzo[b,e][1,4]-diazepin-11-one Prepared analogously to Example 2 from 5-(chlorocarbonyl)-5,10-dihydro-11H-dibenzo[b,e][1,4]diazepin-11-one and 2-[2-[(diethylamino)methyl]-piperidin-1-yl]-ethanamine in a yield of 74% of theory. Colourless crystals, m.p. 123°–125° C. (diisopropylether).

EXAMPLE 8

5-[[[3-[2-[(Diethylamino)methyl]-piperidin-1-yl]propyl]amino]carbonyl]-5,10-dihydro-11H-dibenzo[b,e][1,4]diazepin-11-one Prepared analogously to Example 2 from 5-chlorocarbonyl-5,10-dihydro-11H-dibenzo[b,e][1,4]diazepin-11-one and 3-[2-[(diethylamino)methyl]-piperidin-1-yl]propanamine in a yield of 54% of theory, m.p. 148.0°–149.5° C. (diisopropylether). Soluble in water.

EXAMPLE 9

5,10-Dihydro-5-[[[2-[2-[(dimethylamino)methyl]-piperidin-1-yl]ethyl]amino]carbonyl]-11H-dibenzo[b,e][1,4]diazepin-11-one Prepared analogously to Example 2 from 5-(chlorocarbonyl)-5,10-dihydro-11H-dibenzo[b,e][1,4]diazepin-11-one and 2-[2-[(dimethylamino)methyl]-piperidin-1-yl]ethanamine in a yield of 73% of theory. Colourless crystals, m.p. 152°–154° C. (diisopropylether).

EXAMPLE 10

11-[[[2-[2-[2-(Diethylamino)ethyl]-piperidin-1-yl]ethyl]amino]carbonyl]-5,11-dihydro-6H-pyrido[2,3-b][1,4]benzodiazepin-6-one Prepared analogously to Example 2 from 11-(chlorocarbonyl-5,11-dihydro-6H-pyrido[2,3-b][1,4]benzodiazepin-6-one and 2-[2-[2-(diethylamino)ethyl]-piperidin-1-yl]ethanamine in a yield of 65% of theory. Colourless crystals, m.p. 161°–162° C. (acetonitrile).

EXAMPLE 11

11-[[[2-[2-[3-(Diethylamino)propyl]-piperidin-1-yl]ethyl]amino]carbonyl]-5,11-digydro-6H-pyrido[2,3-b][1,4]benzodiazepin-6-one Prepared analogously to Example 2 from 11-(chlorocarbonyl)-5,11-dihydro-6H-pyrido[2,3-b][1,4]benzodiazepin-6-one and 2-[2-[3-(diethylamino)propyl]-piperidin-1-yl]ethanamine in a yield of 58% of theory. Colourless crystals, m.p. 157°–158° C. (acetonitrile).

EXAMPLE 12

5,11-Dihydro-11-[[[2-[2-[3-(dimethylamino)propyl]-piperidin-1-yl]ethyl]amino]carbonyl]-6H-pyridol[2,3-b][1,4]benzodiazepin-6-one Prepared analogously to Example 2 from 11-(chlorocarbonyl)-5,11-dihydro-6H-pyrido[2,3-b][1,4]benzodiazepin-6-one and 2-[2-[3-(dimethylamino)propyl]-piperidin-1-yl]ethanamine in a yield of 61% of theory. Colourless crystals, m.p. 154°–155° C. (acetonitrile).

EXAMPLE 13

D,L-11-[[[4-[2-[(Diethylamino)methyl]-piperidin-1-yl]butyl]amino]carbonyl]-5,11-dihydro-6H-pyrido[2,3-b][1,4]benzodiazepin-6-one Prepared analogously to Example 2 from 11-(chlorocarbonyl)-5,11-dihydro-6H-pyrido[2,3-b][1,4]benzodiazepin-6-one and 4-[2-[(diethylamino)methyl]-piperidin-1-yl]butanamine in a yield of 90% of theory. Colourless crystals, m.p. 136°–137° C. (acetonitrile).

EXAMPLE 14

D,L-5,11-Dihydro-11-[[[2-[2-[2-(dimethylamino)ethyl]-piperidin-1-yl]ethyl]amino]carbonyl]-6H-pyrido[2,3-b][1,4]benzodiazepin-6-one Prepared analogously to Example 2 from 11-(chlorocarbonyl)-5,11-dihydro-6H-pyridol[2,3-b][1,4]benzodiazepin-6-one and 2-[2-[2-(dimethylamino)ethyl]piperidin-1-yl]ethanamine in a yield of 48% of theory. Colourless crystals, m.p. 158°–159° C. (acetonitrile).

EXAMPLE 15

D,L-11-[[[2-[2-[(Diethylamino)methyl]-piperidin-1-yl]ethyl]methylamino]carbonyl]-5,11-dihydro-6H-pyrido[2,3-b][1,4]benzodiazepin-6-one Prepared analogously to Example 2 from 11-(chlorocarbonyl)-5,11-dihydro-6H-pyrido[2,3-b][1,4]benzodiazepin-6-one and 2-[2-[(diethylamino)methyl]-piperidin-1-yl]-N-methyl-ethanamine in a yield of 54% of theory. Colourless crystals, m.p. 68°–70° C. (petroleum ether).

EXAMPLE 16

D,L-5,11-Dihydro-11-[[[2-[2-(dimethylamino)methy]-piperidin-1-yl]ethyl]methylamino]carbonyl]-6H-pyrido[2,3-b][1,4]benzodiazepin-6-one Prepared analogously to Example 2 from 11-(chlorocarbonyl)-5,11-dihydro-6H-pyrido[2,3-b][1,4]benzodiazepin-6-one and 2-[2-[(dimethylamino)methyl]-piperidin-1-yl]-N-methyl-ethanamine in a yield of 19% of theory. Colourless crystals, m.p. 64°–67° C. (petroleum ether).

EXAMPLE 17

(R,S)-11-[[[6-[2-[(Diethylamino)methyl]-piperidin-1-yl]hexyl]amino]carbonyl]-5,11-dihydro-6H-pyrido[2,3-b][1,4]benzodiazepin-6-one Prepared analogously to Example 2 from 11-(chlorocarbonyl)-5,11-dihydro-6H-pyrido[2,3-b][1,4]benzodiazepin-6-one and 6-[2-[(diethylamino)methyl]-piperidin-1-yl]hexanamine in a yield of 56% of theory. Colourless crystals, m.p. 111°–112° C. (acetonitrile).

EXAMPLE 18

Trans-5,11-Dihydro-11-[[[2-[2-[[(4-hydroxy-cyclohexyl)methylamino]methyl]-piperidin-1-yl]ethyl]methylamino]carbonyl]-6H-pyrido[2,3-b][1,4]benzodiazepin-6-one Prepared analogously to Example 2 from 11-(chlorocarbonyl)-5,11-dihydro-6H-pyrido[2,3-b][1,4]benzodiazepin-6-one and trans-2-[2-[[(4-hydroxy-cyclohexyl)methylamino]methyl]-piperidin-1-yl]-N-

EXAMPLE 19

D,L-11-[[[2-[2-[2-(Diethylamino)ethyl]-piperidin-1-yl]ethyl]methylamino]carbonyl]-5,11-dihydro-6H-pyrido[2,3-b][1,4]benzodiazepin-6-one Prepared analogously to Example 2 from 11-(chlorocarbonyl)-5,11-dihydro-6H-pyrido[2,3-b][1,4]benzodiazepin-6-one and 2-[2-[2-(diethylamino)ethyl]-piperidin-1-yl]-N-methyl-ethanamine in a yield of 37% of theory. Colourless crystals, m.p. 111°-113° C. (after recrystallisation from diisopropyl ether/acetonitrile 1/1 v/v and from acetonitrile).

EXAMPLE 20

D,L-5,11-Dihydro-11-[[[4-[2-[(dimethylamino)methyl]-piperidin-1-yl]butyl]amino]carbonyl]-6H-pyrido[2,3-b][1,4]benzodiazepin-6-one Prepared analogously to Example 2 from 11-(chlorocarbonyl-5,11-dihydro-6H-pyrido[2,3-b][1,4]benzodiazepin-6-one and 4-[2-[(dimethylamino)-methyl]-piperidin-1-yl]butanamine in a yield of 14% of theory. Colourless crystals, m.p. 126°-128° C. (ethyl acetate/diisopropyl ether 1/1 v/v) soluble in water.

EXAMPLE 21

D,L-trans-5,11-dihydro-11-[[[2-[2-[[(4-hydroxy-cyclohexyl)-methylamino]methyl]-piperidin-1-yl]ethyl]amino]carbonyl]-6H-pyrido[2,3-b][1,4]benzodiazepin-6-one Prepared analogously to Example 2 from 11-(chlorocarbonyl)-5,11-dihydro-6H-pyrido[2,3-b][1,4]benzodiazepin-6-one and trans-2-[2 -[[(4-hydroxy-cyclohexyl)methylamino]methyl]-piperidin-1-yl]ethanamine in a yield of 75% of theory. Colourless crystals, m.p. 130°-133° C. (acetonitrile/ethyl acetate 1/1 v/v).

EXAMPLE 22

4-[[[2-[2-[(Diethylamino)methyl]-piperidin-1-yl]ethyl]amino]carbonyl]-4,9-dihydro-3-methyl-10H-thieno[3,4-b][1,5]benzodiazepin-10-one Prepared analogously to Example 2 from 4-(chlorocarbonyl)-4,9-dihydro-3-methyl-10H-thieno[3,4-b][1,5]benzodiazepin-10-one and 2-[2-[(diethylamino)-methyl]-piperidin-1-yl]ethanamine in a yield of 39% of theory. Colourless cystals, m.p. 138°-140° C. (acetonitrile).

EXAMPLE 23

9-Chloro-11-[[[2-[2-[(diethylamino)methyl]-piperidin-1-yl]ethyl]amino]carbonyl]-5,11-dihydro-6H-pyrido[2,3-b][1,4]benzodiazepin-6-one Prepared analogously Example 2 from 9-chloro-11-(chlorocarbonyl-5,11-dihydro-6H-pyrido[2,3-b][1,4]benzodiazepin-6-one and 2-[2-[(diethylamino)methyl]-piperidin-1-yl]ethanamine in a yield of 60% of theory. Colourless crystals, m.p. 171°-173° C. (acetonitrile).

methyl-ethanamine in a yield of 24% of theory. Colourless, substantially amorphous solid substance with an approximate m.p. 105°-120° C. M.p. of the hydrochloride 210°-213° C. (D.) (acetone/isopropanol).

EXAMPLE 24

5,11-Dihydro-11-[[[2-[2-[2-(dimethylamino)ethyl]-piperidin-1-yl]ethyl]methylamino]carbonyl]-6H-pyrido[2,3-b][1,4]benzodiazepin-6-one Prepared analogously to Example 2 from 11-(chlorocarbonyl)-5,11-dihydro-6H-pyrido[2,3-b][1,4]benzodiazepin-6-one and 2-[2-[2-(dimethylamino)ethyl]-piperidin-1-yl]-N-methyl-ethanamine in a yield of 52% of theory. Colourless crystals, m.p. 114°-116° C. (after recrystallisation from diisopropylether and acetonitrile and decoction with water).

EXAMPLE 25

11-[[[2-[2-[(Diethylamino)methyl]-piperidin-1-yl]ethyl]amino]carbonyl]-5,11-dihydro-8-methyl-6H-pyrido[2,3-b][1,4]benzodiazepin-6-one Prepared analogously to Example 2 from 11-(chlorocarbonyl)-5,11-dihydro-8-methyl-6H-pyrido[2,3-b][1,4]benzodiazepin-6-one and 2-[2-[(diethylamino)methyl]-piperidin-1-yl]ethanamine in a yield of 55% of theory. Colourless crystals, m.p. 148°-150° C. (acetonitrile).

EXAMPLE 26

D,L-5,11-Dihydro-11-[[[4-[2-[(dimethylamino)methyl]-piperidin-1-yl]butyl]methylamino]carbonyl]-6H-pyrido[2,3-b][1,4]benzodiazepin-6-one Prepared analogously to Example 2 from 11-(chlorocarbonyl)-5,11-dihydro-6H-pyrido[2,3-b][1,4]benzodiazepin-6-one and 4-[2-[(dimethylamino)-methyl]-piperidin-1-yl]-N-methyl-butanamine in a yield of 73% of theory. Colourless amorphous substance: $R_F$ 0.25 (Macherey-Nagel, Polygram$^R$ SIL G/UV$_{254}$, pre-coated plastic sheets for TLC, eluant: dichloromethane/ethyl acetate/cyclohexane/methanol/conc. ammonia 58/25/8/1 v/v).

$C_{26}H_{36}N_6O_2$ (464.61) Calculated: C 67.21 H 7.81 N 18.09, Found: 67.35 7.85 17.70, IR (CH$_2$Cl$_2$) N—H 3370, C=O 1665 cm$^{-1}$.

UV (ethanol): $\lambda_{max}$ 282, shoulder at 224 nm $^1$H-NMR-(CDCl$_3$/CD$_3$OD); 400 MHz): 8.25 (1H-dd, J=5.2 and 2 Hz, α–pyridyl-H);

8.15 (1H-dd, J=7.6 and 1 Hz, ar. H in the 7-position),
7.79 (1H-dd, J=7.6 and 2 Hz, γ-pyridyl-H);
7.61-7.53 (2H-m, ar. H);
7.38-7.31 (1H-m, ar. H);
7.26 (1H-dd, J=7.6 and 5.2 Hz, β-pyridyl-H);
4.27 (1H-s, broad, exchangeable H);
3.23-3.13 (2H-m, aliph. H);
2.91-2.82 (1H-m, aliph. H);
2.83-2.74 (1H-m, aliph. H);
2.59 (3H-s,

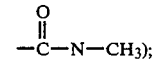

2.55-2.15 (5H-m, aliph. H);
2.23 (6H-s; —N(CH$_3$)$_2$);
1.90-1.25 (10H-m, aliph. H).

EXAMPLE 27

11-[[[2-[3-[(Diethylamino)methyl]-morpholin-4-yl]ethyl]amino]carbonyl]-5,11-dihydro-6H-pyrido[2,3-b][1,4]benzodiazepin-6-one Prepared analogously to Example 2 from 11-(chlorocarbonyl)-5,11-dihydro-6H-pyrido[2,3-b][1,4]benzodiazepin-6-one and 2-[3-[(diethylamino)methyl]-morpholin-4-yl]ethanamine in a yield of 67% of theory. Colourless crystals, m.p. 150°–151° C. (acetonitrile).

EXAMPLE 28

11-[[[4-[2-[(Diethylamino)methyl]-piperidin-1-yl]butyl]-methylamino]carbonyl]-5,11-dihydro-6H-pyrido[2,3-b][1,4]benzodiazepin-6-one Prepared analogously to Example 2 from 11-chlorocarbonyl)-5,11-dihydro-6H-pyrido[2,3-b][1,4]benzodiazepin-6-one and 4-[2-[diethylamino)methyl]-piperidin-1-yl]-N-methyl-butanamine in a yield of 44% of theory. Colourless amorphous substance.

$C_{28}H_{40}N_6O_2$ (492.66): Calculated: C 68.26 H 8.18 N 17.06. Found: 68.20 8.20 16.87.

IR ($CH_2Cl_2$): N—H 3375, C=O 1670 cm$^{-1}$
UV (ethanol): $\lambda_{max}$ 283, shoulder at 230 nm.
$^1$H-NMR (400 MHz, $CDCl_3/CD_3OD$): δ8.25 (1H-dd, J=5.2, and 2 Hz, α-pyridyl-H);
8.16 (1H-dd, J=7.6 and 1 Hz, ar H in the 7-position);
7.79 (1H-dd, J=7.6 and 2 Hz, γ-pyridyl-H);
7.61–7.53 (2H-m, ar. H);
7.37–7.31 (1H-m, ar. H);
7.25 (1H-dd, J=7.6 and 5.2 Hz, β-pyridyl-H);
4.15 (1H-s, broad, exchangeable H);
3.25–3.11 (2H-m, aliph. H);
2.95–2.85 (1H-m, aliph. H);
2.83–2.71 (1H-m, aliph. H);
2.58 (3H-s,

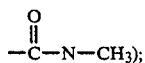

1.95–1.82 (1H-m, aliph. H);
1.75–1.23 (10H-M, aliph. H);
1.02 (6H-t, J=3.4 Hz, N—C—CH$_3$).

EXAMPLE 29

5,11-Dihydro-11-[[[2-[2-[(dipropylamino)methyl]-piperidin-1-yl]ethyl]amino]carbonyl]-6H-pyrido[2,3-b][1,4]benzodiazepin-6-one Prepared analogously to Example 2 from 11-(chlorocarbonyl)-5,11-dihydro-6H-pyrido[2,3-b][1,4]benzodiazepin-6-one and 2-[2-[(dipropylamino)methyl]-piperidin-1-yl]ethanamine in a yield of 88% of theory. Colourless crystals, m.p. 165° C. (acetonitrile).

EXAMPLE 30

5,11-Dihydro-11-[[[2-[2-[(dipropylamino)methyl]-piperidin-1-yl]ethyl]amino]carbonyl]-6H-pyrido[2,3-b][1,4]benzodiazepin-6-one methanesulphonate To a suspension of 56.2 g (0.1174 mol) of 5,11-dihydro-11-[[[2-[2-[(dipropylamino)methyl]-piperidin-1-yl]ethyl]amino]carbonyl]-6H-pyrido[2,3-b][1,4]benzodiazepin-6-one in a mixture of 100 ml of acetonitrile and 100 ml of ethyl acetate, a solution of 11.3 g (0.1176 mol) of methanesulphonic acid in 74 ml of acetonitrile was added dropwise whilst cooling with ice and stirring. After removal of the ice bath the mixture was heated to 70° C., 574 ml of acetic acid were added dropwise to the now clear solution, the mixture was inoculated with a crystal of the desired salt, left to cool to 40° C. and stirred for 2 hours at this temperature, then heated up to 50° C., 280 ml of ethyl acetate were again slowly added dropwise and after removal of the heating bath the mixture was stirred for 2 hours at ambient temperature, left to stand for 14 hours and finally the crystals formed were suction filtered. After washing with ethyl acetate and drying in a circulating air dryer, 64.0 g (95% of theory) of colourless crystals were obtained, m.p. 165°–167° C.

$C_{27}H_{38}N_6O_2 \cdot CH_3SO_3H$ (574.74): Calculated: C 58.52 H 7.37 N 14.62 S 5.58. Found: 58.62 6.95 14.60 5.73. Found: 58.53 7.41 14.68 5.69.

EXAMPLE 31

5,11-Dihydro-11-[[[2-[2-[(dipropylamino)methyl]-piperidin-1-yl]ethyl]amino]carbonyl]-6H-pyrido[2,3-b][1,4]benzodiazepin-6-one hydrochloride Prepared analogously to Example 1 from 11-(chlorocarbonyl)-5,11-dihydro-6H-pyrido[2,3-b][1,4]benzodiazepin-6-one and 2-[2-[(dipropylamino)methyl]-piperidin-1-yl]ethanamine in a yield of 87% of theory. Colourless crystals, m.p. 197°–199° C., not readily soluble in water.

EXAMPLE 32

8-Chloro-11-[[[2-[2-[(diethylamino)methyl]-piperidin-1-yl]ethyl]amino]carbonyl]-5,11-dihydro-6H-pyrido[2,3-b][1,4]benzodiazepin-6-one A mixture of 3.1 g (0.01 mol) of 8-chloro-11-(chlorocarbonyl)-5,11-dihydro-6H-pyrido[2,3-b][1,4]benzodiazepin-6-one, 2.6 g (0.0122 mol) of 2-[2-[(diethylamino)methy]-piperidin-1-yl]ethanamine and 310 ml of 1,2-dichloroethane was stirred for 2½ hours at ambient temperature, then extracted exhaustively with dilute hydrochloric acid. The combined aqueous extracts were made alkaline with saturated aqueous potassium carbonate solution and extracted exhaustively with dichloromethane. The dichloromethane phases were combined, dried over sodium sulphate with the addition of 1 g of animal charcoal and evaporated down in vacuo. After being triturated with diisopropylether the oily residue became crystalline and was recrystallised from acetonitrile. 2.9 g (60% of theory) of colourless crystals were obtained, m.p. 138°–140° C.

EXAMPLE 33

11-[[[2-[2-[(Diethylamino)methyl]-piperidin-1-yl]ethyl]amino]carbonyl]-5,11-dihydro-8-ethyl-6H-pyrido[2,3-b][1,4]benzodiazepin-6-one Prepared analogously to Example 2 from 11-(chlorocarbonyl)-5,11-dihydro-8-ethyl-6H-pyrido[2,3-b][1,4]benzodiazepin-6-one and 2-[2-[(diethylamino)methyl]-piperidin-1-yl]ethanamine in a yield of 70% of theory. Colourless crystals, m.p. 124°–126° C. (diisopropylether).

EXAMPLE 34

8-Bromo-11-[[[2-[2-[(diethylamino)methyl]-piperidin-1-yl]ethyl]amino]carbonyl]-5,11-dihydro-6H-pyrido[2,3-b][1,4]benzodiazepin-6-one Prepared analogously to Example 2 from 8-bromo-11-(chlorocarbonyl)-5,11-dihydro-6H-pyrido[2,3- b][1,4]benzodiazepin-6-one and 2-[2-[(diethylamino)methyl]-piperidin-1-yl]ethanamine in a yield of 25% of theory. Colourless crystals, m.p. 117°–119° C., $R_F$ 0.3 (Macherey-Nagel, Polygram$^R$ SIL G/UV$_{254}$, pre-coated plastic sheets for TLC, eluant: dichloromethane/ethyl acetate/cyclohexane/methanol/conc. ammonia 58/25/8/8/1 v/v).

EXAMPLE 35

11-[[[2-[2-[(Diethylamino)methyl]-piperidin-1-yl]ethyl]amino]carbonyl]-5,11-dihydro-9-methyl-6H-pyrido[2,3-b][1,4]benzodiazepin-6-one Prepared analogously to Example 2 from 11-(chlorocarbonyl)-5,11-dihydro-9-methyl-6H-pyrido[2,3-b][1,4]benzodiazepin-6-one and 2-[2-[(diethylamino)methyl]-piperidin-1-yl]ethanamine in a yield of 40% of theory. Colourless crystals, m.p. 183°–185° C. (acetonitrile).

EXAMPLE 36

11-[[[2-[2-[4-(Diethylamino)butyl]-piperidin-1-yl]ethyl]amino]carbonyl]-5,11-dihydro-6H-pyrido[2,3-b][1,4]benzodiazepin-6-one Prepared analogously to Example 2 from 11-(chlorocarbonyl)-5,11-dihydro-6H-pyrido[2,3-b][1,4]benzodiazepin-6-one and 2-[2-[4-(diethylamino)butyl]-piperidin-1-yl]ethanamine in a yield of 55% of theory. Colourless crystals, m.p. 155°–157° C. (acetonitrile). $R_F$ 0.57 (Macherey-Nagel, Polygram$^R$ SIL G/UV$_{254}$, pre-coated plastic sheets for TLC, eluant: dichloromethane/cyclohexane/methanol/conc. ammonia 102/23/23/3 v/v).

EXAMPLE 37

6,11-Dihydro-11-[[[2-[2-[(dipropylamino)methyl]-piperidin-1-yl]ethyl]amino]carbonyl]-5H-pyrido[2,3-b][1,5]benzodiazepin-5-one Prepared analogously to Example 2 from 11-(chlorocarbonyl)-6,11-dihydro-5H-pyrido[2,3-b][1,5]benzodiazepin-5-one and 2-[2-[(dipropylamino)methyl]-piperidin-1-yl]ethanamine in a yield of 66% of theory. Colourless crystals, m.p. 149°–151° C. (acetonitrile).

EXAMPLE 38

11-[[[2-[2-[(Diethylamino)methyl]-piperidin-1-yl]ethyl]amino]carbonyl]-6,11-dihydro-5H-pyrido[2,3-b][1,5]benzodiazepin-5-one Prepared analogously to Example 2 from 11-(chlorocarbony)-6,11-dihydro-5H-pyrido[2,3-b][1,5]benzodiazepin-5-one and 2-[2-[(diethylamino)methyl]-piperidin-1-yl]ethanamine in a yield of 52% of theory. Colourless crystals, m.p. 146°–147.5° C. (acetonitrile).

EXAMPLE 39

5,11-Dihydro-11-[[[2-[2-[(piperidin-1-yl)methyl]-piperidin-1-yl]ethyl]amino]carbonyl]-6H-pyrido[2,3-b][1,4]benzodiazepin-6-one hydrochloride Prepared analogously to Example 1 from 11-(chlorocarbonyl)-5,11-dihydro-6H-pyrido[2,3-b][1,4]benzodiazelpin-6-one and 2-[2-[(piperidin-1-yl)methyl]-piperidin-1-yl]ethanamine in a yield of 51% of theory. Colourless crystals, m.p. 214°–216° C. (acetonitrile), soluble in water.

EXAMPLE 40

11-[[[2-[3-(Diethylamino)-hexahydro-1H-azepin-1-yl]ethyl]amino]carbonyl]-5,11-dihydro-6H-pyrido[2,3-][1,4]benzodiazepin-6-one Prepared analogously to Example 2 from 11-(chlorocarbonyl)-5,11-dihydro-6h-pyrido[2,3-b][1,4]benzodiazepin-6-one and 2-[3-(diethylamino)hexahydro-1H-azepin-1-yl]ethanamine in a yield of 38% of theory. Colourless crystals, m.p. 164° C. (acetonitrile).

EXAMPLE 41

4-[[[2-[2-[(Diethylamino)methyl]-piperidin-1-yl]ethyl]amino]carbonyl]-1,3-dimethyl-1,4,9,10-tetrahydropyrazolo[4,3-e]pyrido[2,3-b][1,4]diazepin-10-one Prepared analogously to Example 2 from 4-(chlorocarbonyl)-1,3-dimethyl-1,4,9,10-tetrahydropyrazolo[4,3-e]pyrido[2,3-b][1,4]diazepin-10-one and 2-[2-[(diethylamino)methyl]-piperidin-1-yl]ethanamine in a yield of 17% of theory. Colourless crystals, m.p. 138°–139° C. (acetonitrile).

EXAMPLE 42

11-[[[2-[4-[(Diethylamino)methyl]-piperidin-1-yl]ethyl]amino]carbonyl-5,11-dihydro-6H-pyrido[2,3-b][1,4]benzodiazepin-6-one Prepared analogously to Example 2 from 11-(chlorocarbonyl)-5,11-dihydro-6H-pyrido[2,3-b][1,4]benzodiazepin-6-one and 2-[4-[(diethylamino)methyl]-piperidin-1-yl]ethanamine in a yield of 78% of theory. Colourless crystals, m.p. 171° C. (acetonitrile).

EXAMPLE 43

5,11-Dihydro-11-[[[2-[4-[2-(piperidin-1-yl)ethyl]-piperidin-1-yl]ethyl]amino]carbonyl]-6H-pyrido[2,3-b][1,4]benzodiazepin-6-one hydrochloride Prepared analogously to Example 1 from 11-(chlorocarbonyl)-5,11-dihydro-6H-pyrido[2,3-b][1,4]benzodiazepin-6-one and 2-[4-[2-(piperidin-1-yl)ethyl]-piperidin-1-yl]ethanamine in a yield of 50% of theory. Colourless crystals, m.p. 223° C. (D.) (acetonitrile).

EXAMPLE 44

11-[[[2-[4-[2-(Diethylamino)ethyl]-piperidin-1-yl]ethyl]amino]carbonyl]-5,11-dihydro-6H-pyrido[2,3-b][1,4]benzodiazepin-6-one Prepared analogously to Example 2 from 11-(chlorocarbonyl)-5,11-dihydro-6H-pyrido[2,3-b][1,4]benzodiazepin-6-one and 2-[4-[2-(diethylamino)ethyl]-piperidin-1-yl]ethanamine in a yield of 10% of theory. Colourless crystals, m.p. 170°–172° C. (ethyl acetate).

EXAMPLE 45

11-[[[2-[4-[3-(Diethylamino)propyl]-piperidin-1-yl]ethyl]amino]carbonyl]-5,11-dihydro-6H-pyrido[2,3-b][1,4]benzodiazepin-6-one Prepared analogously to Example 2 from 11-(chlorocarbonyl)-5,11-dihydro-6H-pyrido[2,3-b][1,4]benzodiazepin-6-one and 2[4-[3-(diethylamino)propyl]-piperidin-1-yl]ethanamine in yield of 92% of theory. Colourless crystals, m.p. 165°–166° C. (ethyl acetate).

EXAMPLE 46

11-[[[2-[2-[2-(Diethylamino)ethyl]-pyrrolidin-1-yl]ethyl]amino]carbonyl]-5,11-dihydro-6H-pyrido[2,3-b][1,4]benzodiazepin-6-one To a solution of 1.4 g (0.0051 mol) of 11-(chlorocarbonyl)-5,11-dihydro-6h-pyrido[2,3-b][14]benzodiazepin-6-one and 0.6 g (0.0059 mol) of triethylamine in 20 ml of anhydrous dimethylformamide, 1.06 g (0.005 mol) of 2-[2-[2-(diethylamino)ethyl]-pyrrolidin-1-yl]ethanamine was added dropwise and the mixture was then stirred for 1 hour at ambient temperature. The dimethylformamide was distilled off in vacuo, the residue remaining was made alkaline with sodium hydroxide solution and extracted with dichloromethane. The combined dichloromethane extracts were dried, evaporated down and finally purified by column chromatography on silica gel (70–230 mesh) using dichloromethane/methanol/conc. ammonia 70/29/1 v/v) as eluant. The combined eluates were freed from solvent, the residue was triturated with diisopropylether, the resulting crystals were then recrystallised from ethyl acetate using animal charcoal. 0.6 g (27% of theory) of colourless crystals were obtained, m.p. 127°–128° C.

EXAMPLE 47

D,L-11-[[[2-[2-[(Diethylamino)methyl]-pyrrolidin-1-yl]ethyl]amino]carbonyl]-5,11-dihydro-6H-pyrido[2,3-b][1,4]benzodiazepin-6-one Prepared analogously to Example 46 from 11-(chlorocarbonyl)-5,11-dihydro-6H-pyrido[2,3-b][1,4]benzodiazepin-6-one and 2-[2-[(diethylamino)methyl]-pyrrolodin-1-yl]ethanamine in a yield of 47% of theory. Colourless crystals, m.p. 160° C. (ethyl acetate/diisopropyl ether 1:1 v/v). The hydrochloride melted at 163°–165° C.

EXAMPLE 48

D,L-5-[[[2-[2-[(Diethylamino)methyl]-pyrrolidin-1-yl]ethyl]amino]carbonyl]-5,10-dihydro-1H-dibenzo[b,e][1,4]diazepin-11-one Prepared analogously to Example 46 from 5-(chlorocarbonyl)-5,10-dihydro-11H-dibenzo[b,e][1,4-]diazepin-11-one and 2-[2-[(diethylamino)methyl]-pyrrolidin-1-y]ethanamine in a yield of 23% of theory. Colourless crystals, m.p. 112°–115° C. (ethyl acetate).

The following were obtained analogously:
D,L-11-[[[2-[3-[[(cyclohexyl)methylamino]methyl]-pyrrolidin-1-yl]ethyl]amino]carbonyl]-5,11-dihydro-6H-pyrido[2,3-b][1,4]benzodiazepin-6-one;
9-chloro-11-[[[2-[3-[(diethylamino)methyl]-pyrrolidin-1-yl]ethyl]amino]carbonyl]-5,11-dihydro-6H-pyrido[2,3-b][1,4]benzodiazepin-6-one;
4-[[[2-[3-[(diethylamino)methyl]-pyrrolidin-1-yl]ethyl]amino]carbonyl]-4,9-dihydro-1,3-dimethyl-10H-thieno[3,4-b][1,5]benzodiazepin-10-one.

EXAMPLE 49

4-[[[2-[2-[(Diethylamino)methyl]-piperidin-1-yl]ethyl]amino]carbonyl]-1,3-dimethyl-1,4,9,10-tetrahydropyrrolo[3,2-b][1,5]benzodiazepin-10-one Prepared analogously to Example 2 from 4-(chlorocaboonyl)-1,3-dimethyl-1,4,9,10-tetrahydro-pyrrolo[3,2-b][1,5]benzodiazepin-10-one and 2-[2-[(diethylamino)methyl]-piperidin-1-yl]ethanamine in a yield of 72% of theory.

EXAMPLE 50

3-Chloro-4-[[[2-[2-[(dipropylamino)methyl]-piperidin-1-yl]ethyl]amino]carbonyl]-1-methyl-1,4,9,10-tetrahydro-pyrrolo[3,2-b][1,5]benzodiazepin-10-one Prepared analogously to Example 2 from 3-chloro-4-(chlorocarbonyl)-1-methyl-1,4,9,10-tetrahydro-pyrrolo[3,2-b][1,5]benzodiazepin-10-one and 2-[2-[(dipropylamino)methyl]-piperidin-1-yl]ethanamine in a yield of 57% of theory.

EXAMPLE 51

4-[[[2-[2-[(Dipropylamino)methyl]-piperidin-1-yl]ethyl]amino]carbonyl]-1-methyl-1,4,9,10-tetrahydro-pyrrolo[3,2-b][1,5]benzodiazepin-10-one 4.2 g (8.15 mol) of 3-chloro-4-[[[2-[2-[(dipropylamino)methyl]-piperidin-1-yl]ethyl]amino]carbonyl]-1-methyl-1,4,9,10-tetrahydro-pyrrolo[3,2-b][1,5]benzodiazepin-10-one were dissolved in 350 ml of hot ethanol and after the addition of 3 g of palladium on animal charcoal (20%), the mixture was hydrogenated for 20 hours under a hydrogen pressure of 50 bar and at a temperature of 40° C. The catalyst was filtered off, the filtrate was evaporated down in vacuo, the residue was taken up in 20 ml of water, the solution obtained was made alkaline with sodium hydroxide and extracted exhaustively with dichloromethane. The combined extracts were dried over sodium sulphate and evaporated down and the residue remaining was crystallised once from ethyl acetate and once from acetonitrile. 2.1 g (54% of theory) of colourless crystals were obtained, m.p. 153°–155° C.

EXAMPLE 52

4-[[[2-[3-[(Dipropylamino)methyl]-piperidin-1-yl]ethyl]amino]carbonyl]-1-methyl-1,4,9,10-tetrahydro-pyrrolo[3,2-b][1,5]benzodiazepin-10-one 5.02 g (9.7 mmol) of 3-chloro-4-[[[2-[2-[(dipropylamino)methyl]-piperidin-1-yl]ethyl]amino]carbonyl]-1-methyl-1,4,9,10-tetrahydro-pyrrolo[3,2-b][1,5]benzodiazepin-10-one were dissolved in a mixture of 5 ml of 85% formic acid and 25 ml of dimethylformamide and after the addition of 0.5 g of 10% palladium/activated charcoal the mixture was refluxed for 3 hours. 7.0 ml of formic acid was added, the mixture was refluxed for a further 6 hours and, after the addition of a further 4.0 ml of formic acid and 0.8 g of 10% palladium/activated charcoal, it was finally refluxed for a further 8 hours. The mixture was filtered while hot, the filtrate was evaporated down in vacuo and the residue was purified by column chromatography (silica gel; dichloromethane/ethyl acetate/methanol/conc. ammonia 3.5/1.5/0.46/0.06 v/v). 1.8 g (39% of theory) of colourless crystals were obtained, m.p. 153°–155° C. (acetonitrile) which were found by thin layer chromatography and IR, UV and $^1$H-NMR spectra, to be identical to a preparation obtained according to Example 51.

EXAMPLE 53

4-[[[2-[2-[(Dipropylamino)methyl]-piperidin-1-yl]ethyl]amino]carbonyl]-1-methyl-1,4,9,10-tetrahydro-pyrrolo[3,2-b][1,5]benzodiazepin-10-one A mixture of 5.15 g (0.01 mol) of 3-chloro-4-[[[2-[(dipropylamino)methyl]-piperidin-1-yl]ethyl]amino]carbonyl]-1-methyl-1,4,9,10-tetrahydro-pyrrolo[3,2-b][1,5]benzodiazepin-10-one, 83.3 mg (0.001 mol) of 2:1-tris(o-tolyl)-phosphine-palladium acetate catalyst, 2.025 g (0.044 mol) of formic acid and 5.77 g (0.057 mol) of triethylamine in 200 ml of tetrahydrofuran was heated to 100° C. in an autoclave for 40 hours under a nitrogen atmosphere. The mixture was filtered and evaporated down in vacuo, the residue was made alkaline with sodium hydroxide and extracted exhaustively with dichloromethane. The dried and evaporated organic phases were purified by column chromatography as in Example 52. 1.75 g (36% of theory) of colourless crystals were obtained, m.p. 154°–155° C. (acetonitrile), found according to thin layer chromatography and IR spectrum to be identical to a sample obtained according to Example 51.

EXAMPLE 54

11-[[[2-[2-(Diethylamino)methyl]-piperidin-1-yl]ethyl]-methylamino]carbonyl]-5,11-dihydro-6H-pyrido[2,3-b][1,4]benzodiazepin-6-one 9.66 g (0.0425 mol) of 2-[2-[(diethylamino)methyl]-piperidin-1-yl]-N-methyl-ethylamine are added dropwise to a mixture consisting of 22.5 ml of a 20% solution of phosgene in toluene, 100 ml of dioxane and 4.75 g (0.045 mol) of anydrous sodium carbonate, with external cooling with ice. The mixture is stirred for a further 60 minutes at ambient temperature, then 9.0 g (0.0428 mol) of 5,11-dihydro-6H-pyrido[2,3-b][1,4]benzodiazepin-6-one are added to the reaction mixture which is then refluxed for 4 hours. The mixture is filtered, the filtrate is evaporated down in vacuo and the product obtained is purified by column chromatography on 500 g of silica gel using ethyl acetate/methanol (ratio by volume 10:2) as eluant. After recrystallisation from cyclohexane, the colourless crystals melted at 269°–270° C. and were identical, according to their mixed melting point, thin layer chromatograph and IR spectrum, to a preparation prepared according to Example 15. Yield: 6.0 g (30% of theory).

The following were obtained analogously:

5,11-dihydro-11-[[[2-[2-[(dimethylamino)methyl]-piperidin-1-yl]ethyl]amino]carbonyl]-6H-pyrido[2,3-b][1,4]benzodiazepin-6-one, colourless crystals, m.p. 64°–67° C. (petroleum-ether);

trans-5,11-dihydro-11-[[[2-[2-[[(4-hydroxy-cyclohexyl)-methylamino]methyl]-piperidin-1-yl]ethyl]methlamino]carbonyl]-6H-pyrido[2,3-b][1,4]benzodiazepin-6-one, which melted at 211–213° C. (D) (from acetone/isopropanol 1/1 v/v) after being converted into the hydrochloride;

11-[[[2-[2-(diethylamino)ethyl]-piperidin-1-yl]ethyl]methylamino]carbonyl]-5,11-dihydro-6H-pyrido[2,3-b][1,4]benzodiazepin-6-one, colourless cyrstals m.p. 111°–113° C. (acetonitrile);

5,11-dihydro-11-[[[2-[2-(dimethylamino)ethyl]-piperidin-1-yl]ethyl]methylamino]carbonyl]-6H-pyrido[2,3-b][1,4]benzodiazepin-6-one, colourless crystals m.p. 114°–116° C. (diisopropylether);

5,11-dihydro-11-[[[4-[2-[(dimethylamino)methyl]-piperidin-1-yl]butyl]methylamino]carbonyl]-6H-pyrido[2,3-b][1,4]benzodiazepin-6-one, identical, according to thin layer chromatography, IR and $^1$H-NMR, to a prepartion prepared according to Example 26.

EXAMPLE 55

5,11-Dihydro-11-[[[2-[3-[(piperidin-1-yl)methyl]-piperidin-1-yl]ethyl]amino]carbonyl]-6H-pyrido[2,3-b][1,4]benzodiazepin-6-one Prepared analogously to Example 46 from 11-(chlorocarbonyl)-5,11-dihydro-6H-pyrido[2,3-b][1,4]benzodiazepin-6-one and 2-[3-[(piperidin-1-yl)methyl]-piperidin-1-yl]ethanamine in a yield of 38% of theory. Colourless amorphous substance, $R_F$ 0.16 (Macherey-Nagel, Polygram ® SIL G/UV$_{254}$, precoated plastic sheets for TLC, eluant: dichloromethane/methanol/conc. ammonia 90/10/1 v/v).

$C_{26}H_{34}N_6O_2 \cdot 2$ HCl (535.54): Calculated: C 58.31 H 6.78 Cl 13.24 N 15.69. Found 58.14 6.98 13.10 15.51.

IR (KBr): N—H 3420 cm$^{-1}$ (broad), C=O 1680 cm$^{-1}$

UV (ethanol): $\lambda_{max}$ 278, shoulder at 230 nm $^1$H-NMR-(400 MHz; DMSO-d$_6$/CD$_3$OD):
δ8.42–8.35 (1H-m; α-pyridyl-H);
7.99–7.78 (2H-m; ar. H);
7.71–7.63 (1H-m; ar. H);
7.62–7.43 (3H-m; ar.H);
4.60–4.30 (2H, broad; exchangeable H);
4.03–3.90 (1H-m; aliph. H);
3.65–3.35 (6H-m; aliph. H);
3.30–3.12 91H-m; aliph. H);
3.09–2.70 (6H-m; aliph. H);
2.65–2.42 (1H-m; aliph. H);
2.02–1.65 (8H-m; aliph. H);
1.50–1.20 (2H-m; aliph. H).

EXAMPLE 56

5,11-Dihydro-11-[[[2-[3-[3-(piperidin-1-yl)propyl]-piperidin-1-yl]ethyl]amino]carbonyl]-6H-pyrido[2,3-b][1,4]benzodiazepin-6-one Prepared analogously to Example 46 from 11-(chlorocarbonyl)-5,11-dihydro-6H-pyrido[2,3-b][1,4]benzodiazepin-6-one and 2[3-[3-(piperidin-1-yl)propyl]-piperidin-1-yl]ethanamine in a yield of 14% of theory. Colourless amorphous substance, $R_F$ 0.13 (Macherey-Nagel, Polygram ® SIL G/UV$_{254}$, precoated plastic sheets for TLC, eluant: dichloromethane/methanol/conc. ammonia 90/10/1 v/v).

$C_{26}H_{38}N_6O_2$ (490.66): Calculated: C 68.54 H 7.81 N 17.13. Found: 68.30 7.96 17.05.

IR (KBr): N—H 3400 cm$^{-1}$ (broad), C=O 1675 cm$^{-1}$.

UV (ethanol): $\lambda_{max}$ 282, shoulder at 230 nm.

$^1$H-NMR- (CDCl$_3$/CD$_3$OD; 400 MHz): δ8.32 (1H-dd, J=4.4 Hz and 2 Hz, α-pyridyl-H);
7.91 (1H-dd, J=8.0 Hz and 1.6 Hz; ar. H in the 7-position;
7.67–7.59 (2H-m; ar. H);
7.52 (1H-dd J=9 and 1 Hz; ar. H);
7.48–7.41 (1H-m; ar. H);
7.37–7.32 (1H-dd; J=8.0 Hz and 4.4 Hz, β-pyridyl-H);
4.25 (2H-s, exchangeable h);
2.83–2.68 (1H-m, aliph. H);
2.55–2.35 (5H-m. aliph. H);
2.35–2.24 (3H-m, aliph. H);
1.98–1.87 (1H-m, aliph. H);
1.87–1.22 (16H-m; aliph. H).
1.22–1.05 (2H-m; aliph. H);
0.93–0.77 (1H-m; aliph. H).

EXAMPLE 57

11-[[[2-[3-(Diethylamino)methyl]-piperidin-1-yl]ethyl-]amino]carbonyl]-5,11-dihydro-6H-pyrido[2,3-b][1,4]benzodiazepin-1-one Prepared analogously to Example 46 from 11-(chlorocarbonyl)-5,11-dihydro-6H-pyrido[2,3-b][1,4]benzodiazepin-6-one and 2-[3-[(diethylamino)methyl]-piperidin-1-yl]ethanamine in a yield of 34% of theory. Colourless crystals, m.p. 139°–141° C. (acetonitrile), $R_F$ 0.11 (Macherey-Nagel, Polygram® SIL G/UV$_{254}$, pre-coated plastic sheets for TLC, eluant: dichloromethane/ethyl acetate/cyclohexane/methanol/conc. ammonia 58/25/8/8/1 v/v).

The following were obtained analogously:
from 4-(chlorocarbonyl)-1,3-dimethyl-1,4,9,10-tetrahydropyrazolo[4,3-b][1,5]benzodiazepin-10-one and 2-[2-[(diethylamino)methyl]-piperidin-1-yl]ethanamine, 4-[[[2-[2-[(diethylamino)methyl]-piperidin-1-yl]ethyl-]amino]carbonyl-1,3-dimethyl-1,4,9,10-tetrahydropyrazolo[4,3-b][1,5]benzodiazepin-10-one;
from 4-(chlorocarbonyl)-1-methyl-1,4,9,10-tetrahydropyrazolo[4,3-b][1,5]benzodiazepin-10-one and 2-[2-[(diethylamino)methyl]-piperidin-1-yl]ethanamine, 4-[[[2-[2-[(diethylamino)methyl]-piperidin-1-yl]ethyl-]amino]carbonyl]-1-methyl-1,4,9,10-tetrahydropyrazolo[4,3-b][1,5]benzodiazepin-10-one.

EXAMPLE 58

5,11-Dihydro-11-[[[2-[3-[(dipropylamino)methyl]-piperidin-1-yl]ethyl]amino]carbonyl]-6H-pyrido[2,3-b][1,4]benzodiazepin-6-one Prepared analogously to Example 46 from 11-(chlorocarbonyl)-5,11-dihydro-6H-pyrido[2,3-b][1,4]benzodiazepin-6-one and 2-[3-[(dipropylamino)-methyl]-piperidin-1-yl]ethanamine in a yield of 48% of theory. Colourless crystals, m.p. 153°–155° C. (acetonitrile).

EXAMPLE 59

5,11-Dihydro-11-[[[2-[3-[(hexahydro-1H-azepin-1-yl)methyl]-piperidin-1-yl]ethyl]amino]carbonyl]-6H-pyrido[2,3-b][1,4]benzodiazepin-6-one Prepared analogously to Example 46 from 11-(chlorocarbonyl)-5,11-dihydro-6H-pyrido[2,3-b][1,4]benzodiazepin-6-one and 2[3-[(hexahydro-1H-azepin-1-yl)methyl]-piperidin-1-yl]ethanamine in a yield of 69% of theory. Colourless crystals, m.p. 135°–137° C. (acetonitrile).

EXAMPLE 60

9-Chloro-11-[[[2-[3-[(diethylamino)methyl]-piperidin-1-yl]-ethyl]amino]carbonyl]-5,11-dihydro-6H-pyrido[2,3-b][1,4]benzodiazepin-6-one Prepared analogously to Example 46 from 9-chloro-11-(chlorocarbonyl)-5,11-dihydro-6H-pyrido[2,3-b][1,4]benzodiazepin-6-one and 2-[3-[(diethylamino)methyl]-piperidin-1-yl]ethanamine in a yield of 73% of theory. Colourless crystals, m.p. 125° C. (D.) (acetonitrile).

EXAMPLE 61

11-[[[2-[3-[(Diethylamino)methyl]-piperidin-1-yl]ethyl-]amino]carbonyl]-5,11-dihydro-6H-pyrido[2,3-b][1,4]benzodiazepin-6-one Prepared analogously to Example 2 from 11-(chlorocarbonyl)-5,11-dihydro-6H-pyrido[2,3-b][1,4]benzodiazepin-6-one and 2-[3-[(diethylamino)methyl]-pyrrolidin-1-yl]ethanamine in a yield of 32% of theory. Colourless crystals, m.p. 184°–185° C. (acetonitrile).

EXAMPLE 62

5,11-Dihydro-11-[[[2-[3-[(piperidin-1-yl)methyl]-pyrrolidin-1-yl]ethyl]amino]carbonyl]-6H-pyrido[2,3-b][1,4]benzodiazepin-6-one Prepared analogously to Example 2 from 11-(chlorocarbonyl)-5,11-dihydro-6H-pyrido[2,3-b][1,4]benzodiazepin-6-one and 2-[3-[(piperidin-1-yl)methyl]-pyrrolidin-1-yl]ethanamine in a yield of 39% of theory. Colourless crystals, m.p. 168°–169° C. (acetonitrile).

EXAMPLE 63

5,11-Dihydro-11-[[[2-[3-[(dipropylamino)methyl]-pyrrolidin-1-yl]ethyl]amino]carbonyl]-6H-pyrido[2,3-b][1,4]benzodiazepin-6-one Prepared analogously to Example 2 from 11-(chlorocarbonyl)-5,11-dihydro-6H-pyrido[2,3-b][1,4]benzodiazepin-6-one and 2-[3-[(dipropylamino)-methyl]-pyrrolidin-1-yl]ethanamine in a yield of 22% of theory. Colourless crystals, m.p. 134°–138° C. (acetonitrile).

EXAMPLE 64

9-Chloro-11-[[[2-[3-[(diethylamino)propyl]-piperidin-1-yl]-ethyl]amino]carbonyl] 5,11-dihydro-6H-pyrido[2,3-b][1,4]benzodiazepin-6-one Prepared analogously to Example 2 from 9-chloro-11-(chlorocarbonyl)-5,11-dihydro-6H-pyrido[2,3-b][1,4]benzodiazepin-6-one and 2-[4-[3-(diethylamino)-propyl]-piperidin-1-yl]ethanamine in a yield of 41% of theory. Colourless crystals, m.p. 168°–170° C. (ethyl acetate).

EXAMPLE 65

(+)-9-Chloro-11-[[[2-2-[(diethylamino)methyl]-piperidin-1-yl]ethyl]amino]carbonyl]-5,11-dihydro-6H-pyrido[2,3-b][1,4]benzodiazepin-6-one Prepared analogously to Example 2 from 9-chloro-11-(chlorocarbonyl)-5,11-dihydro-6H-pyrido[2,3-b][1,4]benzodiazepin-6-one and (+)-2-[2-[(diethylamino)methyl]-piperidin-1-yl]ethanamine in a yield of 50% of theory. Colourless crystals, m.p. 169°–170° C. (from acetonitrile, using activated charcoal); $[\alpha]_D^{20} = +11.88°$ (dilute hydrochloric acid).

EXAMPLE 66

(−)-9-Chloro-11-[[[2-2-[(diethylamino)methyl]-piperidin-1-yl]ethyl]amino]carbonyl]-5,11-dihydro-6H-pyrido[2,3-b][1,4]benzodiazepin-6-one Prepared analogously to Example 2 from 9-chloro-11-(chlorocarbonyl)-5,11-dihydro-6H-pyrido[2,3-b][1,4]benzodiazepin-6-one and (−)-2-[2-[(diethylamino)methyl]-piperidin-1-yl]ethanamine in a yield of 33% of theory. Colourless crystals, m.p. 169°–170° C. (acetonitrile); $[\alpha]_D^{20} = -11.92°$ (dilute hydrochloric acid).

EXAMPLE 67

5,11-Dihydro-11-[[[2-[2-[(pyrrolidin-1-yl)methyl]-piperidin-1-yl]ethyl]amino]carbonyl]-6H-pyrido[2,3-b][1,4]benzodiazepin-6-one Prepared analogously to Example 2 from 11-(chlorocarbonyl)-5,11-dihydro-6H-pyrido[2,3-b][1,4]benzodiazepin-6-one and 2-[2-[(pyrrolidin-1-yl)methyl]-piperidin-1-yl]ethanamine in a yield of 44% of theory. Colourless crystals, m.p. 198° C. (from acetonitrile using fuller's earth).

EXAMPLE 68

11-[[[2-[4-[3-[(Diethylamino)propyl]-piperidin-1-yl]ethyl]amino]carbonyl]-5,11-dihydro-9-methyl-6H-pyrido[2,3-b][1,4]benzodiazepin-6one Prepared analogously to Example 2 from 11-(chlorocarbonyl)-5,11-dihydro-9-methyl-6H-pyrido[2,3-b][1,4]benzodiazepin-6-one and 2-[4-[3-[(diethylamino)propyl]-piperidin-1-yl]ethanamine in a yield of 39% of theory. Colourless crystals, m.p. 172°–173° C. (acetonitrile).

EXAMPLE 69

11-[[[2-[3-[[(Cyclohexyl)methylamino]methyl]-pyrrolidin-1-yl]ethyl]amino]carbonyl]-5,11-dihydro-6H-pyrido[2,3-b][1,4]benzodiazepin-6-one Prepared analogously to Example 2 from 11-(chlorocarbonyl)-5,11-dihydro-6H-pyrido[2,3-b][1,4]benzodiazepin-6-one and 2-[3-[[(cyclohexyl)methylamino]methyl]-pyrrolidin-1-yl]ethanamine in a yield of 19% of theory. Colourless crystals, m.p. 166°–167° C. (ethyl acetate/methanol 1/1 v/v).

EXAMPLE 70

9-Chloro-11-[[[2-[4-[3-[(diethylamino)propyl]-piperidin-1-yl]-ethyl]amino]carbonyl]-5,11-dihydro-6H-pyrido[2,3-b][1,4]benzodiazepin-6-one Prepared analogously to Example 46 from 9-chloro-11-(chlorocarbonyl)-5,11-dihydro-6H-pyrido[2,3-b][1,4]benzodiazepin-6-one and 2-[4-[3-(diethylamino)-propyl]-piperidin-1-yl]ethanamine in a yield of 41% of theory. Colourless crystals, m.p. 168°–170° C.

EXAMPLE 71

5,11-Dihydro-11-[[[2-[4-[4-(piperidin-1-yl)butyl]-piperidin-1-yl]ethyl]amino]carbonyl]-6H-pyrido[2,3-b][1,4]benzodiazepin-6-one dihydrochloride Prepared analogously to Example 46 from 11-(chlorocarbonyl)-5,11-dihydro-6H-pyrido[2,3-b][1,4]benzodiazepin-6-one and 2-[4-[4-(piperidin-1-yl)butyl]-piperidin-1-yl]ethanamine in a yield of 40% of theory. The colourless dihydrochloride melted at 231°–233° C.

EXAMPLE 72

5,11-Dihydro-11-[[[2-[4-[3-(dipropylamino)propyl]-piperidin-1-yl]ethyl]amino]carbonyl]-9-methyl-6H-pyrido[2,3-b][1,4]benzodiazepin-6-one trihydrochloridedihydrate Prepared analogously to Example 1 from 11-(chlorocarbonyl)-5,11-dihydro-9-methyl-6H-pyrido[2,3-b][1,4]benzodiazepin-6-one and 2-[4-[3-(dipropylamino)propyl]-piperidin-1-yl]ethanamine in a yield of 63% of theory. Colourless crystals, m.p. 195° C. (D.), $R_F=0.5$ (Macherey-Nagel, Polygram® SIL G UV$_{254}$, pre-coated plastic sheets for TLC, eluant: dichloromethane/cyclohexane/methanol/conc. ammonia 68/15/15/2 v/v).

EXAMPLE 73

11-[[[2-[4-[3-[Bis(methylethyl)amino]propyl]-piperidin-1-yl]ethyl]amino]carbonyl]-5,11-dihydro-9-methyl-6H-pyrido[2,3-b][1,4]benzodiazepin-6-one Prepared analogously to Example 1 from 11-(chlorocarbonyl)-5,11-dihydro-9-methyl-6H-pyrido[2,3-b][1,4]benzodiazepin-6-one and 2-[4-[3-[bis(methylethyl)amino]propyl]-piperidin-1-yl]ethanamine in a yield of 46% of theory. Colourless crystals, m.p. 160°–162° C. (ethyl acetate).

EXAMPLE 74

5,11-Dihydro-11-[[[2-[4-[3-(piperidin-1-yl)propyl]-piperidin-1-yl]ethyl]amino]carbonyl]-6H-pyrido[2,3-b][1,4]benzodiazepin-6-one Prepared analogously to Example 1 from 11-(chlorocarbonyl)-5,11-dihydro-6H-pyrido[2,3-b][1,4]benzodiazepin-6-one and 2-[4-[3-(piperidin-1-yl)propyl)-piperidin-1-yl]ethanamine in a yield of 16% of theory. Colourless crystals, m.p. 192°–193° C. (acetonitrile).

EXAMPLE 75

5,11-Dihydri-9-methyl-11-[[[2-[4-[3-(piperidin-1-yl)propyl]-piperidin-1-yl]ethyl]amino]carbonyl]-6H-pyrido[2,3-b][1,4]benzodiazepin-6-one Prepared analogously to Example 1 from 11-(chlorocarbonyl)-5,11-dihydro-9-methyl-6H-pyrido[2,3-b][1,4]benzodiazeplin-6-one and 2-[4-[3-(piperidin-l-yl)propyl]-piperidin-l-yl]ethanamine in a yield of 20% of theory. Colourless crystals, m.p. 174°–175° C. (acetonitrile).

EXAMPLE 76

5,11-Dihydro-11-[[[2-[4-[3-(dipropylamino)propyl]-piperidin-l-yl]ethyl]amino]carbonyl]-6H-pyrido[2,3-b][1,4]benzodiazepin-6-one Prepared analogously to Example 1 from 11-(chlorocarbonyl)-5,11-dihydro-6H-pyrido[2,3-b][1,4]benzodiazepin-6-one and 2-[4-[3-(dipropylamino)propyl]-piperidin-l-yl]ethanamine in a yield of 43% of theory. Colourless crystals, m.p. 169°–170° C. (ethyl acetate).

EXAMPLE 77

11-[[[2-[4-[3-[Bis(methylethyl)amino]propyl]-piperidin-1-yl]ethyl]amino]carbonyl]-5,11-dihydro-6H-pyrido[2,3-b][1,4]benzodiazepin-6-one Prepared analogously to Example 1 from 11-(chlorocarbonyl)-5,11-dihydro-6H-pyrido[2,3-b][1,4]benzoidazepin-6-one and 2-[4-[3-[bis(methylethyl)amino]propyl]-piperidin-l-yl]ethanmine in a yield of 28% of theory. Colourless crystals, m.p. 184° C. (ethyl acetate).

EXAMPLE 78

9-Chloro-5,11-dihydro-11-[[[2-[4-[3-(dipropylamino)-propyl]-piperidin-1-yl]ethyl]amino]carbonyl]-6H-pyrido[2,3-b][1,4]benzodiazepin-6-one Prepared analogously to Example 1 from 9-chloro-11-(chlorocarbonyl)-5,11-dihydro-6H-pyrido[2,3-b][1,4]benzodiazepin-6-one and 2-[4-[3-(dipropylamino)propyl]-piperidin-1-yl]ethanamine in a yield of 22% of theory. Colourless crystals, m.p. 174°–175° C. (acetonitrile).

EXAMPLE 79

9-Chloro-5,11-dihydro-11-[[[2-[4-[3-(piperidin-1-yl)propyl]-piperidin-1-yl]ethyl]amino]carbonyl]-6H-pyrido[2,3-b][1,4]benzodiazepin-6-one Prepared analogously to Example 1 from 9-chloro-11-(chlorocarbonyl)-5,11-dihydro-6H-pyrido[2,3-b][1,4]benzodiazepin-6-one and 2-[4-[3-(piperidin-1-yl)propyl]-piperidin-1-yl]ethanamine in a yield of 10% of theory. Colourless crystals, m.p. 176°–177° C. (acetonitrile).

EXAMPLE 80

11-[[[2-[4-[3-[Bis(methylethyl)amino]propyl]-piperidin-1-yl]ethyl]amino]carbonyl]-9-chloro-5,11-dihydro-6H-pyrido[2,3-b][1,4]benzodiazepin-6-one Prepared analogously to Example 1 from 9-chloro-11-(chlorocarbonyl)-5,11-dihydro-6H-pyrido[2,3-b][1,4]benzodiazepin-6-one and 2-[4-[3-[bis(methylethyl)amino]propyl]-piperidin-1-yl]ethanamine in a yield of 44% of theory. Colourless crystals, m.p. 175°–176° C. (acetonitrile).

EXAMPLE 81

9-Chloro-5,11-dihydro-11-[[[2-[4-[(4-(piperidin-1-yl)butyl]-piperidin-1-yl]ethyl]amino]carbonyl]-6H-pyrido[2,3-b][1,4]benzodiazepin-6-one hydrochloride Prepared analogously to Example 46 from 9-chloro-11-(chlorocarbonyl)-5,11-dihydro-6H-pyrido[2,3-b][1,4]benzodiazepin-6-one and 2-[4-[4-(piperidin-1-yl)butyl]-piperidin-1-yl]ethanamine in a yield of 68% of theory. Colourless crystals, m.p. 173°–175° C. (ethyl acetate).

EXAMPLE 82

4-[[[2-[4-[3-(Dipropylamino)propyl]-piperidin-1-yl]ethyl]amino]carbonyl]-4,9-dihydro-3-methyl-10H-thieno[3,4-b][1,5]benzodiazepin-10-one Prepared analogously to Example 1 from 4-(chlorocarbonyl)-4,9-dihydro-3-methyl-10H-thieno[3,4-b][1,5]benzodiazepin-10-one and 2-[4-[3-(dipropylamino)propyl]-piperidin-1-yl]ethanamine in a yield of 42% of theory. Colourless crystals, m.p. 114°–115° C. (diisopropyl ether).

EXAMPLE 83

4-[[[2-[4-[3-(Diethylamino)propyl]-piperidin-1-yl]ethyl]amino]carbonyl]-4,9-dihydro-3-methyl-10H-thieno[3,4-b][1,5]benzodiazepin-10-one Prepared analogously to Example 1 from 4-(chlorocarbonyl)-4,9-dihydro-3-methyl-10H-thieno[3,4-b][1,5]benzodiazepin-10-one and 2-[4-[3-(diethylamino)propyl]-piperidin-1-yl]ethanamine in a yield of 52% of theory. Colourless crystals, m.p. 131°–133° C. (acetonitrile).

EXAMPLE 84

4,9-Dihydro-3-methyl-4-[[[2-[4-[3-(piperidin-1-yl)propyl]-piperidin-1-yl]ethyl]amino]carbonyl]-10H-thieno[3,4-b][1,5]benzodiazepin-10-one Prepared analogously to Example 1 from 4-(chlorocarbonyl)-4,9-dihydro-3-methyl-10H-thieno[3,4-b][1,5]benzodiazepin-10-one and 2-[4-[3-(piperidin-1-yl)propyl]-piperidin-1-yl]ethanamine in a yield of 9% of theory. Colourless crystals, m.p. 170°–171° C.

EXAMPLE 85

4,9-Dihydro-4-[[[2-[4-[3-(dimethylamino)propyl]-piperidin-1-yl]ethyl]amino]carbonyl]-3-methyl-10H-thieno[3,4-b][1,5]benzodiazepin-10-one Prepared analogously to Example 1 from 4-(chlorocarbonyl)-4,9-dihydro-3-methyl-10H-thieno[3,4-b][1,5]benzodiazepin-10-one and 2-[4-[3-(dimethylamino)propyl]-piperidin-1-yl]ethanamine in a yield of 17% of theory. Colourless crystals, m.p. >300° C. (t-butylmethyl ether).

EXAMPLE 86

4,9-Dihydro-3-methyl-4-[[[2-[4-[4-(piperidin-1-yl)butyl]-piperidin-1-yl]ethyl]amino]carbonyl]-10H-thieno[3,4-b][1,5]benzodiazepin-10-one Prepared analogously to Example 1 from 4-(chlorocarbonyl)-4,9-dihydro-3-methyl-10H-thieno[3,4-b][1,5]benzodiazepin-10-one and 2-[4-[4-(piperidin-1-yl)butyl]-piperidin-1-yl]ethanamine in a yield of 20% of theory. Colourless crystals, m.p. 186°–187° C. (acetonitrile).

EXAMPLE 87

5,11-Dihydro-11-[[[2-[3-[2-(piperidin-1-yl)ethyl]-piperidin-1-yl]ethyl]amino]carbonyl]-6H-pyrido[2,3-b][1,4]benzodiazepin-6-one dihydrochloride Prepared analogously to Example 46 from 11-(chlorocarbonyl)-5,11-dihydro-6H-pyrido[2,3-b][1,4]benzodiazepin-6-one and 2-[3-[2-(piperidin-1-yl)ethyl]-piperidin-1-yl]ethanamine in a yield of 43% of theory. The dihydrochloride melted at 204°–208° C.

EXAMPLE 88

5,11-Dihydro-11-[[[2-[3-[4-(dimethylamino)butyl]-piperidin-1-yl]ethyl]amino]carbonyl]-6H-pyrido[2,3-b][1,4]benzodiazepin-6-one Prepared analogously to Example 46 from 11-(chlorocarbonyl)-5,11-dihydro-6H-pyrido[2,3-b][1,4]benzodiazepin-6-one and 2-[3-[4-(dimethylamino)butyl]-piperidin-1-yl]ethanamine in a yield of 53% of theory. Colourless crystals, m.p. 119°–120° C.

EXAMPLE 89

5,11-Dihydro-11-[[[2-[3-[4-(pyrrolidin-1-yl)butyl]-piperidin-1-yl]ethyl]amino]carbonyl]-6H-pyrido[2,3-b][1,4]benzodiazepin-6-one dihydrochloride Prepared analogously to Example 46 from 11-(chlorocarbonyl)-5,11-dihydro-6H-pyrido[2,3-b][1,4]benzodiazepin-6-one and 2-[3-[4-(pyrrolidin-1-yl)butyl]-piperidin-1-yl]ethanamine in a yield of 35% of theory. The colourless dihydrochloride melted at 170°–172° C.; $R_F$ 0.69 (HPTLC ready-made silica gel plates 60 F₂₅₄ for Nano-TLC, Messrs Merck; eluant: dichloromethane/ethanol/conc. ammonia 65/30/5 v/v/v).

EXAMPLE 90

11-[[[2-[3-[4-(1-Diethylamino)butyl]-piperidin-1-yl]ethyl]amino]carbonyl]-5,11-dihydro-6H-pyrido[2,3-b][1,4]benzodiazepin-6-one Prepared analogously to Example 46 from 11-(chlorocarbonyl)-5,11-dihydro-6H-pyrido[2,3-b][1,4]benzodiazepin-6-one and 2-[3-[4-(diethylamino)butyl]-piperidin-1-yl]ethanamine in a yield of 41% of theory. The dihydrochloride, which could only be obtained in the form of a partially crystalline foam, melted at about 130° C.; $R_F$ 0.18 (Merck-TLC ready-made silica gel plates 60 F₂₅₄; eluant: dichloromethane/methanol/conc. ammonia 90/10/1 v/v).

IR (CH₂Cl₂): C=O 1670 cm⁻¹

UV (ethanol): $\lambda_{max}$ 280, shoulder at 240 nm

¹H-NMR (200 MHz, CDCl₃/CD₃OD): δ8.39 (1H-m, α-pyridyl-H); 7.40–6.93 (6H-m, ar. H); 4.30 (4H-s, exchanageable H); 3.75–3.55 (4H-m; aliph. H); 3.35–2.95 (8H-m; aliph. H); 2.95–2.40 (2H-m; aliph. H); 2.15–1.65 (7H-m; aliph. H); 1.60–1.25 (10H-m; aliph. H).

EXAMPLE 91

5,11-Dihydro-11-[[[2-[2-[(dipropylamino)methyl]-piperidin-1-yl]ethyl]amino]carbonyl]-6H-prido[2,3-][1,4]benzodiazepin-6-one dihydrochloride-hydrate 0.479 g (0.001 mol) of 5,11-dihydro-11-[[[2-[2-[(dipropylamino)methyl]-piperidin-1-yl]ethyl]amino]carbonyl]-6H-pyrido[2,3-][1,4]benzodiazepin-6-one were dissolved in 10 ml of anhydrous ethanol and combined with a solution of 0.002 mol of hydrogen chloride in isopropanol (0.43 ml of a solution containing 0.17 g of HCl per ml of isopropanol). The solvents were distilled off in vacuo and the residue was triturated with dry acetonitrile. The crystalline precipitate formed was suction filtered, thoroughly washed twice with 5 ml of fresh acetonitrile and dried in vacuo. M.p. 205°–207° C.

C₂₇H₃₈N₆O₂·2 HCl·H₂O (569.57): Calculated: C 56.94 H 7.43 Cl 12.45 N 14.75. Found: 56.35 7.29 12.67 14.91.

EXAMPLE 92

5,11-Dihydro-11-[[[2-[2-[(dipropylamino)methyl]-piperidin-1-yl]ethy]amino]carbonyl]-6H-pyrido[2,3-b][1,4]benzodiazepin-6-one hydrobromide A solution of 0.957 g (0.002 mol) of 5,11-dihydro-11-[[[2-[2-[(dipropylamino)methyl]-piperidin-1-yl]ethyl]amino]carbonyl]-6H-pyrido[2,3-b][1,4]benzodiazepin-6-one in 20 ml of ethanol was combined with 0.135 ml of a 45% aqueous hydrobromic acid solution (0.002 mol). The colourless salt mentioned above slowly crystallised out of the mixture and after being left to stand for 3 hours it was suction filtered, washed thoroughly three times with 3 ml of anhydrous ethanol and finally dried at 50° C. in a circulating air dryer.

C₂₇H₃₈N₆O₂·HBr (559.55): Calculated: C 57.96 H 7.02 Br 14.29 N 15.02, Found: 57.91 7.06 14.27 15.08.

EXAMPLE 93

5,11-Dihydro-11-[[[2-[2-[(dipropylamino)methyl]-piperidin-1-yl]ethyl]amino]carbonyl]-6H-pyrido[2,3-b][1,4]benzodiazepin-6-one sesquimaleate The salt obtained from corresponding quantities of 5,11-dihydro-11-[[[2-[2-[(dipropylamino)methyl]-piperidin-1-yl]ethyl]amino]carbonyl]-6H-pyrido[2,3-b][1,4]benzodiazepin-6-one and maleic acid in anhydrous ethanol melted at 134°–137° C.

C₂₇H₃₈N₆O₂×1.5 (C₄H₄O₄) (652.75): Calculated: C 60.72 H 6.79 N 12.87, Found: 60.07 6.88 12.68.

EXAMPLE 94

5,11-Dihydro-11-[[[2-[2-[(dipropylamino)methyl]-piperidin-1-yl]ethyl]amino]carbonyl]-6H-pyrido[2,3-b][1,4]benzodiazepin-6-one sulphate Prepared analogously to Example 91 but using an ethanolic solution of sulphuric acid instead of the isopropanolic hydrochloric acid solution. Colourless crystals, m.p. 165°–167° C. (from propan-2-ol/ethyl acetate).

C₂₇H₃₈N₆O₂·H₂SO₄ (576.71): Calculated: C 56.23 H 6.99 N 14.57 S 5.56, Found: 56.30 7.17 14.52 5.55.

EXAMPLE 95

11-[[[2-[2-[(Diethylamino)methyl]-piperidin-1-yl]ethyl]amino]carbonyl]-5,11-dihydro-8-ethyl-6H-pyrido[2,3-b][1,4]benzodiazepin-6-one Prepared analogously to Example 2 from 11-(chlorocarbonyl)-5,11-dihydro-8-ethyl-6H-pyrido[2,3-b][1,4]benzodiazepin-6-one and 2-[2-[(diethylamin)methyl]-piperidin-1-yl]ethanamine in a yield of 70% of theory. Colourless crystals, m.p. 124°–126° C. (diisopropyl ether).

EXAMPLE 96

5,11-Dihydro-11-[[[2-[2-[(morpholin-4-yl)methyl]-piperidin-1-yl]ethyl]amino]carbonyl]-6H-pyrido[2,3-b][1,4]benzodiazepin-6-one Prepared analogously to Example 2 from 11-(chlorocarbonyl)-5,11-dihydro-6H-pyrido[2,3-b][1,4]benzodiazepin-6-one and 2-[2-[(morpholin-4-yl)methyl]-piperidin-1-yl]ethanamine in a yield of 30% of theory. Colourless crystals, m.p. 167° C. (acetonitrile using fuller's earth).

EXAMPLE 97

5,11-Dihydro-11-[[[2-[2-[4-(piperidin-1-yl)butyl]-piperidin-1-yl]ethyl]amino]carbonyl]-6H-pyrido[2,3-b][1,4]benzodiazepin-6-one Prepared analogously to Example 2 from 11-(chlorocarbonyl)-5,11-dihydro-6H-pyrido[2,3-b][1,4]benzodiazepin-6-one and 2-[2-[4-(piperidin-1-yl)butyl]-piperidin-1-yl]ethanamine in a yield of 36% of theory. Colourless crystals, m.p. 154°–155° C. (acetonitrile).

EXAMPLE 98

11-[[[2-[2-[(Diethylamino)methyl]-piperidin-1-yl]-1,1-dimethyl-ethyl]amino]carbonyl]-5,11-dihydro-6H-pyrido[2,3-b][1,4]benzodiazepin-6-one Prepared analogously to Example 2 from 11-(chlorocarbonyl)-5,11-dihydro-6H-pyrido[2,3-b][1,4]benzodiazepin-6-one and 2-[2-[(diethylamino)methyl]-piperidin-1-yl]-1,1-dimethyl-ethanamine in a yield of 62% of theory. Colourless crystals, m.p. 160°–162° C. (acetonitrile and ethyl acetate).

EXAMPLE 99

11-[[[2-[2-[((Cyclopentyl)methylamino)methyl]-piperidin-1-yl]ethyl]amino]carbonyl]-5,11-dihydro-6H-pyrido[2,3-b][1,4]benzodiazepin-6-one Prepared analogously to Example 2 from 11-(chlorocarbonyl)-5,11-dihydro-6H-pyrido[2,3-][1,4]benzodiazepin-6-one and 2-[2-[((cyclopentyl)methylamino)methyl]-piperidin-1-yl]ethanamine in a yield of 63% of theory. Colourless crystals, m.p. 157°–158° C. (acetonitrile using activated charcoal).

EXAMPLE 100

(−)-4-[[[2-[2-[(Diethylamino)methyl]-piperidin-1-yl]ethyl]amino]carbonyl]-4,9-dihydro-3-methyl-10H-thieno[3,4-b][1,5]benzodiazepin-10-one Prepared analogously to Example 1 from 4-(chlorocarbonyl)-4,9-dihydro-3-methyl-10H-thieno[3,4-b][1,5]benzodiazepin-10-one and (−)-2-[2-[(diethylamino)methyl]-piperidin-1-yl]ethanamine in a yield of 53% of theory. Colourless crystals, m.p. 132°–133° C. (acetonitrile); $[\alpha]_D^{20} = -14.00°$ (dilute aqueous hydrochloric acid).

EXAMPLE 101

(+)-4-[[[2-[2-[(Diethylamino)methyl]-piperidin-1-yl]ethyl]amino]carbonyl]-4,9-dihydro-3-methyl-10H-thieno[3,4-b][1,5]benzodiazepin-10-one Prepared analogously to Example 1 from 4-(chlorocarbonyl)-4,9-dihydro-3-methyl-10H-thieno[3,4-b][1,5]benzodiazepin-10-one and (+)-2-[2-[(diethylamino)methyl]-piperidin-1-yl]ethanamine in a yield of 55% of theory. Colourless crystals, m.p. 131°–132° C. (acetonitrile); $[\alpha]_D^{20} = -13.66°$ (dilute aqueous hydrochloric acid).

EXAMPLE 102

11-[[[2-[2-[[Bis(methylethyl)amino]methyl]-piperidin-1-yl]ethyl]amino]carbonyl]-5,11-dihydro-6H-pyrido[2,3-b][1,4]benzodiazepin-6-one Prepared analogously to Example 1 from 11-(chlorocarbonyl)-5,11-dihydro-6H-pyrido[2,3-b][1,4]benzodiazepin-6-one and 2-[2-[[bis(methylethyl)amino]methyl]-piperidin-1-yl]ethanamine in a yield of 34% of theory. Colourless crystals, m.p. 181°–182° C. (acetonitrile using activated charcoal).

EXAMPLE 103

11-[[[2-[2-[(Butylethylamino)methyl]-piperidin-1-yl]ethyl]amino]carbonyl]-5,11-dihydro-6H-pyrido[2,3-b][1,4]benzodiazepin-6-one Prepared analogously to Example 1 from 11-(chlorocarbonyl)-5,11-dihydro-6H-pyrido[2,3-b][1,4]benzodiazepin-6-one and 2-[2-[(butylethylamino)-methyl]-piperidin-1-]ethanamine in a yield of 16% of theory. Colourless crystals, m.p. 156°–157° C. (acetonitrile).

EXAMPLE 104

5,11-Dihydro-11-[[[2-[2-[(hexahydro-1H-azepin-1-yl)methyl]-piperidin-1-yl]ethyl]amino]carbonyl]-6H-pyrido[2,3-b][1,4]benzodiazepin-6-one Prepared analogously to Example 2 from 11-(chlorocarbonyl)-5,11-dihydro-6H-pyrido[2,3-b][1,4]benzodiazepin-6-one and 2-[2-[(hexahydro-1H-azepin-1-yl)methyl]-piperidin-1-yl]ethanamine in a yield of 39% of theory. Colourless crystals, m.p. 156°–158° C. (acetonitrile).

EXAMPLE 105

6-Chloro-5,10-dihydro-5-[[[2-[2-[(dipropylamino)methyl]-piperidin-1-yl]ethyl]amino]carbonyl]-11H-dibenzo[b,e][1,4]diazepin-11-one Prepared analogously to Example 1 from 6-chloro-5-(chlorocarbonyl)-5,10-dihydro-11H-dibenzo[b,e][1,4]diazepin-11-one and 2-[2-[(dipropylamino)methyl]-piperidin-1-yl]ethanamine in a yield of 2.6% of theory. Colourless crystals, m.p. 71°–78° C., presumably a mixture of 2 diastereomers.

$C_{28}H_{38}ClN_5O_2$ (512.09): Calculated: C 65.67 H 7.48 Cl 6.92 N 13.66, Found: 65.69 774 13.60.

EXAMPLE 106

5,11-Diydro-11-[[[2-[2-[(ethylpropylamino)methyl]-piperidin-1-yl]ethyl]amino]carbonyl]-6H-pyrido[2,3-b][1,4]benzodiazepin-6-one Prepared analogously to Example 2 from 11-(chlorocarbonyl)-5,11-dihydro-6H-pyrido[2,3-b][1,4]benzodiazepin-6-one and 2-[2-[(ethylpropylamino)methyl]-piperidin-1-yl]ethanamine in a yield of 75% of theory. Colourless crystals, m.p. 160°–162° C. (acetonitrile).

EXAMPLE 107

(−)-5,11-Dihydro-11-[[[2-[2-[(dipropylamino)methyl]-piperidin-1-yl]ethyl]amino]carbonyl]-6H-pyrido[2,3-b][1,4]benzodiazepin-6-one Prepared analogously to Example 1 from 11-(chlorocarbonyl)-5,11-dihydro-6H-pyrido[2,3-b][1,4]benzodiazepin-6-one and (−)-2-[2-[(dipropylamino)methyl]-piperidin-1-yl]ethanamine in a yield of 90% of theory. Colourless crystals, m.p. 164°–165° C. (acetonitrile); $[\alpha]_D^{20} = -7.62°$ (dilute aqueous hydrochloric acid).

EXAMPLE 108

(+)-5,11-Dihydro-11-[[[2-[2-[(dipropylamino)methyl]-piperidin-1-yl]ethyl]amino]carbonyl]-6H-pyrido[2,3-b][1,4]benzodiazepin-6-one Prepared analogously to Example 2 from 11-(chlorocarbonyl)-5,11-dihydro-6H-pyrido[2,3-b][1,4]benzodiazepin-6-one and (+)-2-[2-[(dipropylamino)methyl]-piperidin-1-yl]ethanamine in a yield of 60% of theory. Colourless crystals, m.p. 164°–165° C. (acetonitrile); $[\alpha]_D^{20} = +7.24°$ (dilute aqueous hydrochloric acid).

EXAMPLE 109

5,11-Dihydro-11-[[[2-[2-[(dipropylamino)methyl]-piperidin-1-yl]ethyl]amino]carbonyl]-6H-pyrido[2,3-b][1,4]benzodiazepin-6-one The darkened mixture of 1.806 g (0.005 mol) of 11-[[[2-bromo-ethyl]amino]carbonyl]-5,11-dihydro-6H-pyrido[2,3-b][1,4]benzodiazepin-6-one, 0.992 g (0.005 mol) of 2-[(dipropylamino)-methyl]piperidine, 20 ml of anhydrous acetonitrile and 0.75 g (0.005 mol) of sodium iodide was refluxed for 4 hours with stirring under a nitrogen atmosphere. The mixture was left to cool, 50 ml of 10% aqueous potassium carbonate solution were added and the organic phase was separated off. The aqueous phase was extracted five times in all, with 10 ml aliquots of dichloromethane. The combined organic extracts were dried over sodium sulphate with the addition of animal charcoal and evaporated down in vacuo. The residue was purified by column chromatography on silica gel (30–60 microns) and using dichloromethane/cyclohexane/methanol/conc. ammonia 68/15/15/1 (v/v/v/v) as eluant. The corresponding eluates were evaporated down, the residue was recrystallised once from acetonitrile and dried in a vacuum dryer at 50° C. until a constant weight was obtained. 0.7 g (29% of theory) of colourless crystals were obtained, m.p. 163°–164° C., which were identical according to their mixed melting point, thin layer chromatogram and IR spectrum, to a preparation prepared according to Example 29.

EXAMPLE 110

4-[[[2-[4-(Diethylamino)butyl]-piperidin-1-yl]ethyl]amino]carbonyl]-4,9-dihydro-3-methyl-10H-thieno[3,4-b][1,5]benzodiazepin-10-one Prepared analogously to Example 109 from 4-[[[2-bromo-ethyl]amino]carbonyl]-4,9-dihydro-3-methyl-10H-thieno[3,4-b][1,5]benzodiazepin-10-one and 4-[4-(diethylamino)butyl]piperidine in a yield of 51% of theory. Colourless crystals, m.p. 130°–131° C.

EXAMPLE 111

4,9-Dihydro-4-[[[2-[4-[4-(piperidin-1-yl)butyl]-piperidin-1-yl]ethyl]amino]carbonyl]-3-methyl-10H-thieno[3,4-b][1,5]benzodiazepin-10-one Prepared analogously to Example 109 from 4-[[[2-bromo-ethyl]amino]carbonyl]-4,9-dihydro-3-methyl-10H-thieno[3,4-b][1,5]benzodiazepin-10-one and 4-[4-(piperidin-1-yl)butyl]piperidine in a yield of 20% of theory. Colourless crystals, m.p. 186°–187° C.

EXAMPLE 112

11-[[[2-[4-[4-(Diethylamino)butyl]-piperidin-1-yl]ethyl]amino]carbonyl]-5,11-dihydro-6H-pyrido[2,3-b][1,4]benzodiazepin-6-one Prepared analogously to Example 109 from 11-[[[2-bromo-ethyl]amino]carbonyl]-5,11-dihydro-6H-pyrido[2,3-b][1,4]benzodiazepin-6-one and 4-[4-(diethylamino)butyl]-piperidine, but using dimethylformamide instead of acetonitrile, in a yield of 60% of theory. Colourless crystals, m.p. 167° C. (ethyl acetate).

EXAMPLE 113

9-Chloro-11-[[[2-[4-[4-(diethylamino)butyl]-piperidin-1-yl]ethyl]amino]carbonyl]-5,11-dihydro-6H-pyrido[2,3-b][1,4]benzodiazepin-6-one Prepared analogously to Example 109 from 11-[[[2-bromo-ethyl]amino]carbonyl]-9-chloro-5,11-dihydro-6H-pyrido[2,3-b][1,4]benzodiazepin-6-one and 4-[4-(diethylamino)butyl]piperidine, but using dimethylformamide instead of acetonitrile, in a yield of 19% of theory. Colourless crystals, m.p. 157° C.

EXAMPLE 114

4,9-Dihydro-4-[[[2-[4-[3-(hexahydro-1H-azepin-1-yl)propyl]-piperidin-1-yl]ethyl]amino]carbonyl]-3-methyl-10H-thieno[3,4-b][1,5]benzodiazepin-10-one Prepared analogously to Example 109 from 4-[[[2-bromo-ethyl]amino]carbonyl]-4,9-dihydro-3-methyl-10H-thieno[3,4-b][1,5]benzodiazepin-10-one and 4-[3-(hexahydro-1H-azepin-1-yl)propyl]piperidine in a yield of 29% of theory. Colourless crystals m.p. 144°–145° C. $R_F$=0.5 (Macherey-Nagel, Polygram$^R$ SIL G/UV$_{254}$, pre-coated plastic sheets for TLC; eluant: dichloromethane/cyclohexane/methanol/conc. ammonia 68/15/15/2 v/v).

EXAMPLE 115

4,9-Dihydro-3-methyl-4-[[[2-[4-[3-(1-methyl-pyrrolidin-2-yl)propyl]-piperidin-1-yl]ethyl]amino]carbonyl]-10H-thieno[3,4-b][1,5]benzodiazepin-10-one Prepared analogously to Example 109 from 4-[[[2-bromo-ethyl]amino]carbonyl]-4,9-dihydro-3-methyl-10H-thieno[3,4-b][1,5]benzodiazepin-10-one and 4-[3-(1-methyl-pyrrolidin-2-yl)propyl]piperidine in a yield of 18% of theory. Colourless crystals, m.p. 145°–146° C. (from ethyl acetate/ethanol). $R_F$=0.5 (TLC investigation as in Example 114).

The preparation of some pharmaceutical forms for administration will now be described with reference to some Examples:

EXAMPLE I

Tablets containing 5 mg of 5,11-dihydro-11-[[[2-[2-[(dipropylamino)methyl]-piperidin-1-yl]ethyl]amino]carbonyl]-6H-pyrido[2,3-b][1,4]benzodiazepin-6-one methanesulphonate

| Composition: | |
|---|---|
| 1 tablet contains: | |
| Active substance | 5.0 mg |
| Lactose | 148.0 mg |
| Potato starch | 65.0 mg |
| Magnesium stearate | 2.0 mg |
| | 220.0 mg |

Method of preparation

A 10% mucilage is prepared from potato starch by heating. The active substance, lactose and remaining potato starch are added and granulated with the above mucilage through a screen with a mesh size of 1.5 mm. The granules are dried at 45° C., passed through the same screen again, mixed with magnesium stearate and compressed to form tablets.

Weight of tablet: 220 mg
Punch: 9 mm.

EXAMPLE II

Coated tablets containing 5 mg of 5,11-dihydro-11-[[[2-[2-[(dipropylamino)methyl]-piperidin-1-yl]ethyl]amino]carbonyl]-6H-pyrido[2,3-b][1,4]benzodiazepin-6-one methanesulphonate The tablets prepared in Example I are coated by known methods with a coating consisting essentially of sugar and talc. The finished coated tablets are polished with beeswax.

Weight of coated tablet: 300 mg.

EXAMPLE III

Ampoules containing 10 mg of 5,11-dihydro-11-[[[2-[2-[(dipropylamino)methyl]-piperidin-l-yl]ethyl]amino]carbonyl]-6H-pyrido[2,3-b][1,4]benzodiazepin-6-one methanesulphonate

| Composition: | |
|---|---|
| 1 ampoule contains: | |
| Active substance | 10.0 mg |
| Sodium chloride | 8.0 mg |
| Distilled water ad | 1 ml |

Method of preparation

The active substance and sodium chloride are dissolved in distilled water and then made up to the volume specified. The solution is filtered sterile and transferred into 1 ml ampoules.

Sterilisation: 20 minutes at 120° C.

EXAMPLE IV

Suppositories containing 20 mg of 5,11-dihydro-11-[[[2-[2-[(dipropylamino)methyl]-piperidin-l-yl]ethyl]amino]carbonyl]-6H-pyrido[2,3-b][1,4]benzodiazepin-6-one methanesulphonate

| Composition: | |
|---|---|
| 1 suppository contains: | |
| Active substance | 20.0 mg |
| Suppository mass | 1680.0 mg |
| (e.g. Witepsol W 45$^R$) | 1700.0 mg |

Method of preparation

The finely powdered active substance is suspended in the molten suppository mass which has been cooled to 40° C. At 37° C. the mass is poured into slightly chilled suppository moulds.

Weight of suppository 1.7 g.

EXAMPLE V

Drops containing 5,11-dihydro-11-[[[2-[2-[(dipropylamino)methyl]-piperidin-l-yl]ethyl]amino]carbonyl]-6H-pyrido[2,3-b][1,4]benzodiazepin-6-one methanesulphonate

| Composition: | |
|---|---|
| 100 ml of drops solution contain: | |
| Methyl p-hydroxybenzoate | 0.035 g |
| Propyl p-hydroxybenzoate | 0.015 g |
| Aniseed oil | 0.05 g |
| Menthol | 0.06 g |
| Pure ethanol | 10.0 g |
| Active substance | 0.5 g |
| Sodium cyclamate | 1.0 g |
| Glycerol | 15.0 g |
| Distilled water ad | 100.0 ml |

Method of preparation

The active substance and sodium cyclamate are dissolved in about 70 ml of water and glycerol is added. The p-hydroxybenzoates, aniseed oil and menthol are dissolved in ethanol and this solution is added to the aqueous solution with stirring. Finally, it is made up to 100 ml with water and filtered to remove suspended particles.

We claim:

1. A compound of the formula I

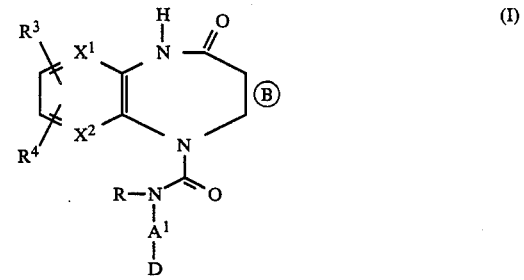

wherein ⒷB represents one of the divalent groups

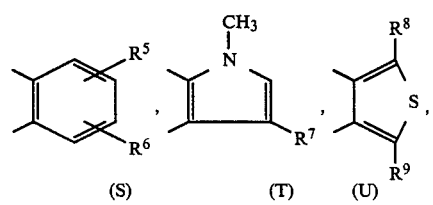

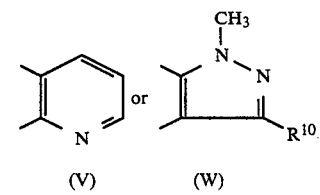

and D represents the groups

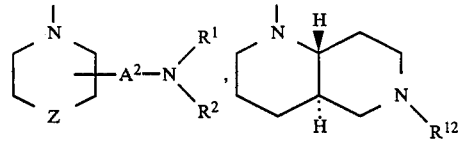

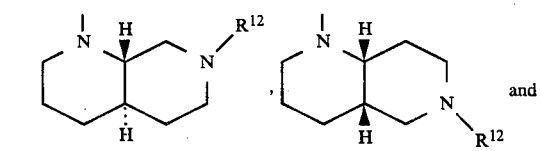

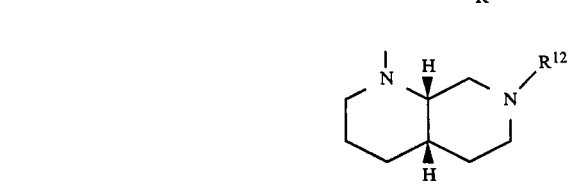

and $X^1$, $X^2$, $A^1$, $A^2$, R, $R^1$ to $R^{10}$, $R^{12}$ and Z have the following meanings:

$X^1$ and $X^2$ represent a =CH— group or, if Ⓑ assumes the meanings of the above-mentioned divalent groups S, U or W, both or only $X^1$ or only $X^2$ may also represent a nitrogen atom;

$A^1$ is a straight-chained or branched saturated alkylene group with two to seven carbon atoms;

$A^2$ is a straight-chained or branched saturated alkylene group with 1 to 5 carbon atoms or, if it is in the 3-position relative to the nitrogen of the saturated heterocyclic ring, it may also represent a single bond;

Z represents a single bond, an oxygen or sulphur atom, a methylene or 1,2-ethylene group;

R represents a hydrogen atom or a methyl group;

$R^1$ represents a branched or unbranched alkyl group with 1 to 4 carbon atoms;

$R^2$ represents a branched or unbranched alkyl group with 1 to 7 carbon atoms which may optionally also be substituted by a hydroxy group at its second to seventh carbon atom, or a cycloalkyl or cycloalkylmethyl group with 3 to 7 carbon atoms in the ring, whilst the cycloalkyl ring may optionally also be substituted by a hydroxy group;

$R^1$ and $R^2$ may, however, also form, together with the nitrogen atom between them, a 4- to 7-membered saturated, monocyclic, heterocyclic ring, bonded via its nitrogen atom to $A^2$, or such a 6-membered ring which may optionally be interrupted in position 4 by an oxygen atom or by the N—$CH_3$ group;

$R^3$ is an alkyl group with 1 to 4 carbon atoms, a chlorine atom or a hydrogen atom;

$R^4$ represents a hydrogen atom or a methyl group;

$R^5$ and $R^6$ each represent a hydrogen atom, a fluorine, chlorine or bromine atom or an alkyl group with 1 to 4 carbon atoms;

$R^7$ represents a hydrogen or chlorine atom or a methyl group;

$R^8$ represents a hydrogen atom or an alkyl group with 1 to 4 carbon atoms;

$R^9$ represents a hydrogen or halogen atom or an alkyl group with 1 to 4 carbon atoms;

$R^{10}$ represents a hydrogen atom or a methyl group and $R^{12}$ represents a branched or unbranched alkyl group with 1 to 6 carbon atoms, whilst if ⌡ⒷⓇ represents the divalent group T and $R^7$ is a hydrogen atom, $R^3$ cannot represent a chlorine atom and Z cannot represent a sulphur atom, or a physiologically acceptable acid addition salt thereof.

2. A compound of the formula I as claimed in claim 1, wherein $X^1$ represents a =CH— group, $X_2$ either represents a nitrogen atom and ⌡Ⓑ represents the divalent group S, with the proviso that $R^3$, $R^4$ and $R^5$ are hydrogen atoms and $R^6$ is a hydrogen atom, a chlorine or bromine atom or a methyl or ethyl group in the 8 or 9 position of the heterocycle, or it is a =CH— group, if ⌡Ⓑ assumes the meaning of the divalent group U, whilst $R^8$ is a hydrogen atom and $R^9$ is a methyl group;

$A^1$ is a 1,2-ethylene group;

$A^2$ is a straight-chained alkylene group with 1 to 5 carbon atoms;

Z is a methylene group;

R is a hydrogen atom; and $R^1$ and $R^2$ represent alkyl groups with 1 to 3 carbon atoms or together with the nitrogen atom between them they represent the piperidinyl group;

or a physiologically acceptable acid addition salt thereof.

3. A compound of the formula I as claimed in claim 1, wherein $X^1$ represents the group =CH—, $X^2$ represents a nitrogen atom or the group =CH—, ⌡Ⓑ represents a divalent group S or U, $A^1$ represents an ethylene group, $A^2$ represents a methylene or 1,3-propylene group, Z represents a methylene group, R represents a hydrogen atom or a methyl group, $R^1$ and $R^2$, which may be identical or different, represents an alkyl group with 1 to 3 carbon atoms, $R^3$ and $R^4$, which may be identical or different, represent hydrogen atoms or a methyl group, $R^5$ and $R^6$ represent hydrogen atoms, $R^8$ and $R^9$ represent hydrogen atoms or one of these groups represents a methyl group, or a physiologically acceptable acid addition salt thereof.

4. As new compounds of general formula I as claimed in claim 1:

5,11-dihydro-11-[[[2-[2-[(dipropylamino)methyl]-piperidin-l-yl]ethyl]amino]carbonyl]-6H-pyrido[2,3-b][1,4]benzodiazepin-6-one, 4-[[[2-[2-[(diethylamino)methyl]-piperidin-1-yl]ethyl]amino]carbonyl]-4,9-dihydro-3-methyl-10H-thieno[3,4-b][1,5]benzodiazepin-10-one, 9-chloro-11-[[[2-[2-[(diethylamino)methyl]-piperidin-l-yl]ethyl]amino]carbonyl]-5,11-dihydro-6H-pyrido[2,3-b][1,4]benzodiazepin-6-one, the diastereomers and enantiomers thereof and their physiologically acceptable salts with inorganic or organic acids.

5. A pharmaceutical composition suitable for the treatment of bradycardia or bradyarrhythmia comprising a therapeutic amount of a compound of formula I, as set forth in claims 1, 2, 3 or 4, and a pharmaceutically acceptable carrier.

6. A method for treating bradycardia or bradyarrhyrhmia which comprises administering to a host suffering from either of these conditions a therapeutic amount of a compound of formula I, as set forth in claims 1, 2, 3 or 4.

* * * * *